United States Patent
Hui et al.

(10) Patent No.: US 11,129,821 B2
(45) Date of Patent: *Sep. 28, 2021

(54) FORMULATIONS OF 2-(4-CHLOROPHENYL)-N-((2-(2,6-DIOXOPIPERIDIN-3-YL)-1-OXOISOINDOLIN-5-YL)METHYL)-2,2-DIFLUOROACETAMIDE

(71) Applicant: Celgene Corporation, Summit, NJ (US)

(72) Inventors: Ho-Wah Hui, Basking Ridge, NJ (US); Yu Pu, East Hanover, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/565,346

(22) Filed: Sep. 9, 2019

(65) Prior Publication Data

US 2020/0237740 A1    Jul. 30, 2020

Related U.S. Application Data

(63) Continuation of application No. 16/040,450, filed on Jul. 19, 2018, now Pat. No. 10,449,187, which is a continuation of application No. 15/400,791, filed on Jan. 6, 2017, now Pat. No. 10,052,315.

(60) Provisional application No. 62/276,756, filed on Jan. 8, 2016.

(51) Int. Cl.
| | | |
|---|---|---|
| *A61K 31/454* | (2006.01) | |
| *A61K 9/00* | (2006.01) | |
| *A61K 9/08* | (2006.01) | |
| *A61K 9/19* | (2006.01) | |
| *A61K 39/395* | (2006.01) | |
| *A61K 47/12* | (2006.01) | |
| *A61K 47/40* | (2006.01) | |
| *C07K 16/00* | (2006.01) | |
| *A61K 47/18* | (2017.01) | |
| *A61K 39/00* | (2006.01) | |

(52) U.S. Cl.
CPC .......... *A61K 31/454* (2013.01); *A61K 9/0019* (2013.01); *A61K 9/0095* (2013.01); *A61K 9/08* (2013.01); *A61K 9/19* (2013.01); *A61K 39/395* (2013.01); *A61K 47/12* (2013.01); *A61K 47/40* (2013.01); *C07K 16/00* (2013.01); *A61K 47/18* (2013.01); *A61K 2039/505* (2013.01)

(58) Field of Classification Search
CPC ................................ A61K 31/454; A61K 9/19
See application file for complete search history.

(56) References Cited

U.S. PATENT DOCUMENTS

| | | | |
|---|---|---|---|
| 4,810,643 A | 3/1989 | Souza | |
| 4,999,291 A | 3/1991 | Souza | |
| 5,229,496 A | 7/1993 | Deeley et al. | |
| 5,391,485 A | 2/1995 | Deeley et al. | |
| 5,393,870 A | 2/1995 | Deeley et al. | |
| 5,528,823 A | 6/1996 | Rudy, Jr. et al. | |
| 5,580,755 A | 12/1996 | Souza | |
| 5,811,097 A | 9/1998 | Allison et al. | |
| 5,855,887 A | 1/1999 | Allison et al. | |
| 5,948,893 A | 9/1999 | June et al. | |
| 6,051,227 A | 4/2000 | Allison et al. | |
| 6,207,157 B1 | 3/2001 | Gu et al. | |
| 6,352,694 B1 | 3/2002 | June et al. | |
| 6,534,055 B1 | 3/2003 | June et al. | |
| 6,682,736 B1 | 1/2004 | Hanson et al. | |
| 6,692,964 B1 | 2/2004 | June et al. | |
| 6,887,466 B2 | 5/2005 | June et al. | |
| 6,905,681 B1 | 6/2005 | June et al. | |
| 6,984,720 B1 | 1/2006 | Korman et al. | |
| 7,488,802 B2 | 2/2009 | Collins et al. | |
| 7,498,171 B2 | 3/2009 | Hariri et al. | |
| 7,605,238 B2 | 10/2009 | Korman et al. | |
| 7,943,743 B2 | 5/2011 | Korman et al. | |
| 8,008,449 B2 | 8/2011 | Korman et al. | |
| 8,168,757 B2 | 5/2012 | Finnefrock et al. | |
| 8,217,149 B2 | 7/2012 | Irving et al. | |
| 9,499,514 B2 | 11/2016 | Hansen et al. | |
| 9,808,451 B2 | 11/2017 | Cathers et al. | |
| 9,938,254 B2 | 4/2018 | Alexander et al. | |
| 9,968,596 B2 | 5/2018 | Cathers et al. | |
| 10,052,315 B2 | 8/2018 | Hui et al. | |
| 10,449,187 B2 * | 10/2019 | Hui | A61K 9/0095 |
| 2012/0122865 A1 | 5/2012 | Muller et al. | |
| 2012/0252844 A1 | 10/2012 | Dewitt | |

(Continued)

FOREIGN PATENT DOCUMENTS

| | | | |
|---|---|---|---|
| WO | WO 2003/042402 A2 | 5/2003 | |
| WO | WO 2008/156712 A1 | 12/2008 | |

(Continued)

OTHER PUBLICATIONS

Anguille et al., "Leukemia-associated antigens and their relevance to the immunotherapy of acute myeloid leukemia," *Leukemia*, 26(10):2186-2196 (2012).

(Continued)

*Primary Examiner* — James D. Anderson
(74) *Attorney, Agent, or Firm* — Jones Day

(57) ABSTRACT

Provided herein are lyophilized formulations of 2-(4-chlorophenyl)—N—((2-(2,6-dioxopiperidin-3-yl)-1-oxoisoindolin-5-yl)methyl)-2,2-difluoroacetamide or a stereoisomer or mixture of stereoisomers, pharmaceutically acceptable salt, tautomer, prodrug, solvate, hydrate, co-crystal, clathrate, or polymorph thereof. Methods of using the formulations and dosage forms for treating, managing, and/or preventing cancer are also provided herein.

26 Claims, 34 Drawing Sheets

(56) References Cited

U.S. PATENT DOCUMENTS

| | | |
|---|---|---|
| 2014/0328832 A1 | 11/2014 | Chopra et al. |
| 2017/0197934 A1 | 7/2017 | Fernandez et al. |
| 2018/0186767 A1 | 7/2018 | Alexander et al. |
| 2018/0221361 A1 | 8/2018 | Cathers et al. |

FOREIGN PATENT DOCUMENTS

| | | |
|---|---|---|
| WO | WO 2009/145899 A1 | 12/2009 |
| WO | WO 2010/036959 A2 | 4/2010 |
| WO | WO 2010/053732 A1 | 5/2010 |
| WO | WO 2010/089411 A2 | 8/2010 |
| WO | WO 2011/066342 A2 | 6/2011 |
| WO | WO 2011/082400 A2 | 7/2011 |
| WO | WO 2011/159877 A2 | 12/2011 |
| WO | WO 2011/161699 A2 | 12/2011 |
| WO | WO 2016/007848 A1 | 1/2016 |

OTHER PUBLICATIONS

Brignone et al., "A soluble form of lymphocyte activation gene-3 (IMP321) induces activation of a large range of human effector cytotoxic cells," *J. Immunol.*, 179(6):4202-4211 (2007).

Emens et al., "Chemotherapy: friend of foe to cancer vaccines," *Curr. Opin. Mol. Ther.*, 3(1):77-84 (2001).

Fourcade et al., "Upregulation of Tim-3 and PD-1 expression is associated with tumor antigen-specific CD8+ T cell dysfunction in melanoma patients," *J. Exp. Med.*, 207(10):2175-2186 (2010).

Hoffmann-Ostenhof, "IUPAC-IUB commission on biochemical nomenclature abbreviated nomenclature of synthetic polypeptides (polymerized amino acids)", *Biochem.*, 11(5):942-944 (1972).

Loo et al., "Development of an Fc-enhanced anti-B7-H3 monoclonal antibody with potent antitumor activity," *Clin. Cancer Res.*, 18(14):3834-3845 (2012).

Oncology Tools, Dose Calculator and Dose Calculator Results, U.S. Food and Drug Administration, Center for Drug Evaluation and Research (2008), retrieved on the internet URL:https://web.archive.org/web/20080223150428/http://www.fda.gov/cder/cancer/animalframe.htm, retrieved on Jan. 24, 2017, 1 page.

Pardoll, "The blockade of immune checkpoints in cancer immunotherapy," *Nat. Rev. Cancer*, 12(4):252-264 (2012).

Penichet et al., "Antibody-cytokine fusion proteins for the therapy of cancer," *J. Immunol. Methods*, 284:91-101 (2001).

Sakuishi et al., "Targeting Tim-3 and PD-1 pathways to reverse T cell exhaustion and restore anti-tumor immunity," *J. Exp. Med.*, 207(10):2187-2194 (2010).

Straathof et al., "An inducible caspase 9 safety switch for T-cell therapy," *Blood*, 105(11):4247-4254 (2005).

Therasse et al., "New guidelines to evaluate the response to treatment in solid tumors. European Organization for Research and Treatment of Cancer, National Cancer Institute of the United States, National Cancer Institute of Canada," *J. Natl. Cancer Inst.*, 92(3):205-216 (2000).

Office Action for U.S. Appl. No. 15/400,791, dated Oct. 12, 2017 (10 pages).

Notice of Allowance for U.S. Appl. No. 15/400,791, dated Apr. 17, 2018 (8 pages).

Office Action for U.S. Appl. No. 16/040,450, dated Dec. 17, 2018 (8 pages).

Notice of Allowance for U.S. Appl. No. 16/040,450, dated Jun. 10, 2019 (9 pages).

\* cited by examiner

DVS Isotherm Plot  
Temp: 25.0°C  
MRef: 2.5895

|       | Target % P/Po | Change In Mass (%)−ref Sorption | Desorption | Hysteresis |
|-------|---------------|---------------------------------|------------|------------|
| Cycle 1 | 0.0   | 0.000 | −0.270 |        |
|       | 10.0  | 0.093 | −0.120 | −0.213 |
|       | 20.0  | 0.241 | 0.009  | −0.232 |
|       | 30.0  | 0.439 | 0.112  | −0.327 |
|       | 40.0  | 0.595 | 0.292  | −0.303 |
|       | 50.0  | 0.700 | 0.456  | −0.244 |
|       | 60.0  | 0.798 | 0.599  | −0.198 |
|       | 70.0  | 0.903 | 0.748  | −0.154 |
|       | 80.0  | 0.977 | 0.886  | −0.091 |
|       | 90.0  | 1.085 | 1.085  |        |

4-week stability samples at 25°C/60% RH

FORMULATIONS OF 2-(4-CHLOROPHENYL)-N-((2-(2,6-DIOXOPIPERIDIN-3-YL)-1-OXOISOINDOLIN-5-YL)METHYL)-2,2-DIFLUOROACETAMIDE

1. CROSS REFERENCE TO RELATED APPLICATION

This application claims priority under 35 U.S.C. § 120 to, and is a continuation of U.S. application Ser. No. 16/040,450 filed Jul. 19, 2018, currently allowed, which is a continuation of U.S. application Ser. No. 15/400,791 filed Jan. 6, 2017, issued as U.S. Pat. No. 10,052,315 on Aug. 21, 2018, which claims the benefit of the priority of U.S. Provisional Application No. 62/276,756, filed Jan. 8, 2016, the disclosures of each which are incorporated herein by reference in their entireties.

2. FIELD

Provided herein are formulations and dosage forms of 2-(4-chlorophenyl)-N-((2-(2,6-dioxopiperidin-3-yl)-1-oxoisoindolin-5-yl)methyl)-2,2-difluoroacetamide or a stereoisomer or a mixture of stereoisomers, pharmaceutically acceptable salt, tautomer, prodrug, solvate, hydrate, co-crystal, clathrate, or polymorph thereof. Methods of using the formulations and dosage forms for treating, managing, and/or preventing cancer are also provided herein.

3. BACKGROUND

Drug substances are usually administered as part of a formulation in combination with one or more other agents that serve varied and specialized pharmaceutical functions. Dosage forms of various types may be made through selective use of pharmaceutical excipients. Pharmaceutical excipients have various functions and contribute to the pharmaceutical formulations in many different ways, e.g., solubilization, dilution, thickening, stabilization, preservation, coloring, flavoring, etc. The properties of pharmaceutical excipients that are considered when formulating an active drug substance include bioavailability, ease of manufacture, ease of administration, and stability of the dosage form. Due to the varying properties of the active drug substance to be formulated, and cross-reactivity between excipients, dosage forms typically require pharmaceutical excipients that are uniquely tailored to the active drug substance to achieve advantageous physical and pharmaceutical properties.

Nevertheless, use of pharmaceutical excipients in formulating dosage forms can, in some instances, cause undesirable adverse reactions with the active ingredient which manifest upon, for example, prolonged storage or contact with water. Indeed, it is well known that the properties of the final dosage form (e.g., its bioavailability and stability) are, for the most part, highly dependent on the excipients chosen, their concentration and interaction with both the active compound and each other. Excipients are more than inert or inactive ingredients and must be selected to avoid undesirable cross-reaction with active ingredients and other excipients in the formulation. Selecting compatible excipients is critical in formulating dosage forms to ensure the active ingredient is properly delivered and that the dosage form is a stable formulation.

2-(4-Chlorophenyl)-N-((2-(2,6-dioxopiperidin-3-yl)-1-oxoisoindolin-5-yl)methyl)-2,2-difluoroacetamide or a stereoisomer or mixture of stereoisomers, pharmaceutically acceptable salt, tautomer, prodrug, solvate, hydrate, co-crystal, clathrate, or polymorph thereof has been shown to have anticancer activities. There is a need for formulations of 2-(4-chlorophenyl)-N-((2-(2,6-dioxopiperidin-3-yl)-1-oxoisoindolin-5-yl)methyl)-2,2-difluoroacetamide or a stereoisomer or mixture of stereoisomers, pharmaceutically acceptable salt, tautomer, prodrug, solvate, hydrate, co-crystal, clathrate, or polymorph thereof for treatment of cancer.

4. BRIEF SUMMARY

Provided herein are lyophilized formulations comprising 2-(4-chlorophenyl)-N-((2-(2,6-dioxopiperidin-3-yl)-1-oxoisoindolin-5-yl)methyl)-2,2-difluoroacetamide, or a stereoisomer or mixture of stereoisomers, pharmaceutically acceptable salt, tautomer, prodrug, solvate, hydrate, co-crystal, clathrate, or polymorph thereof ("Compound 1") and a pharmaceutically acceptable excipient. Compound 1 is described in U.S. Pat. No. 9,499,514 and International Publication No. WO 2016/007848, the disclosures of each which are incorporated herein by reference in their entireties. In one embodiment, Compound 1 is polymorph Form A, Form B, Form C, Form D, Form E or an amorphous form of 2-(4-chlorophenyl)-N-((2-(2,6-dioxopiperidin-3-yl)-1-oxoisoindolin-5-yl)methyl)-2,2-difluoroacetamide. In one embodiment, Compound 1 is polymorph Form C of 2-(4-chlorophenyl)-N-((2-(2,6-dioxopiperidin-3-yl)-1-oxoisoindolin-5-yl)methyl)-2,2-difluoroacetamide. The polymorphs of 2-(4-chlorophenyl)-N-((2-(2,6-dioxopiperidin-3-yl)-1-oxoisoindolin-5-yl)methyl)-2,2-difluoroacetamide are described herein and in U.S. provisional patent application No. 62/276,750 filed on Jan. 8, 2016, entitled SOLID FORMS OF 2-(4-CHLOROPHENYL)-N-((2-(2,6-DIOXOPIPERIDIN-3-YL)-1-OXOISOINDOLIN-5-YL)METHYL)-2,2-DIFLUOROACETAMIDE, AND THEIR PHARMACEUTICAL COMPOSITIONS AND USES", the disclosure of which is incorporated herein by reference in its entirety.

In certain embodiments, the lyophilized formulations provided herein comprise a solid form of 2-(4-chlorophenyl)-N-((2-(2,6-dioxopiperidin-3-yl)-1-oxoisoindolin-5-yl)methyl)-2,2-difluoroacetamide. In certain embodiments, the lyophilized formulations provided herein comprise an amorphous form of 2-(4-chlorophenyl)-N-((2-(2,6-dioxopiperidin-3-yl)-1-oxoisoindolin-5-yl)methyl)-2,2-difluoroacetamide.

In one aspect, the lyophilized formulations provided herein are suitable for reconstitution with a suitable diluent to the appropriate concentration prior to administration. In one embodiment, the lyophilized formulation is stable at room temperature. In one embodiment, the lyophilized formulation is stable at room temperature for up to about 24 months. In one embodiment, the lyophilized formulation is stable at room temperature for up to about 24 months, up to about 18 months, up to about 12 months, up to about 6 months, up to about 3 months or up to about 1 month. In one embodiment, the lyophilized formulation is stable upon storage under accelerated condition of 40° C./75% RH for up to about 12 months, up to about 6 months or up to about 3 months.

In one aspect, the lyophilized formulation provided herein is suitable for reconstitution with an aqueous solution for intravenous administrations. In one aspect, the lyophilized formulation provided herein is suitable for reconstitution with water. In one embodiment, the reconstituted aqueous solution is stable at room temperature for up to about 24 hours upon reconstitution. In one embodiment, the reconstituted aqueous solution is stable at room temperature from about 1-24, 2-20, 2-15, 2-10 hours upon reconstitution. In one embodiment, the reconstituted aqueous solution is stable at room temperature for up to about 20, 15, 12, 10, 8, 6, 4 or 2 hours upon reconstitution. In certain embodiments, the lyophilized formulations upon reconstitution have a pH of about 4 to 5.

In certain embodiment, the lyophilized formulations provided herein comprise Compound 1, a pH adjusting agent and a bulking agent.

In one embodiment, the lyophilized formulation provided herein comprises about 0.1-2% Compound 1, about 1-15% buffer and about 70-95% bulking agent based on the total weight of the lyophilized formulation.

In another aspect provided herein is a lyophilized formulation comprising Compound 1 in about 0.1 to about 2% based on the total weight of the lyophilized formulation. In still another aspect, provided herein is a lyophilized formulation that comprises Compound 1 in an amount of about 0.1 mg to about 5 mg in a vial, for example, a 20 cc vial.

In one aspect, the formulations provided herein comprise a citrate buffer in an amount from about 5% to about 25% based on total weight of the lyophilized formulation. In one embodiment, the citrate buffer comprises anhydrous citric acid and anhydrous sodium citrate.

In one aspect, the bulking agent in the formulations provided herein comprises Captisol®, mannitol or Kleptose®, for example, β-cyclodextrin, hydroxypropyl β-cyclodextrin and methylated β-cyclodextrin.

In certain embodiments, provided herein is a unit dosage form comprising a lyophilized formulation, wherein the lyophilized formulation comprises Compound 1, a buffer and a bulking agent.

In certain embodiments, provided herein is a container comprising a lyophilized formulation provided herein. In one aspect, the container is a glass vial.

In certain embodiments, provided herein are methods of treating, preventing or ameliorating cancer, including solid tumors and blood borne tumors, or one or more symptoms or causes thereof. In certain embodiments, provided herein are methods of preventing cancer, including solid tumors and blood borne tumors, or one or more symptoms or causes thereof. In certain embodiments, provided herein are methods of ameliorating cancer, including solid tumors and blood borne tumors, or one or more symptoms or causes thereof. In certain embodiments, the blood borne tumor is leukemia. In certain embodiments, methods provided herein encompass methods of treating various forms of leukemias such as chronic lymphocytic leukemia, chronic myeloid leukemia, acute lymphocytic leukemia, acute myeloid leukemia and acute myeloblastic leukemia. In certain embodiments, methods provided herein encompass methods of preventing various forms of leukemias such as chronic lymphocytic leukemia, chronic myeloid leukemia, acute lymphocytic leukemia, acute myeloid leukemia and acute myeloblastic leukemia. In certain embodiments, methods provided herein encompass methods of managing various forms of leukemias such as chronic lymphocytic leukemia, chronic myeloid leukemia, acute lymphocytic leukemia, acute myeloid leukemia and acute myeloblastic leukemia. The methods provided herein include treatment of leukemias that are relapsed, refractory or resistant. The methods provided herein include prevention of leukemias that are relapsed, refractory or resistant. The methods provided herein include management of leukemias that are relapsed, refractory or resistant. In one embodiment, methods provided herein encompass methods of treating acute myeloid leukemia. In one embodiment, methods provided herein encompass methods of preventing acute myeloid leukemia. In one embodiment, methods provided herein encompass methods of managing acute myeloid leukemia. In one embodiment, methods provided herein encompass methods of treating a myelodysplastic syndrome. In one embodiment, methods provided herein encompass methods of preventing a myelodysplastic syndrome. In one embodiment, methods provided herein encompass methods of managing a myelodysplastic syndrome.

In one embodiment, provided herein are methods of treating acute myeloid leukemia by intravenous administration of a formulation comprising Compound 1. In one embodiment, provided herein are methods of treating a myelodysplastic syndrome by intravenous administration of a formulation comprising Compound 1.

In practicing the methods, compositions containing therapeutically effective concentrations of Compound 1 are administered to an individual exhibiting the symptoms of the disease or disorder to be treated. The amounts are effective to ameliorate or eliminate one or more symptoms of the disease or disorder.

Further provided is a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use of sale for human administration. The pack or kit can be labeled with information regarding mode of administration, sequence of drug administration (e.g., separately, sequentially or concurrently), or the like.

These and other aspects of the subject matter described herein will become evident upon reference to the following detailed description.

5. BRIEF DESCRIPTION OF THE DRAWINGS

Figure 6:
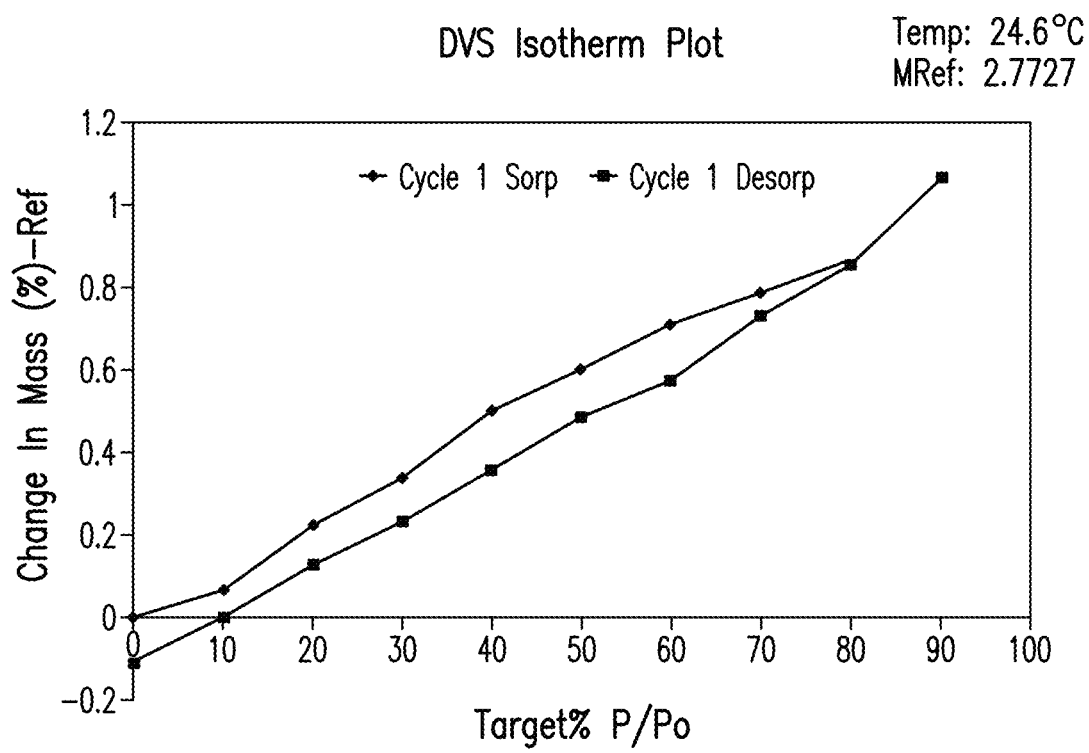

FIG. 6 provides a dynamic vapor sorption (DVS) isotherm plot of Form A of Compound 1.

Figure 7:
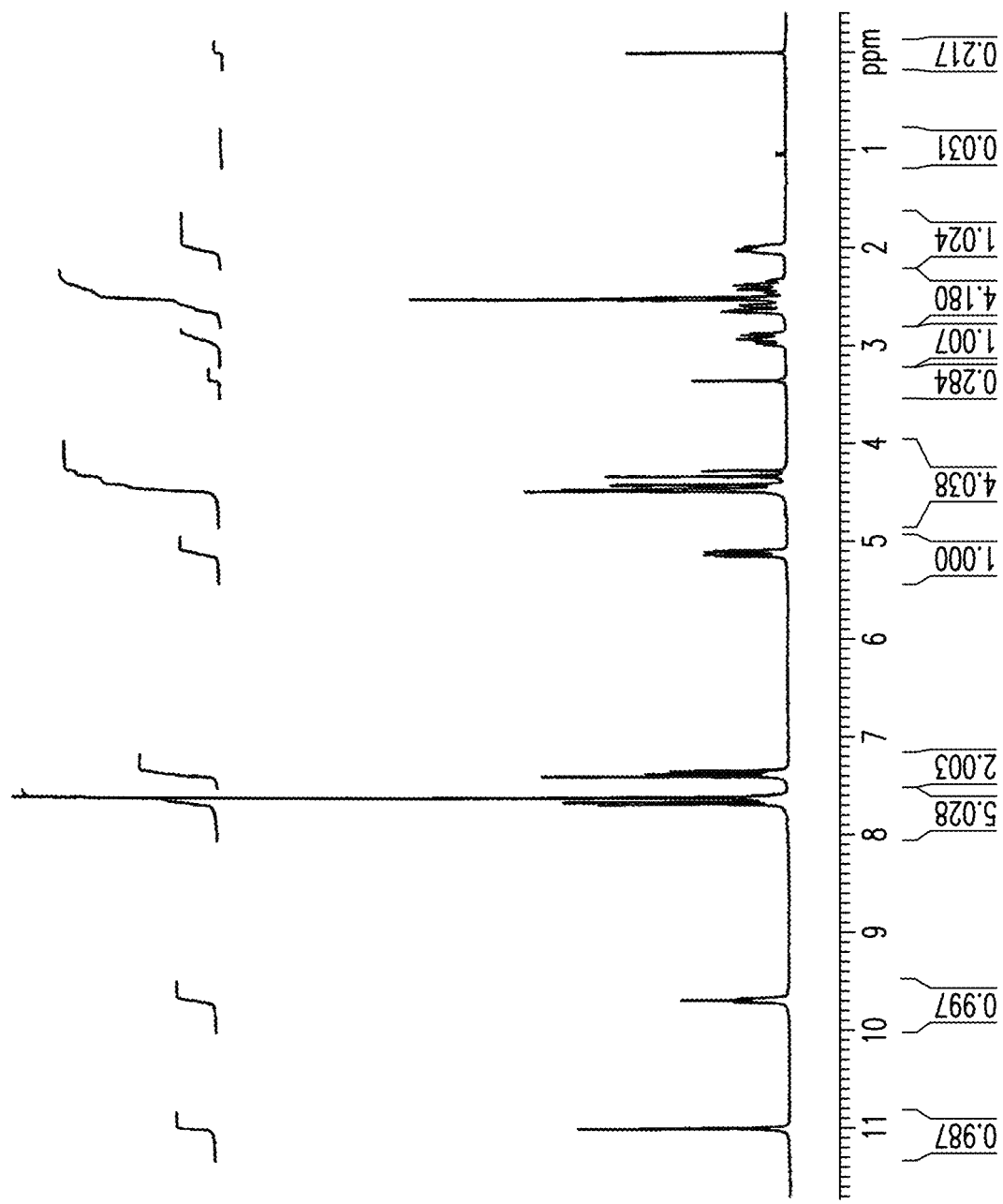

FIG. 7 provides a $^1$H NMR spectrum of Form A of Compound 1.

Figure 8:
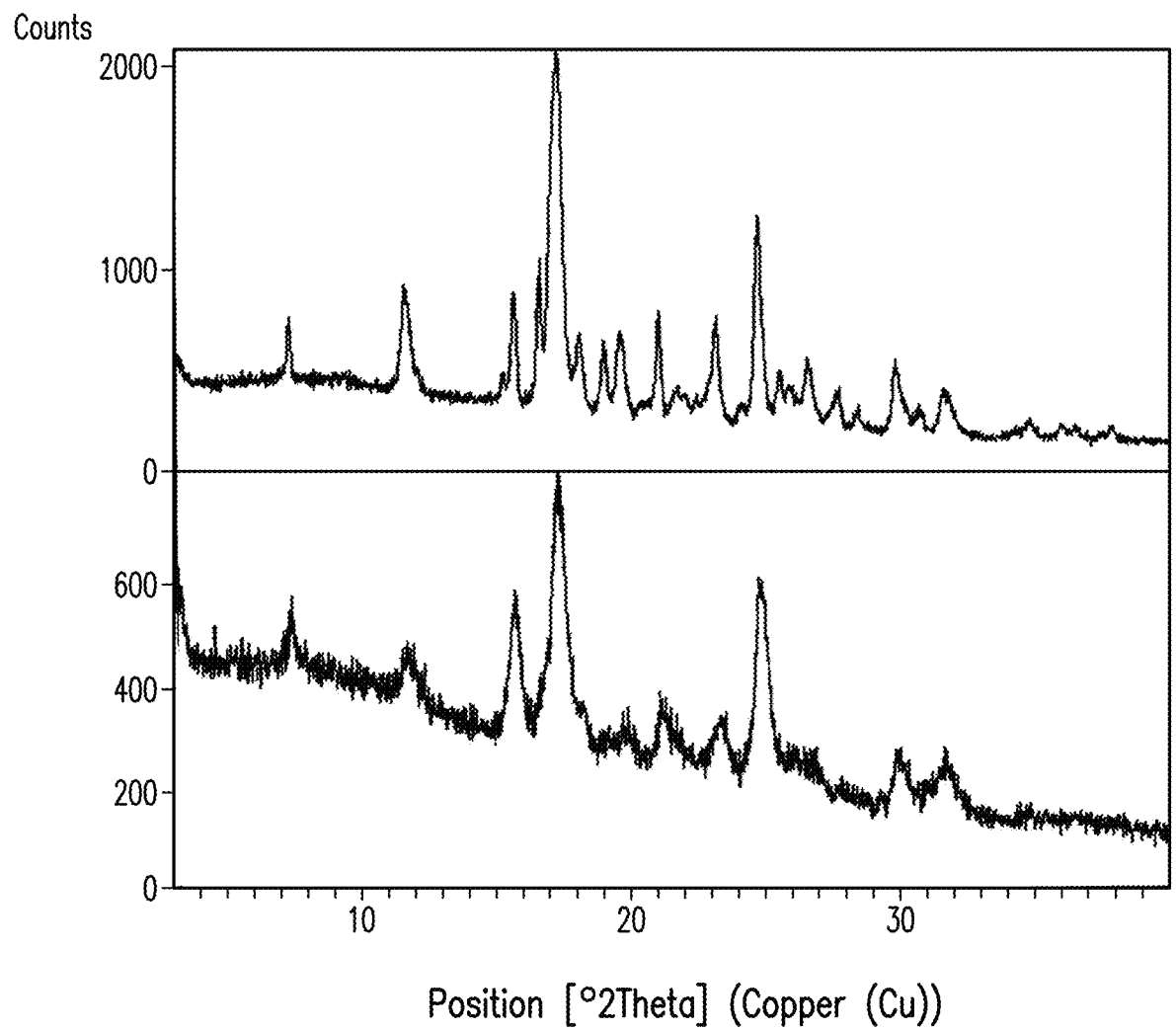

FIG. 8 depicts the comparison of the X-ray powder diffractogram plots of Form A of Compound 1 before (a) and after (b) compression.

Figure 9:
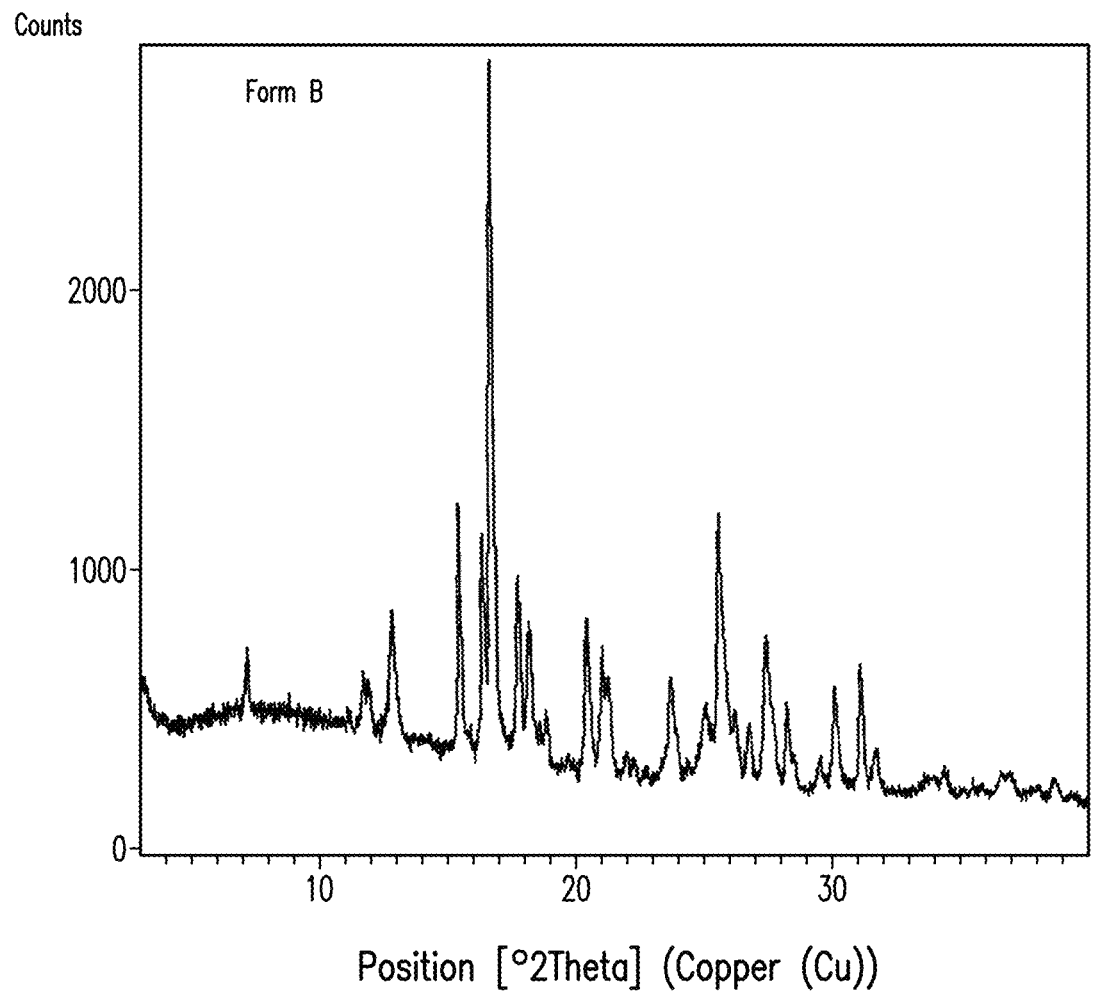

FIG. 9 depicts an XRPD plot of Form B of Compound 1.

Figure 10:
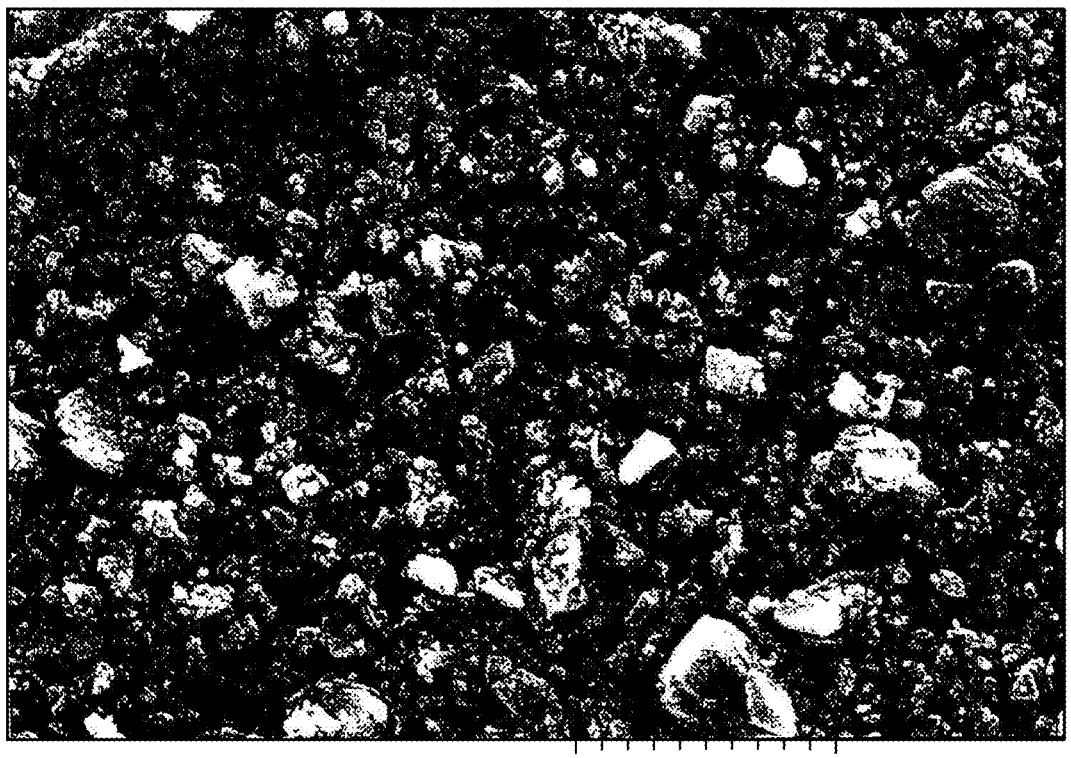

FIG. 10 depicts a SEM image of Form B of Compound 1.

Figure 11:
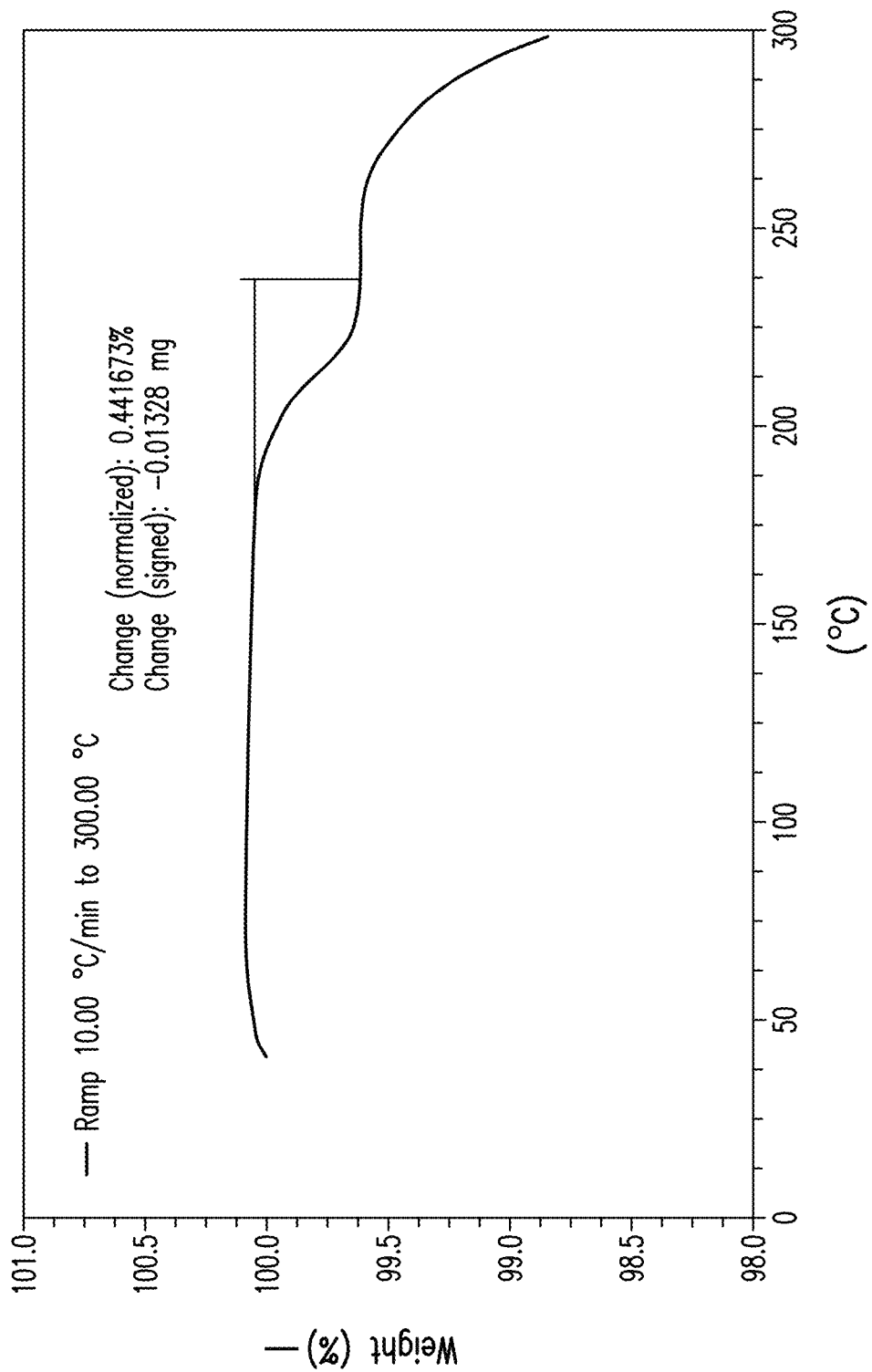

FIG. 11 depicts a TGA thermogram plot of Form B of Compound 1.

Figure 12:
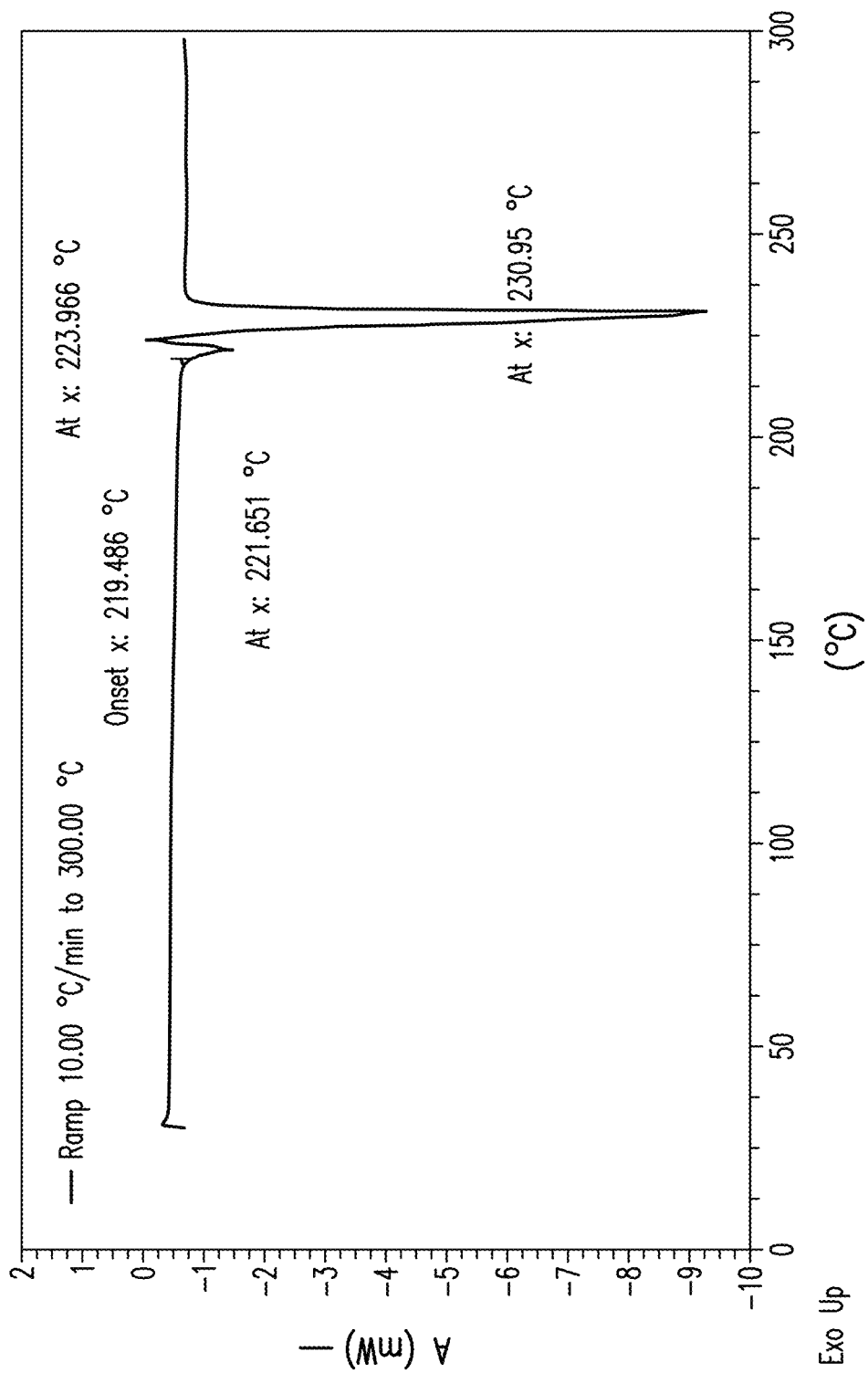

FIG. 12 depicts a DSC thermogram plot of Form B of Compound 1.

Figure 13:
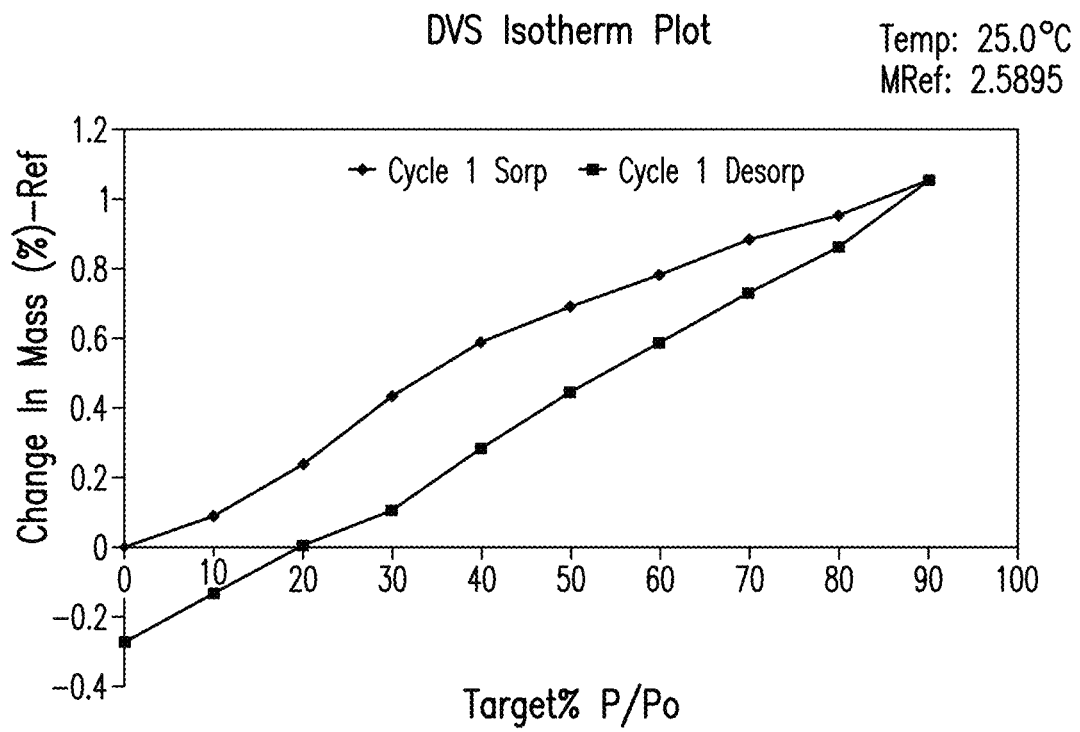

FIG. 13 provides a DVS isotherm plot of Form B of Compound 1.

Figure 14:
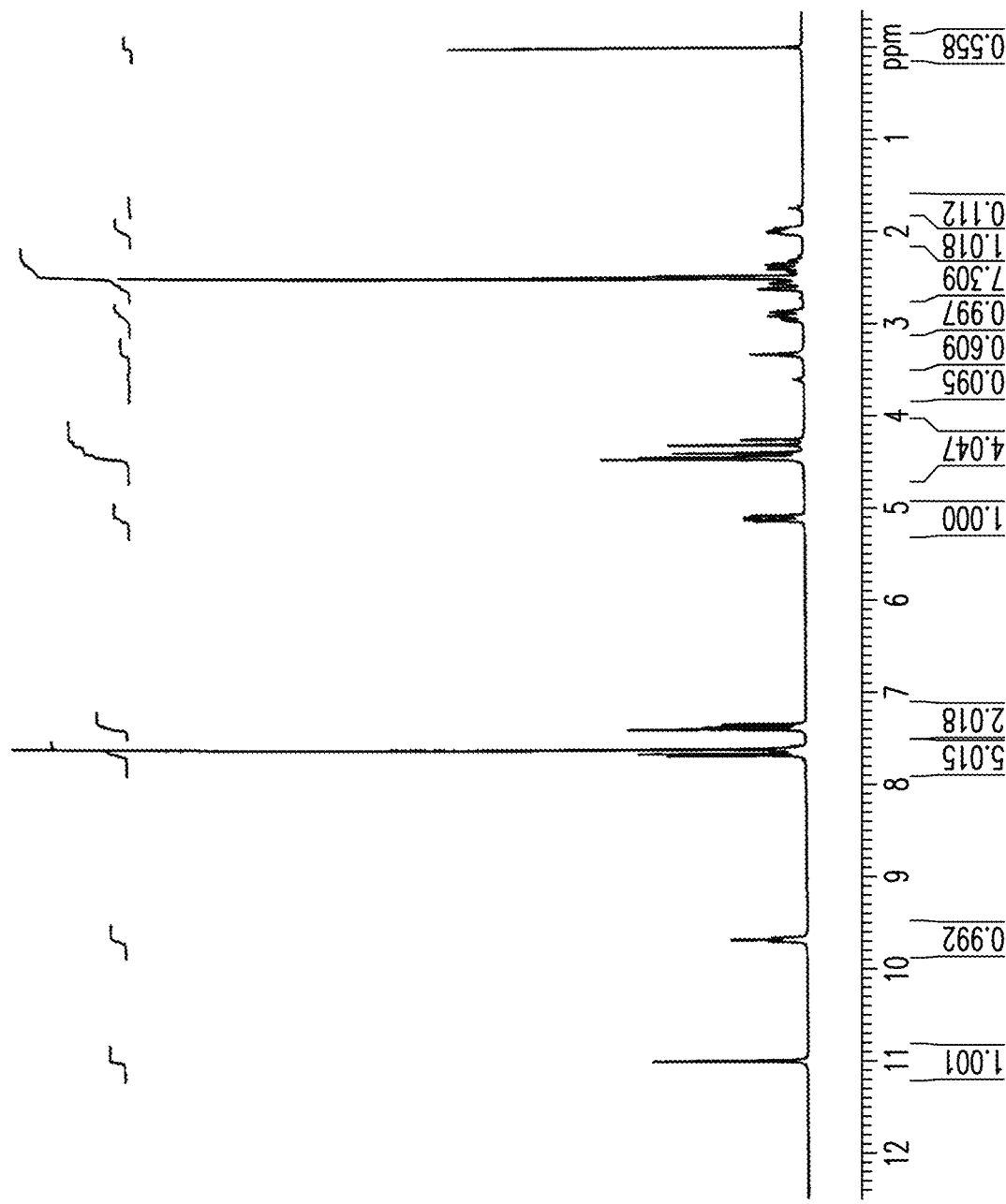

FIG. 14 provides a $^1$H NMR spectrum of Form B of Compound 1.

Figure 15:
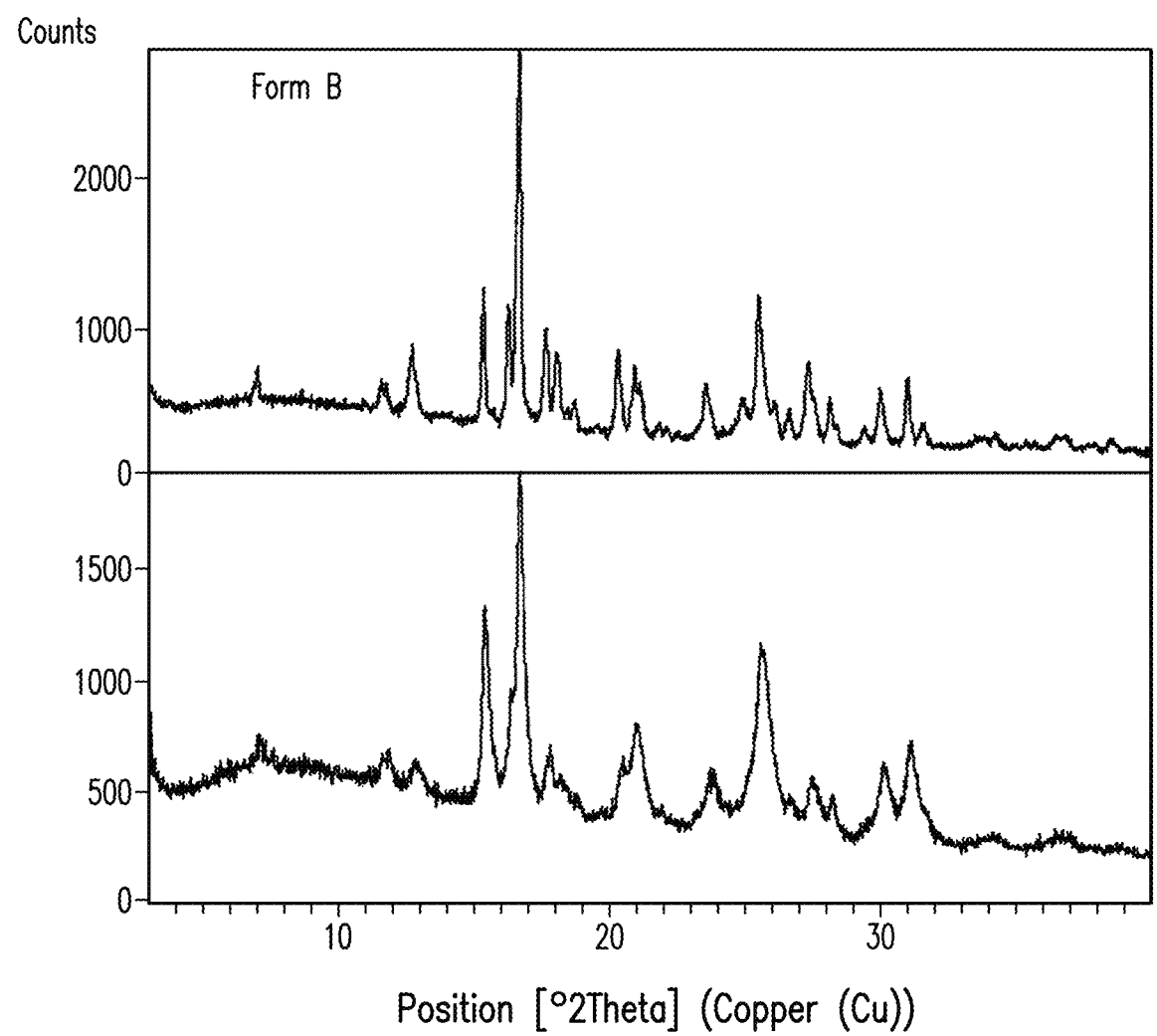

FIG. 15 depicts the comparison of the X-ray powder diffractogram plots of Form B of Compound 1 before (a) and after (b) compression.

Figure 16:
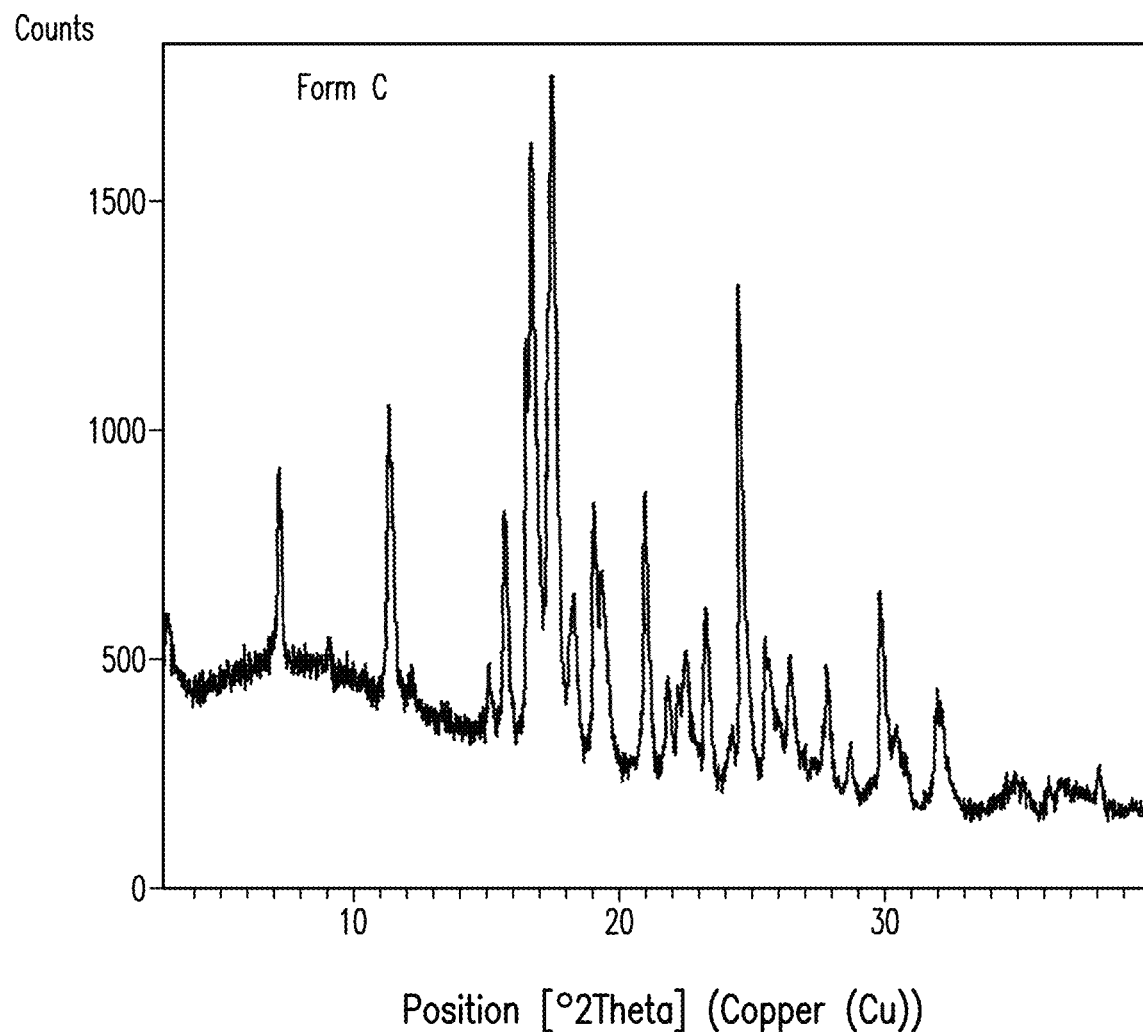

FIG. 16 depicts an XRPD plot of Form C of Compound 1.

Figure 17:
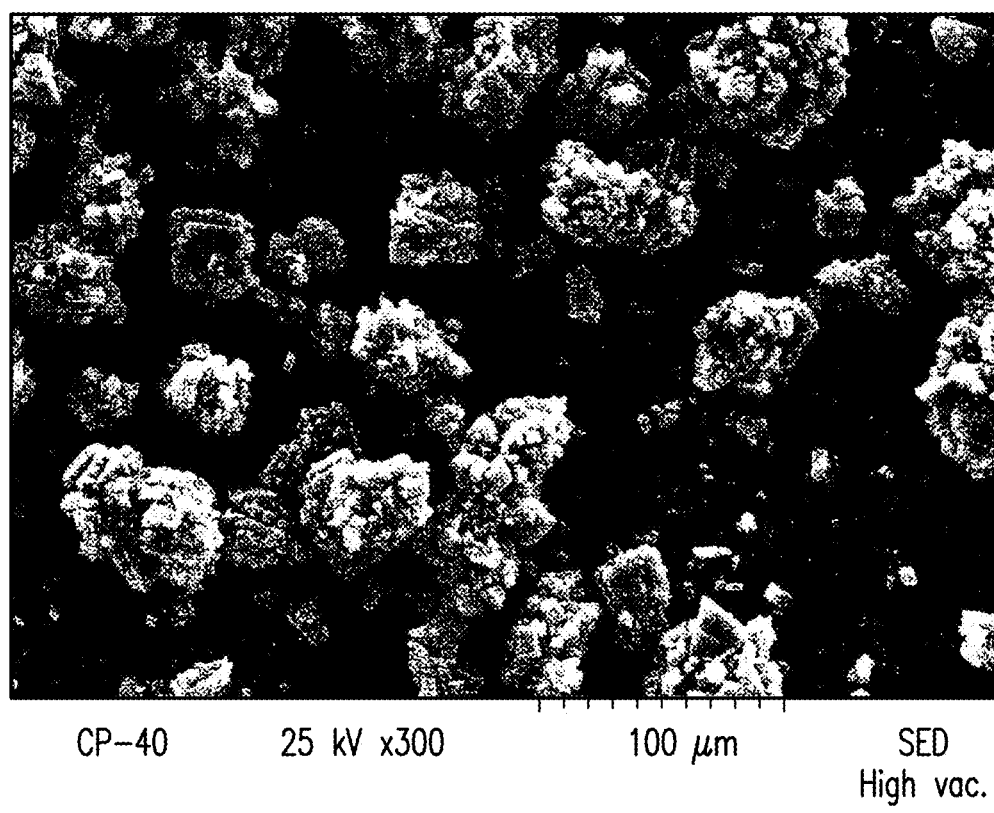

FIG. 17 depicts a SEM image of Form C of Compound 1.

Figure 18:
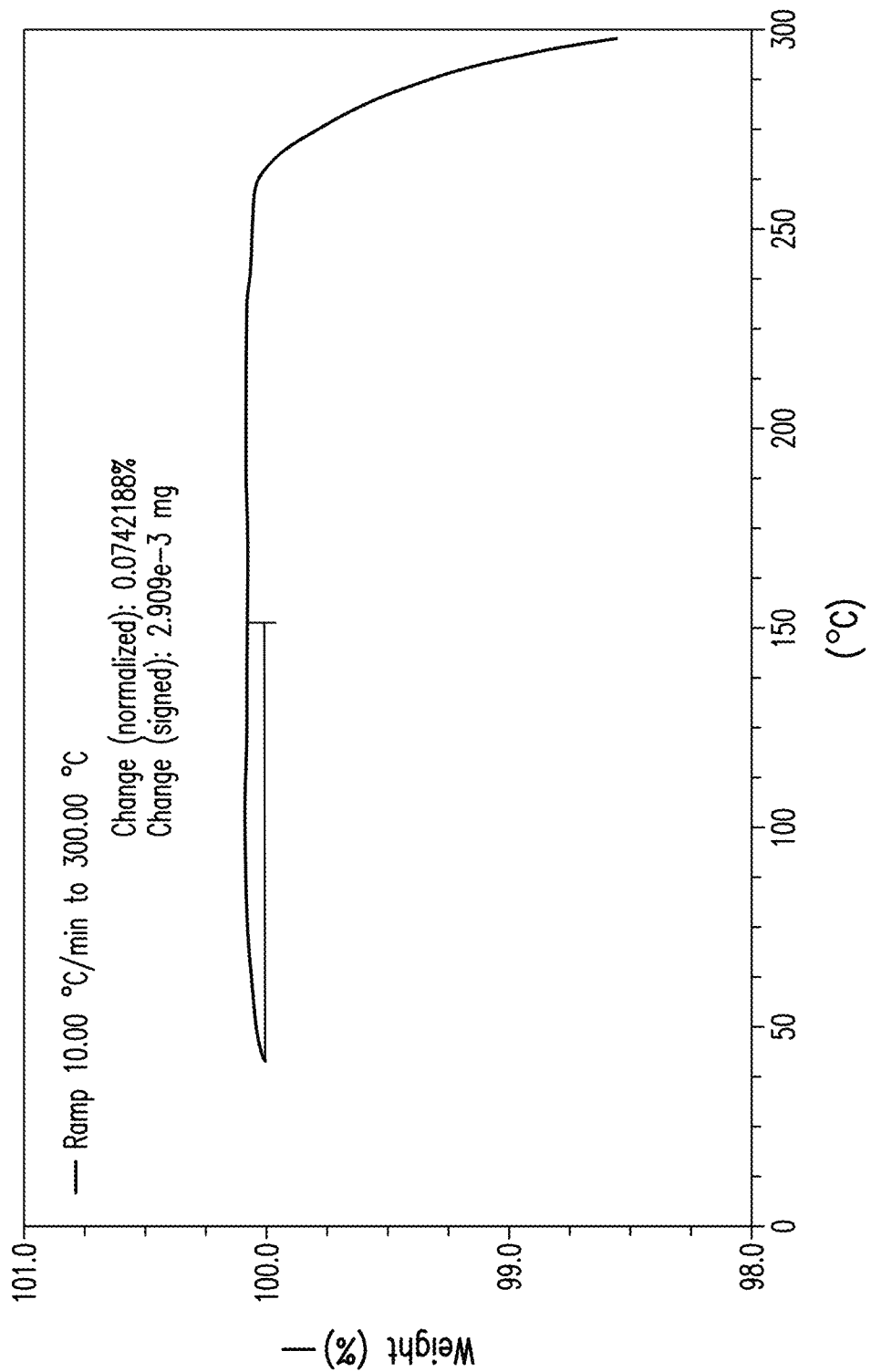

FIG. 18 depicts a TGA thermogram plot of Form C of Compound 1.

Figure 19:
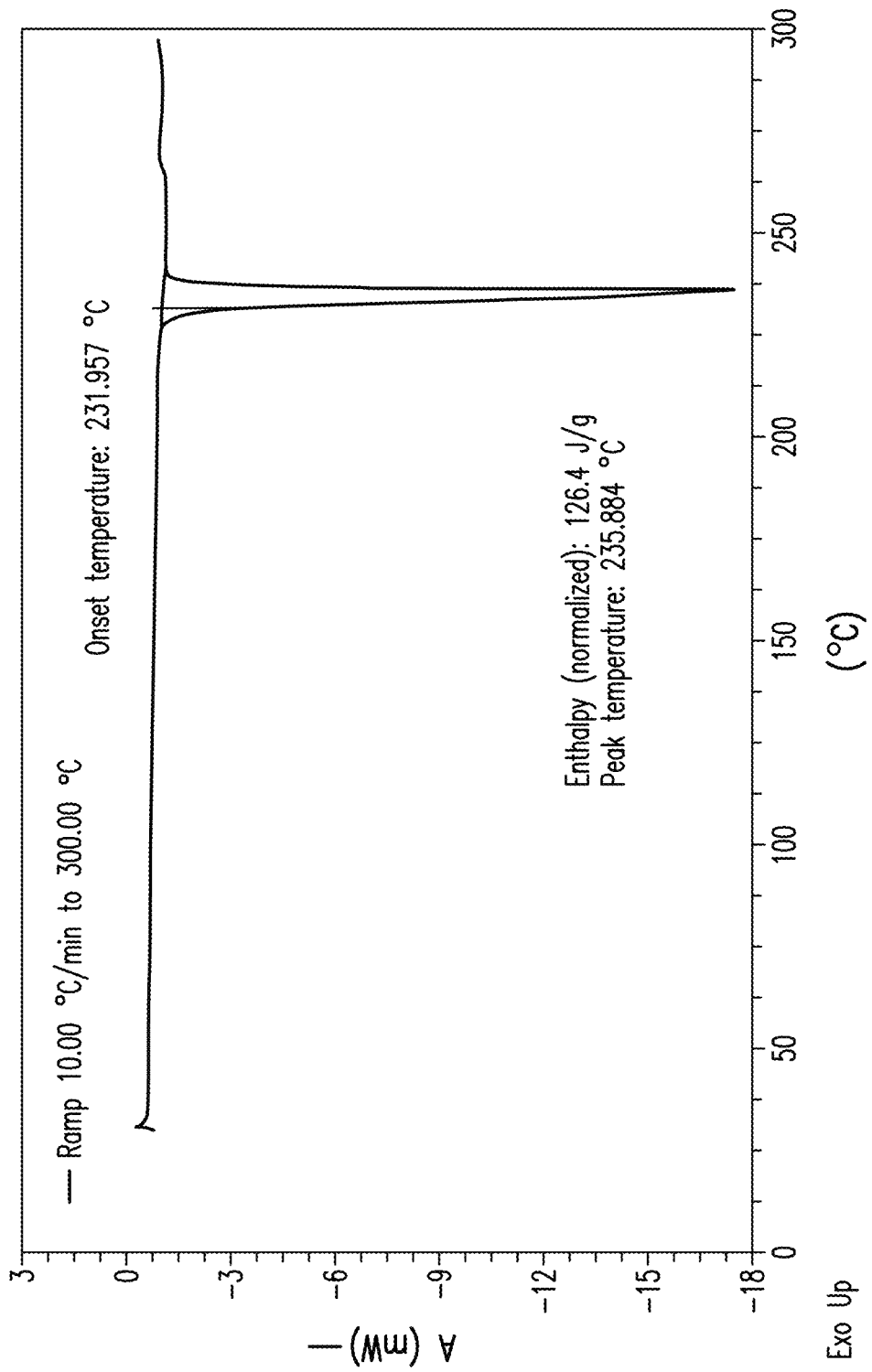

FIG. 19 depicts a DSC thermogram of Form C of Compound 1.

Figure 20:
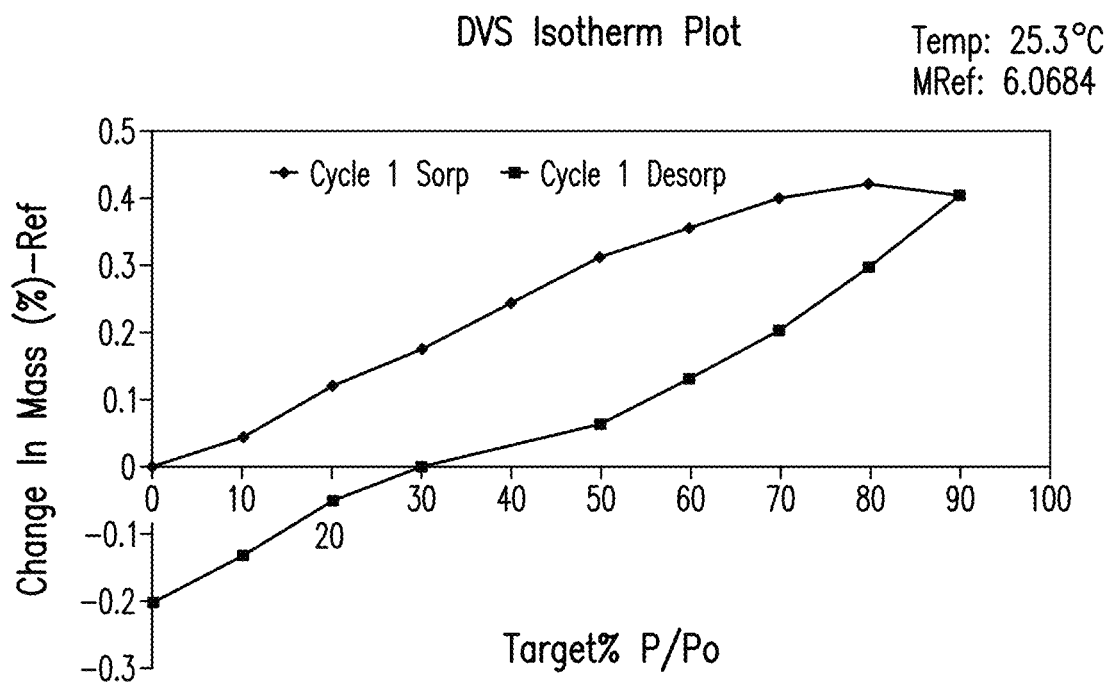

FIG. 20 provides a DVS isotherm plot of Form C of Compound 1.

Figure 21:
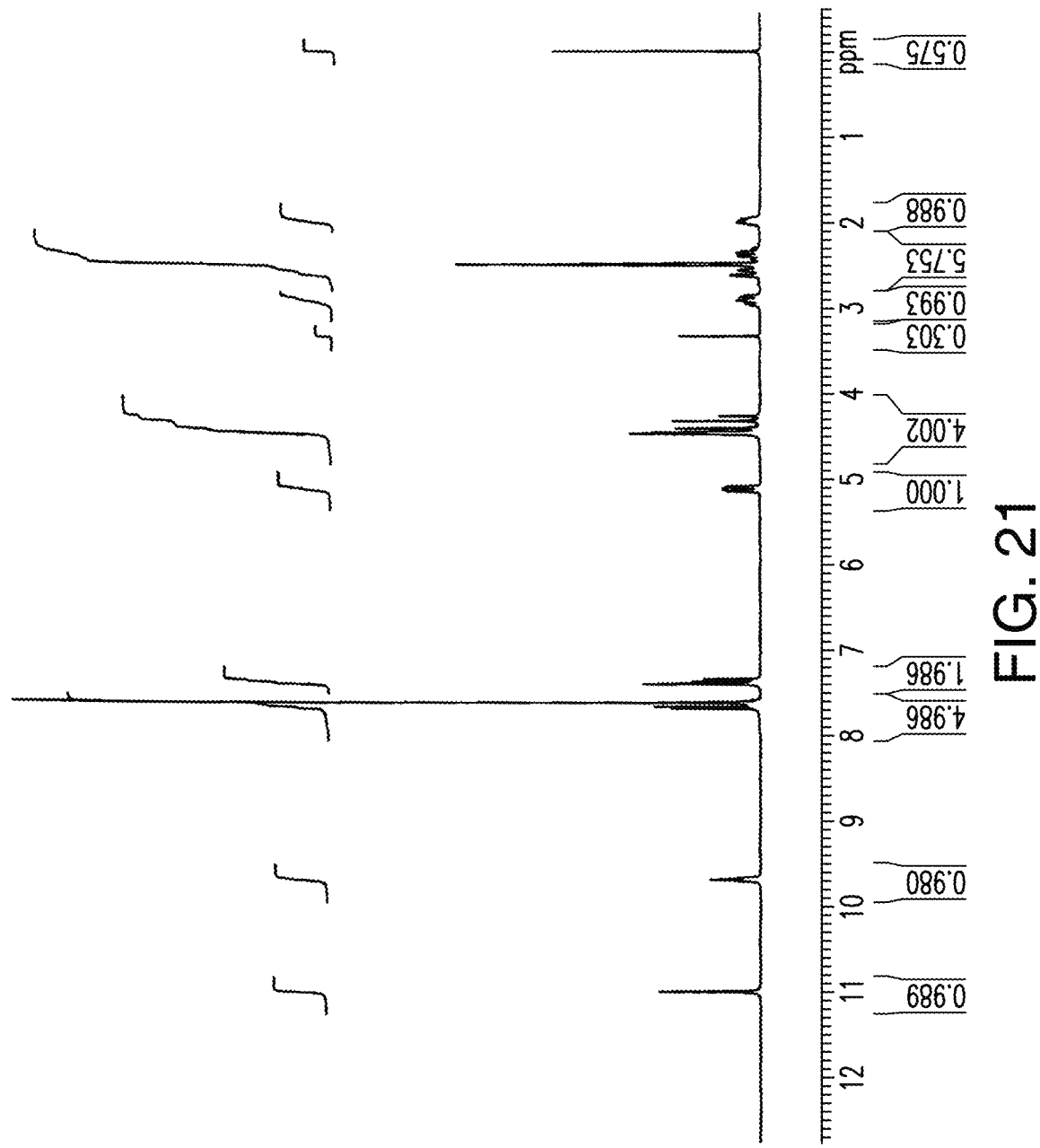

FIG. 21 provides a $^1$H NMR spectrum of Form C of Compound 1.

Figure 22:
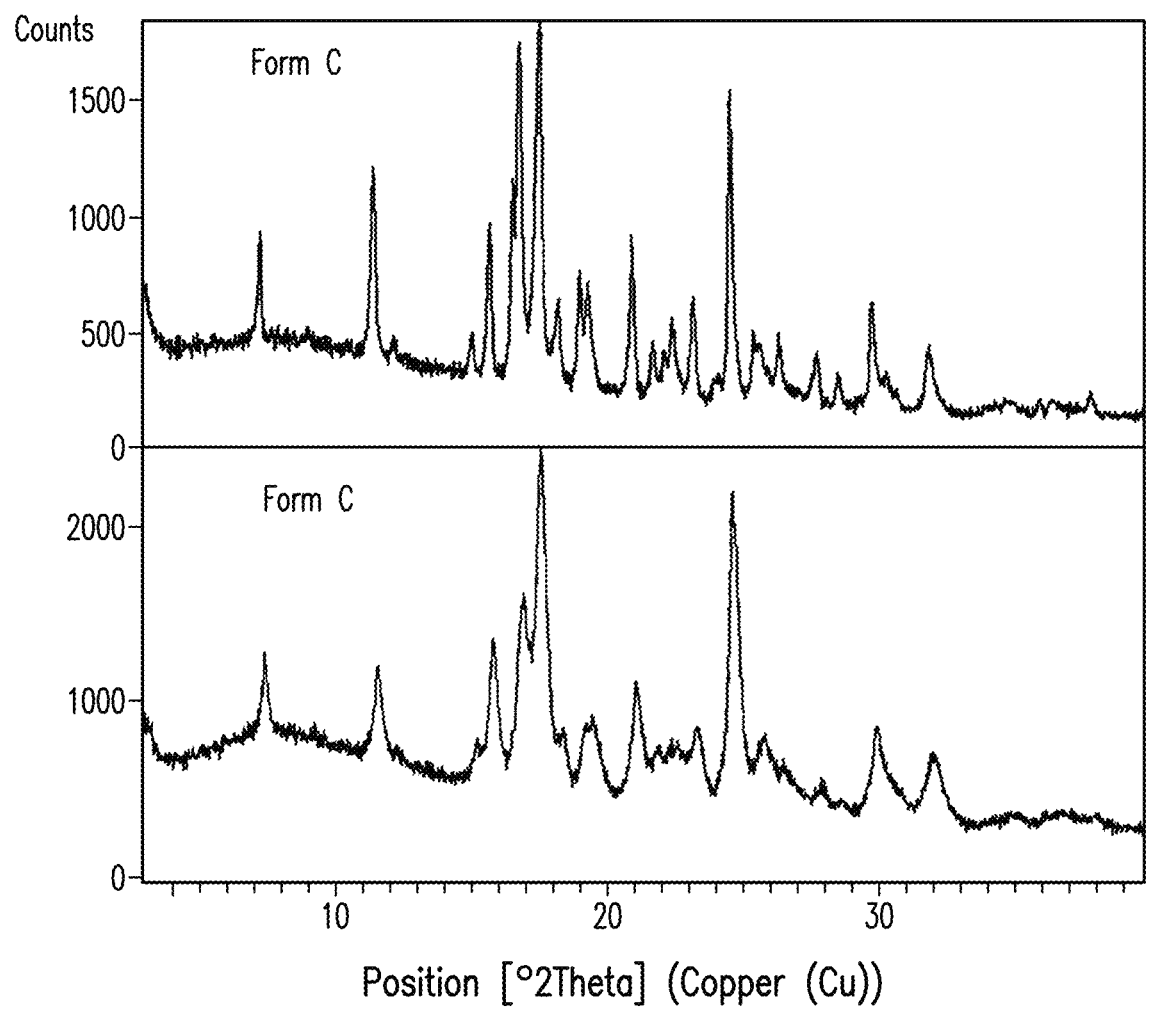

FIG. 22 depicts the comparison of the X-ray powder diffractogram plots of Form C of Compound 1 before (a) and after (b) compression.

Figure 23:
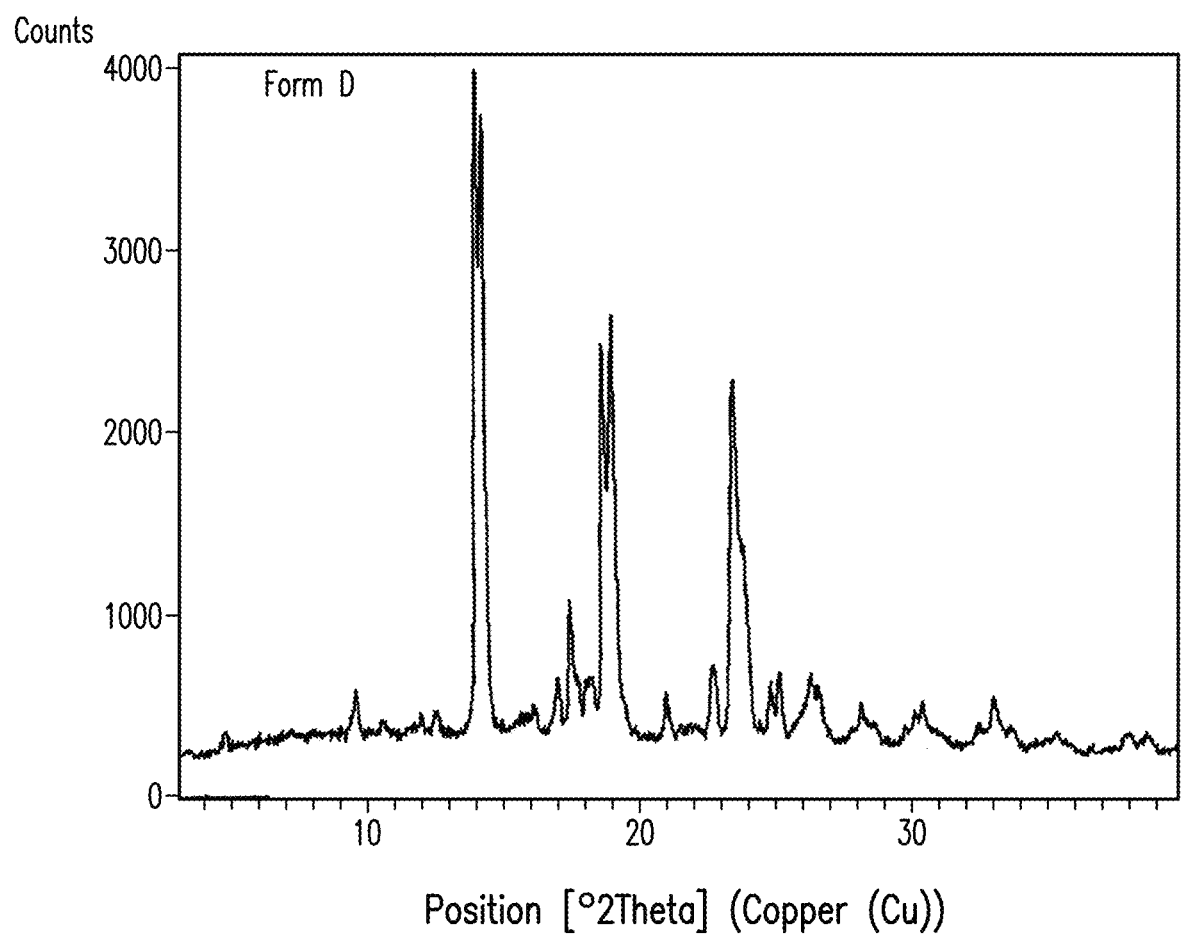

FIG. 23 depicts an XRPD plot of Form D of Compound 1.

Figure 24:
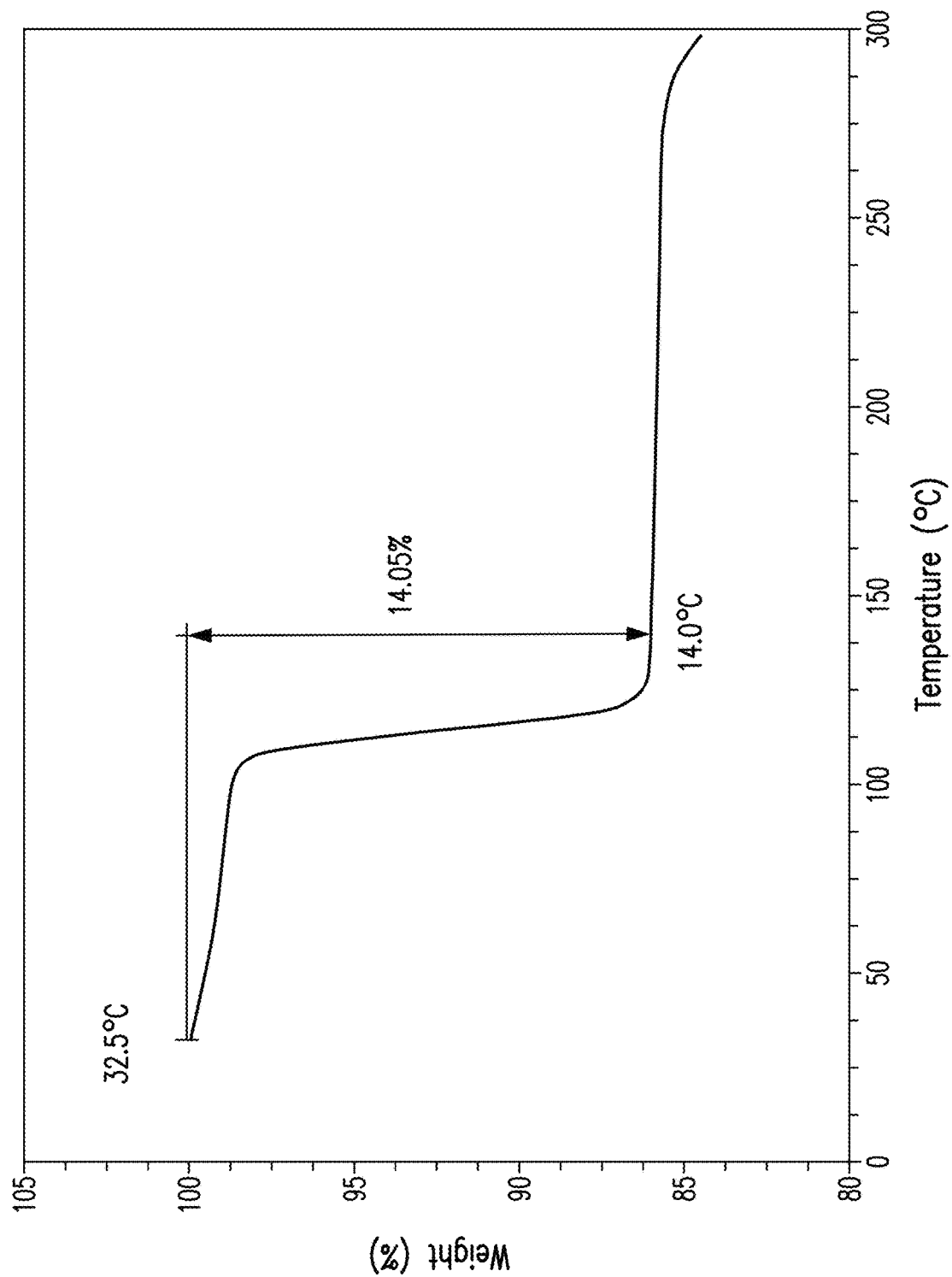

FIG. 24 depicts a TGA thermogram plot of Form D of Compound 1.

Figure 25:
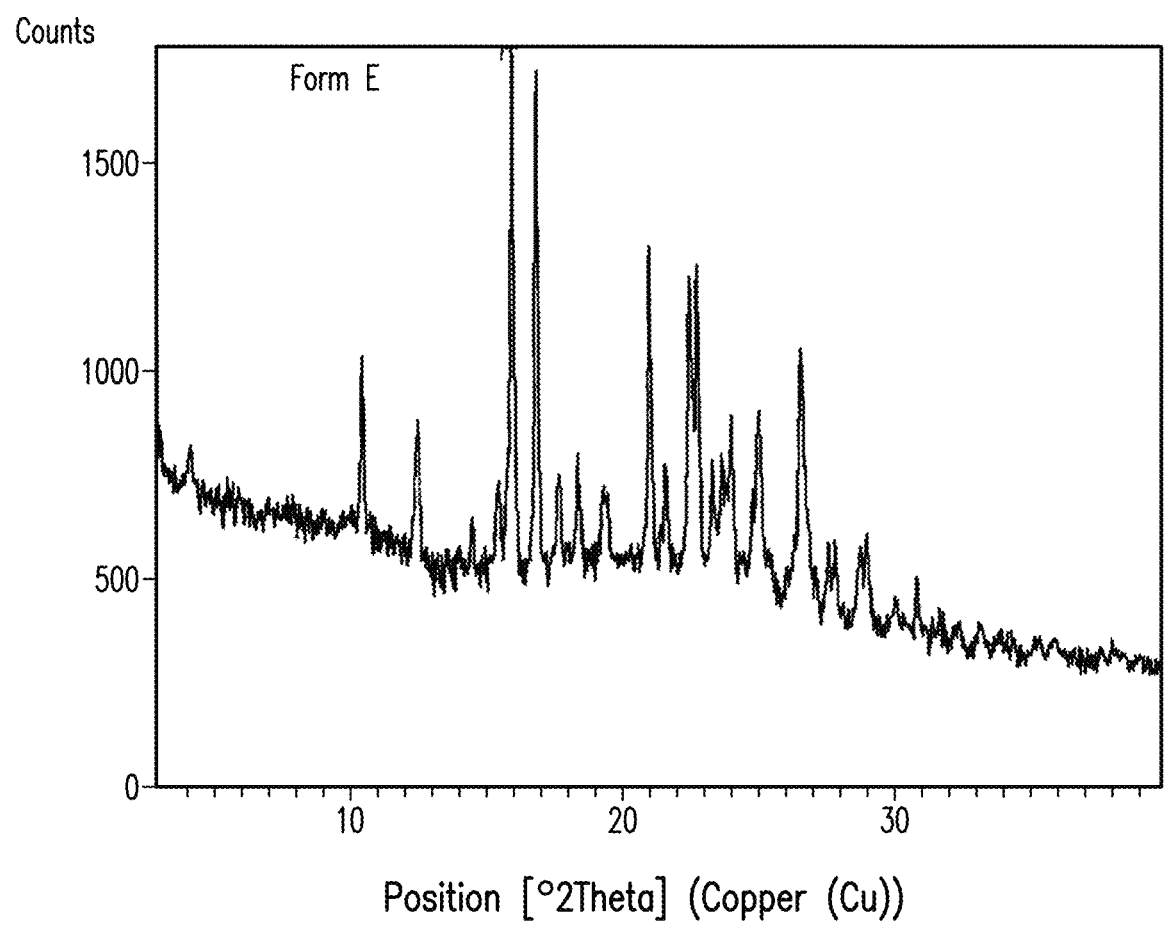

FIG. 25 depicts an XRPD plot of Form E of Compound 1.

Figure 26:
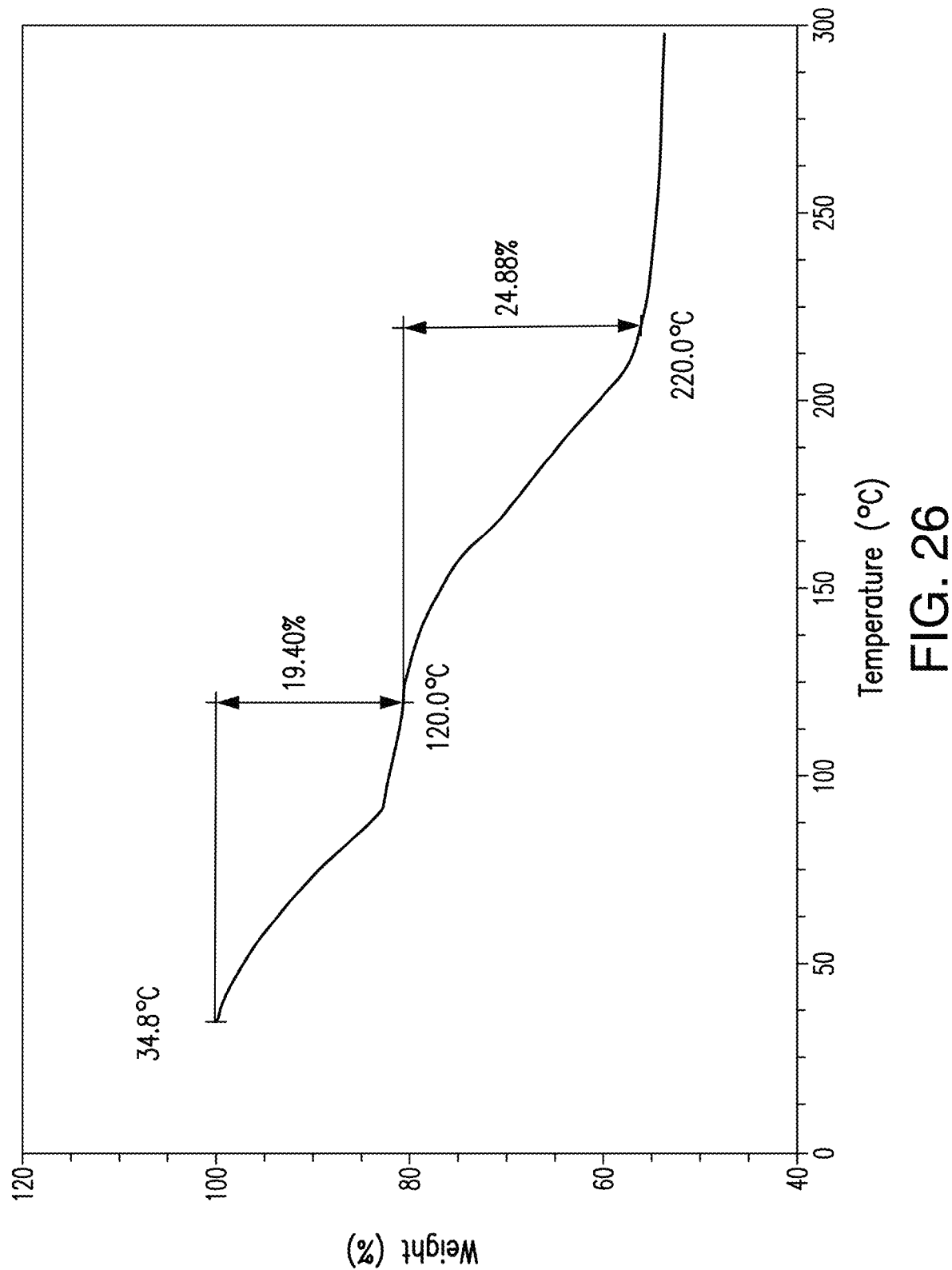

FIG. 26 depicts a TGA thermogram plot of Form E of Compound 1.

Figure 27:
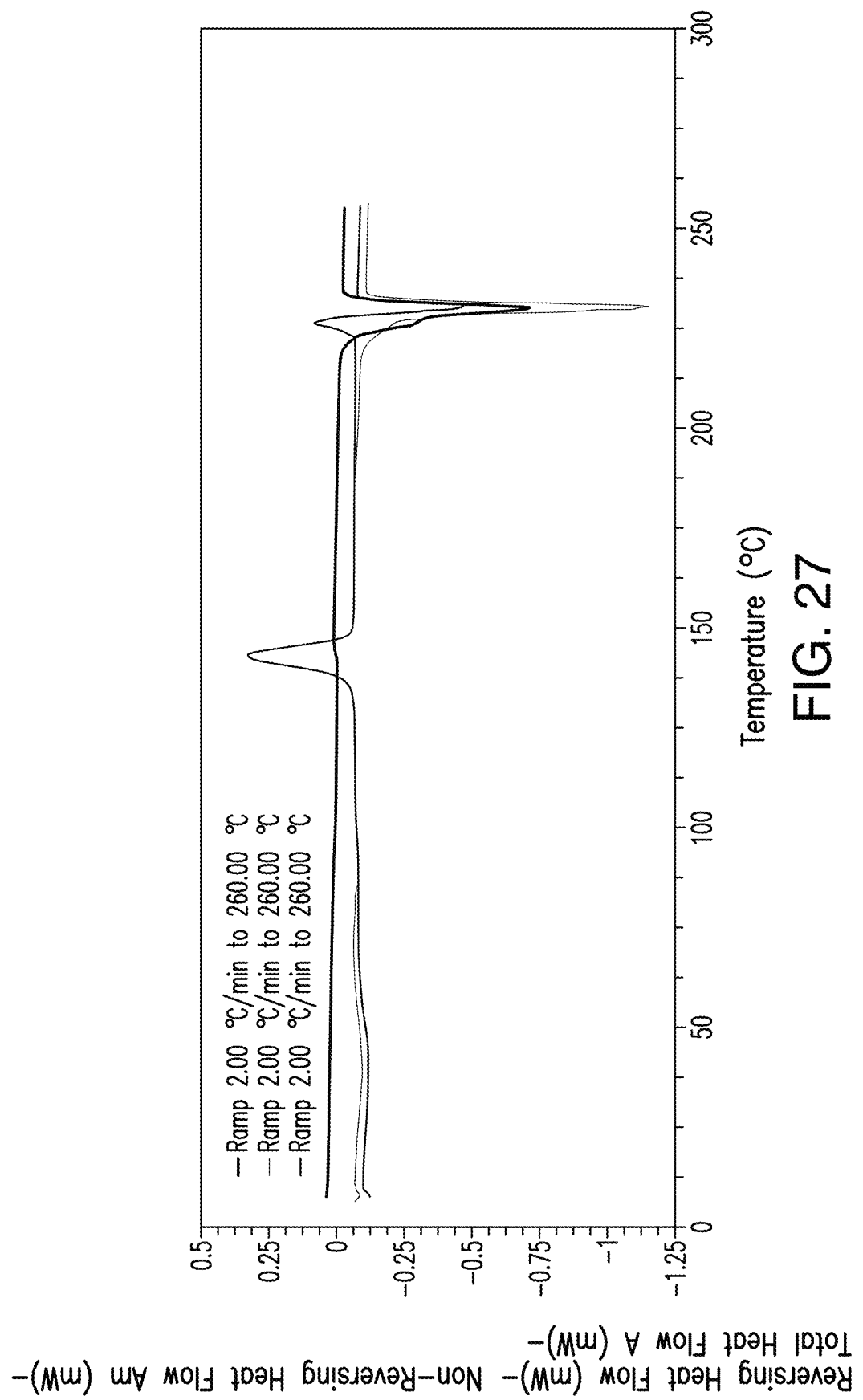

FIG. 27 depicts the modulated DSC thermogramplot of amorphous Compound 1.

Figure 28:
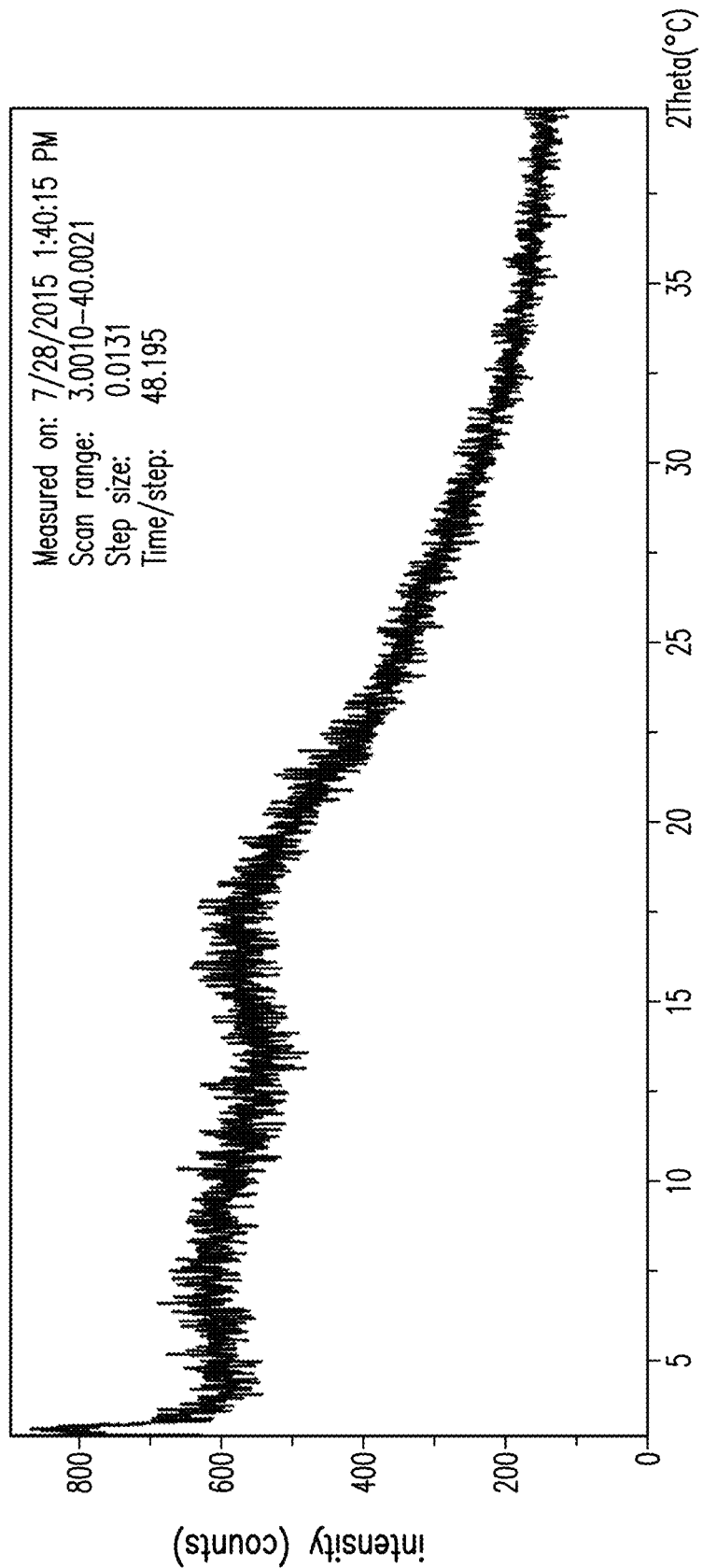

FIG. 28 depicts an XRPD plot of amorphous Compound 1.

Figure 29:
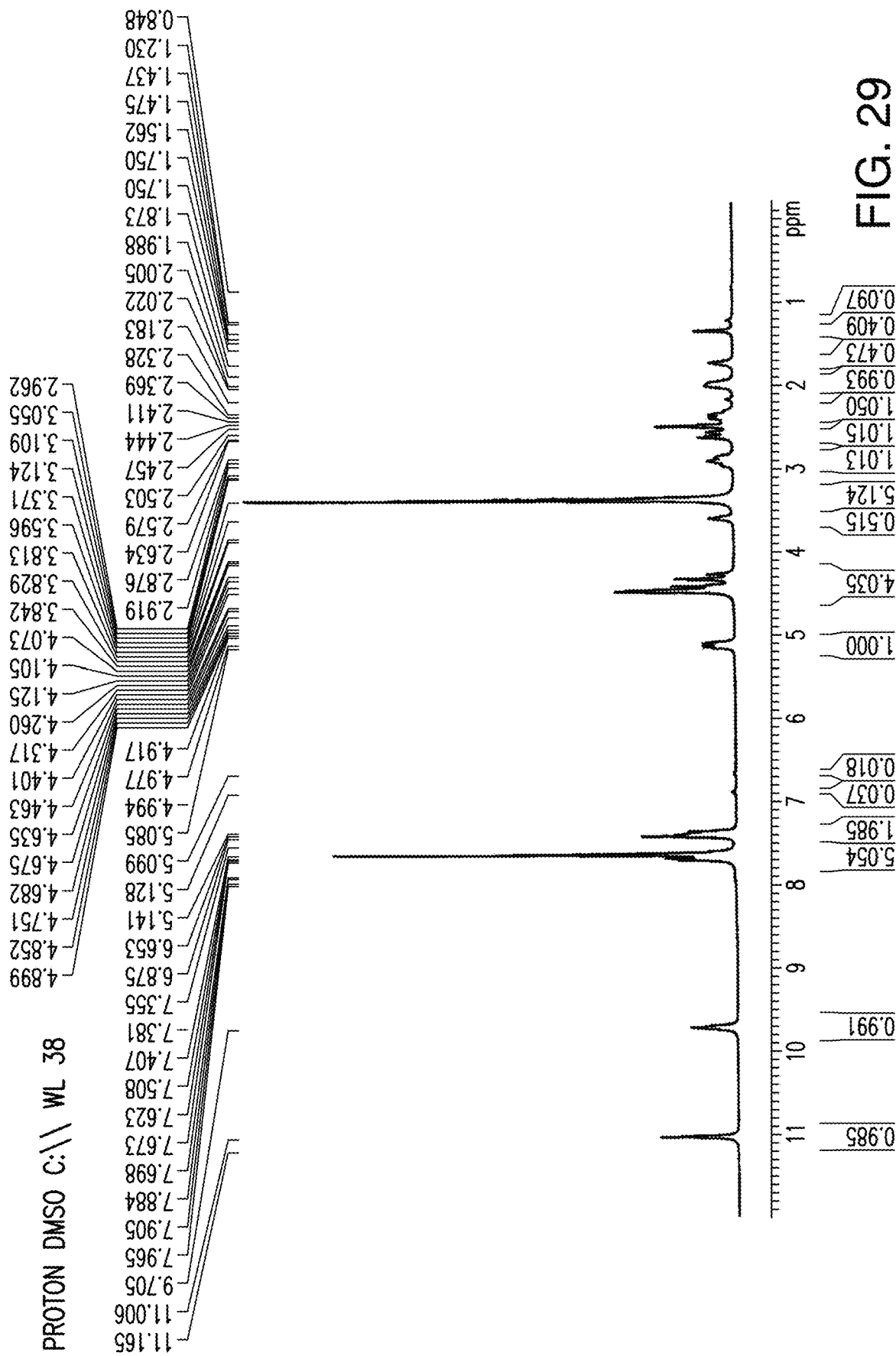

FIG. 29 depicts a $^1$H NMR spectrum of amorphous Compound 1.

Figure 30A:
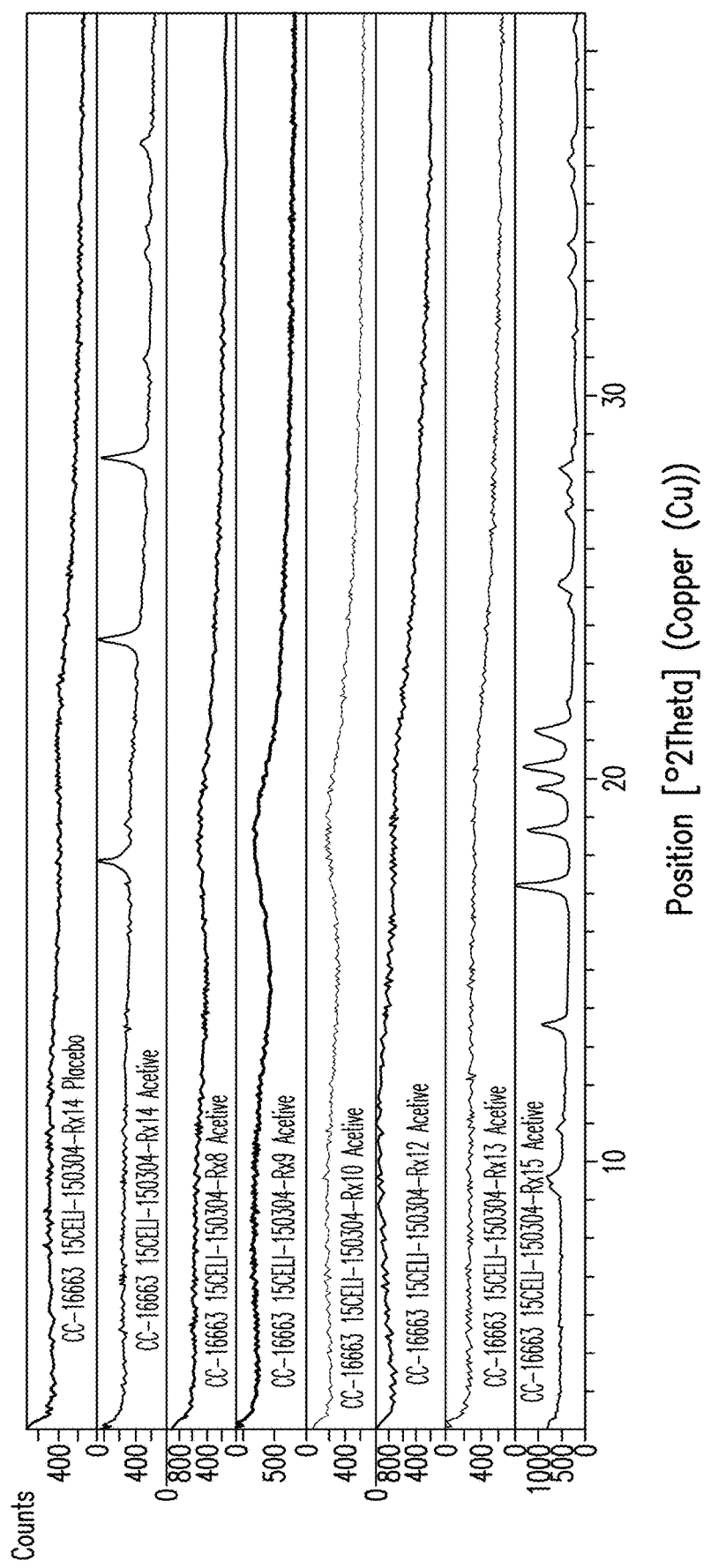
Figure 30B:
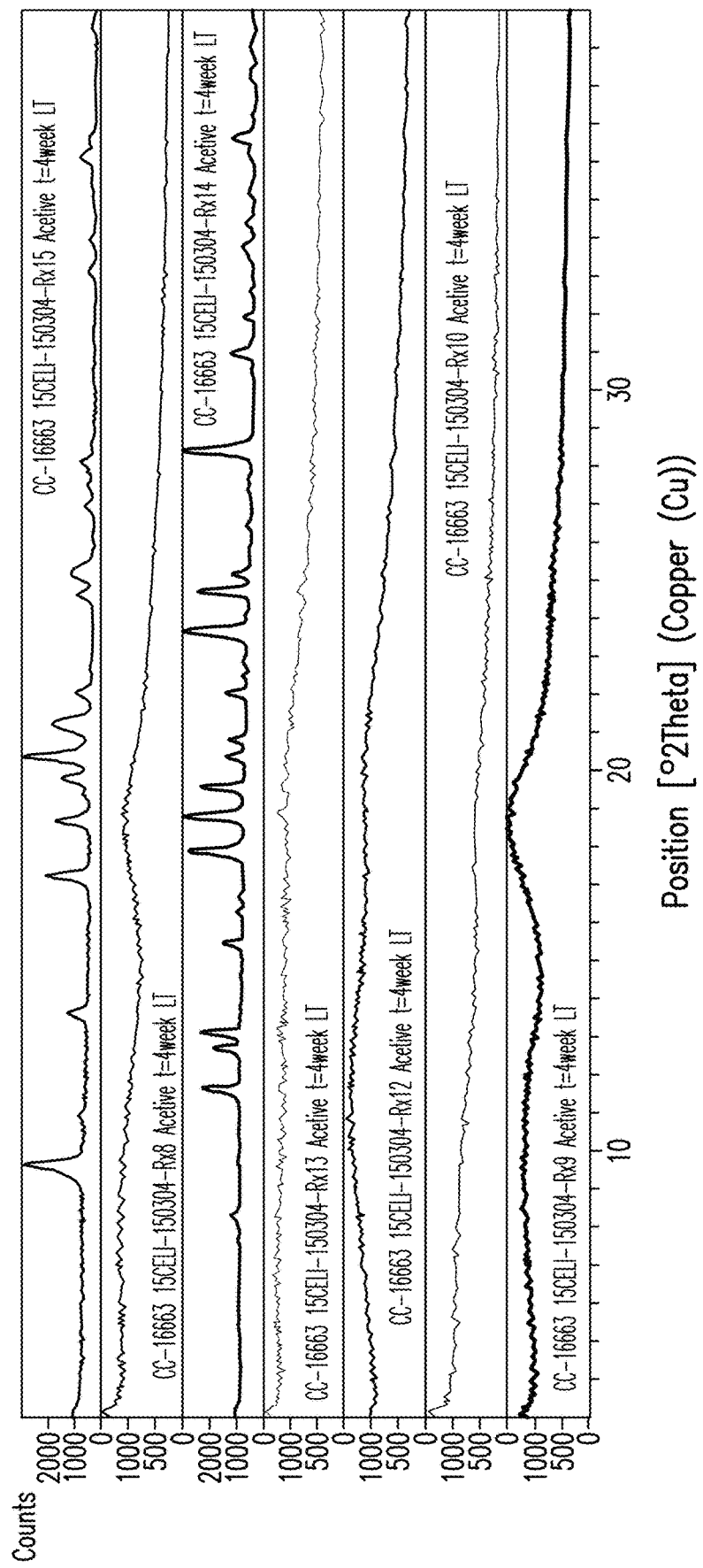
Figure 30C:
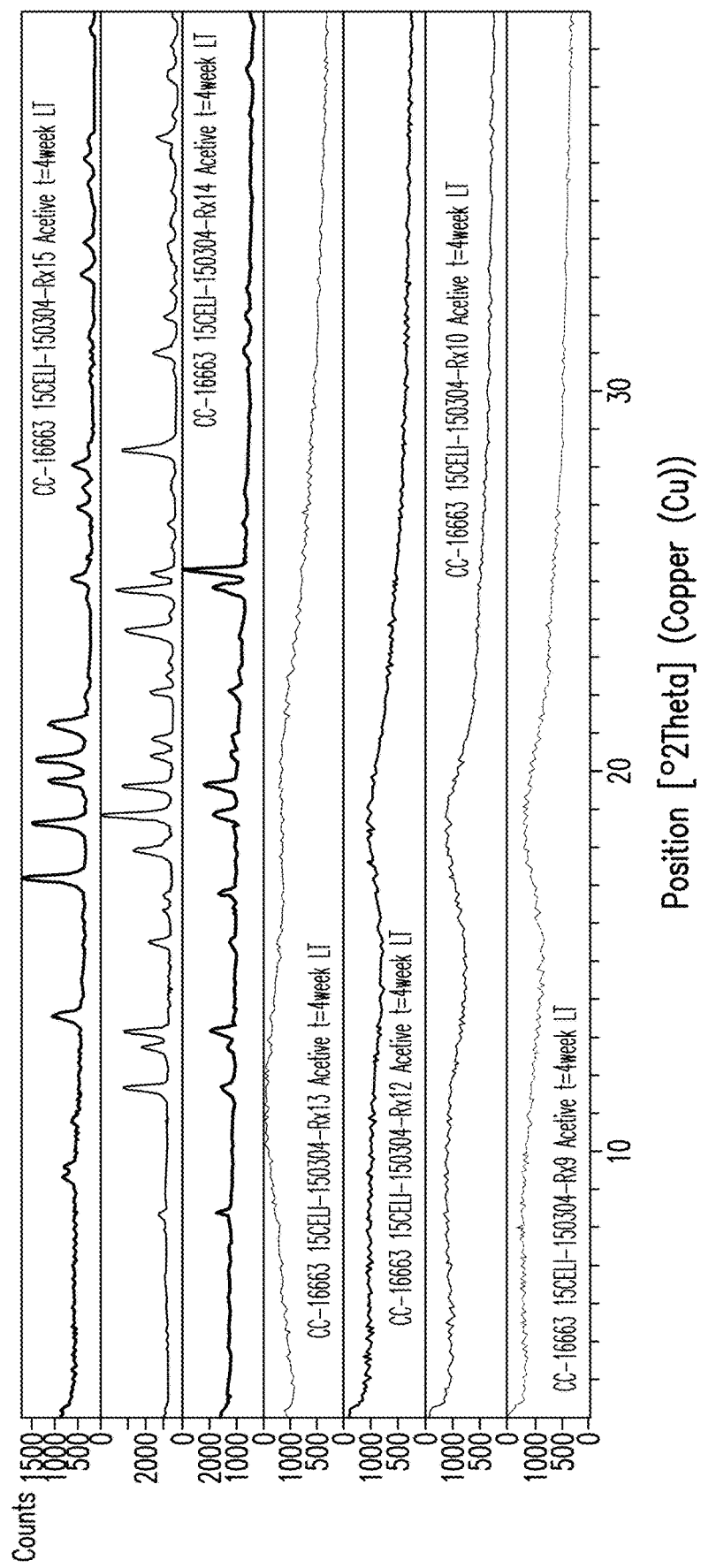

FIGS. 30A, 30B and 30C. Illustrate XRPD profiles of the lyophilized formulations in the second screen.

Figure 31:
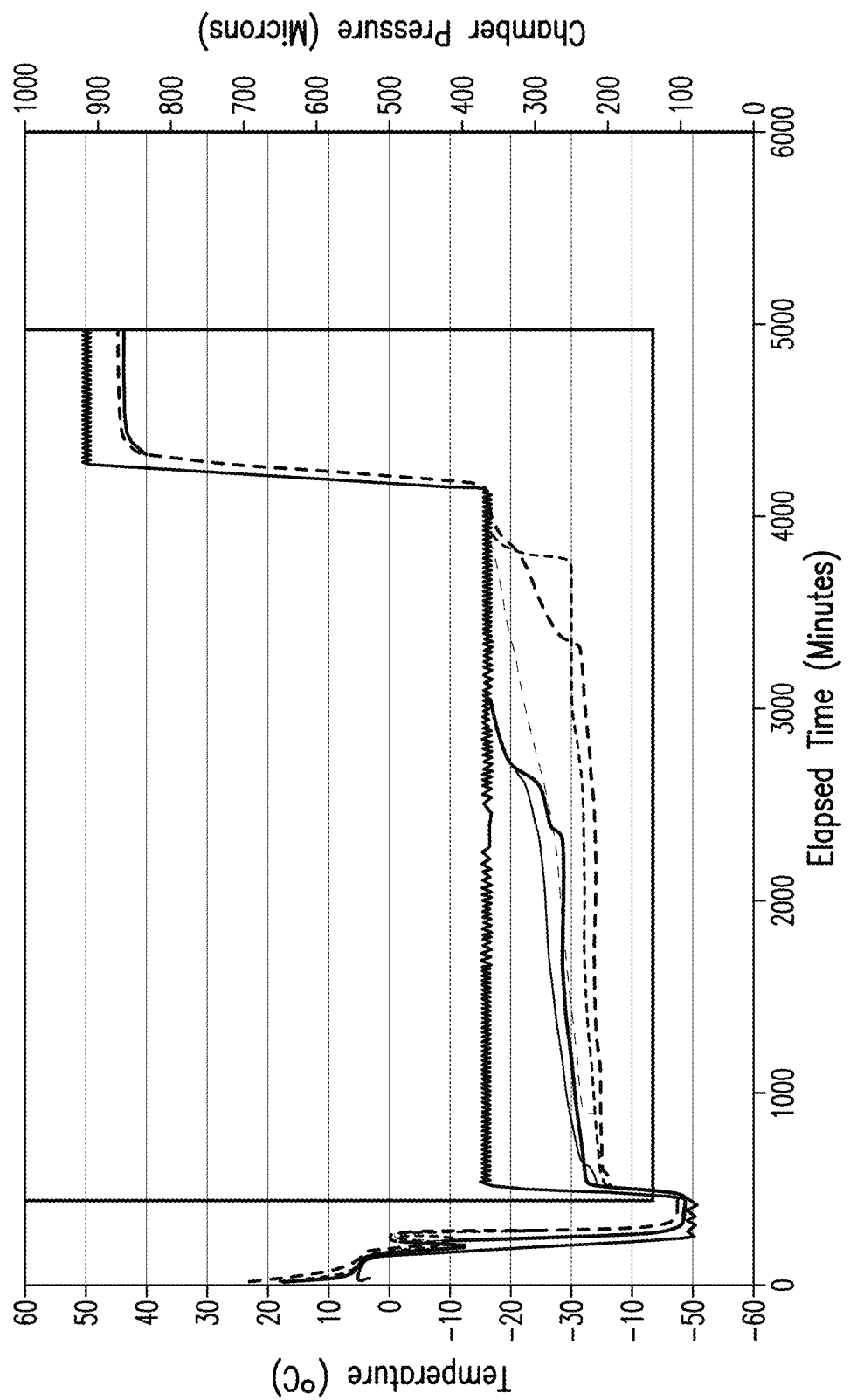

FIG. 31. Illustrates temperature profile of the final lyophilization process.

Figure 32:
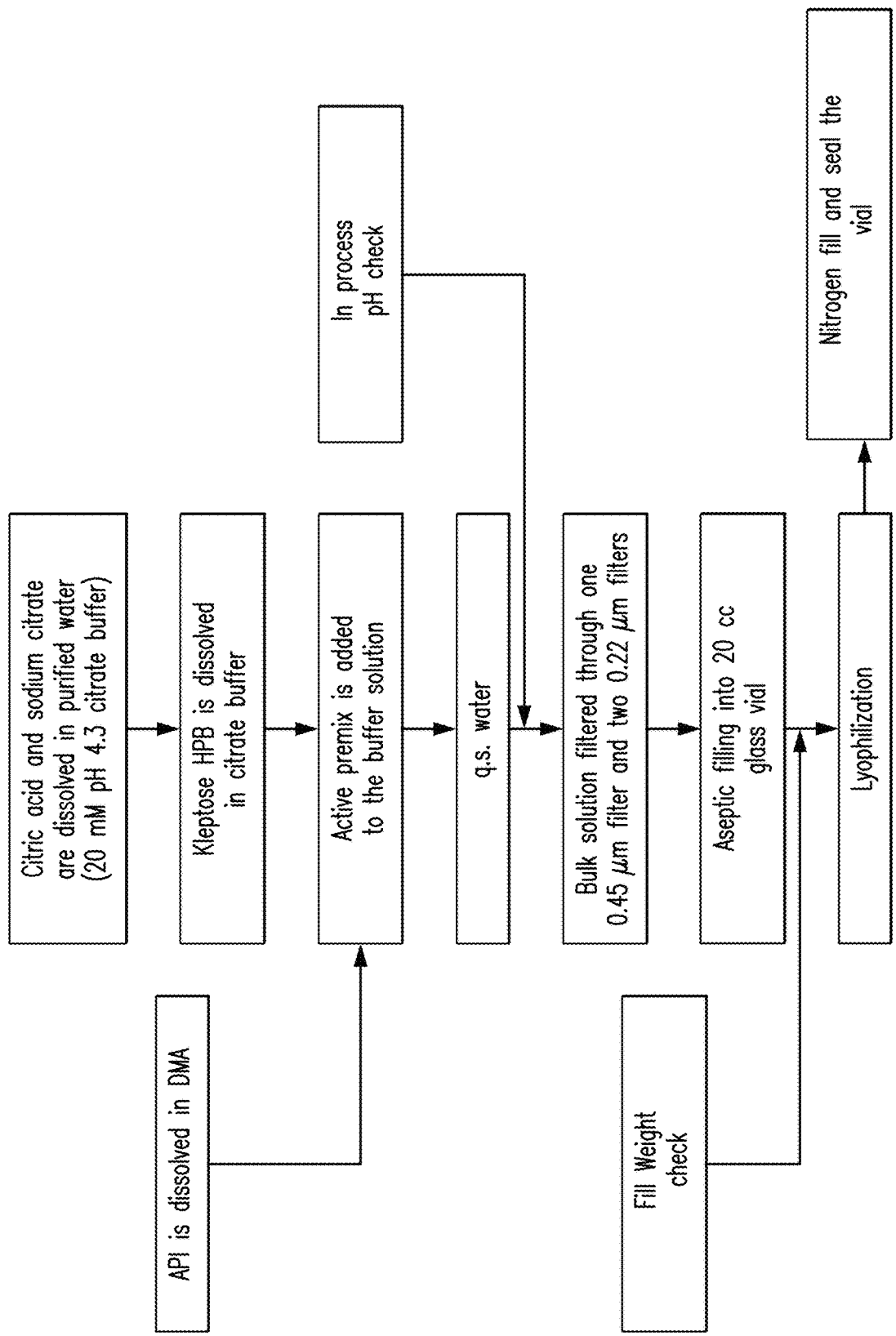

FIG. 32. Illustrates a process diagram of Compound 1 formulation.

6. DETAILED DESCRIPTION

6.1 Definitions

Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs.

The term Compound 1 refers to "2-(4-chlorophenyl)-N-((2-(2,6-dioxopiperidin-3-yl)-1-oxoisoindolin-5-yl)methyl)-2,2-difluoroacetamide" having the structure:

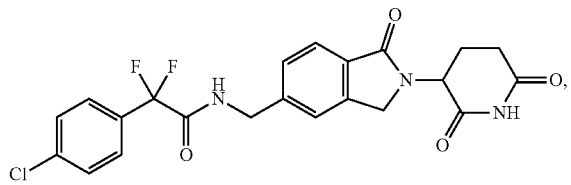 [SMILES: O=C1CCC(N2Cc3cc(CNC(=O)C(F)(F)c4ccc(Cl)cc4)ccc3C2=O)C(=O)N1]

and its stereoisomers or mixture of stereoisomers, pharmaceutically acceptable salts, tautomers, prodrugs, solvates, hydrates, co-crystals, clathrates, or polymorphs thereof. In certain embodiments, Compound 1 refers to 2-(4-chlorophenyl)-N-((2-(2,6-dioxopiperidin-3-yl)-1-oxoisoindolin-5-yl)methyl)-2,2-difluoroacetamide and its tautomers. In certain embodiments, Compound 1 refers to a polymorph of 2-(4-chlorophenyl)-N-((2-(2,6-dioxopiperidin-3-yl)-1-oxoisoindolin-5-yl)methyl)-2,2-difluoroacetamide. In certain embodiments, Compound 1 refers to polymorph Form C of 2-(4-chlorophenyl)-N-((2-(2,6-dioxopiperidin-3-yl)-1-oxoisoindolin-5-yl)methyl)-2,2-difluoroacetamide. In one embodiment, the stereoisomer is an enantiomer.

As used herein, and unless otherwise specified, the term "lyophilize" refers to the process of isolating a solid substance from solution and/or removal of solvent. In some embodiments, this may be achieved by various techniques known to one of skill in the art, including, for example, evaporation (e.g., under vacuum, for example by freeze drying, and/or freezing the solution and vaporizing the frozen solvent under vacuum or reduced pressure conditions, etc.). In some embodiments, the solution contains a cosolvent.

As used herein, the term "cosolvent" refers to a solvent that aids the solubilization of an active agent in water during the manufacturing of a lyophilized formulation provided herein. The cosolvent can be a solvent that also provides sufficient stability of the intermediate formulation during manufacture. The cosolvent can also be removed from the lyophilized formulation, or reduced to an acceptable level, during manufacture. Examples of cosolvents include acetonitrile, chloroform, tert-butanol, dimethylacetamide, methanol, tetrahydrofuran, acetic acid, acetone, anisole, butanol, butyl acetate, tert-butylmethyl ether, ethanol, ethyl acetate, ethyl ether, ethyl formate, heptanes, isobutyl acetate, isopropyl acetate, methyl acetate, 3-methyl-butanol, methylethyl ketone, methylisobutyl ketone, 2-methyl-1-propanol, pentane, 1-pentanol, 1-propanol, 2-propanol, and propyl acetate.

As used herein, and unless otherwise specified, the term "parenteral" includes subcutaneous, intravenous, intramuscular, intra-artricular, intra-synovial, intrasternal, intrathecal, intrahepatic, intralesional and intracranial injection or infusion techniques.

As used herein, and unless otherwise specified, the term "substantially free of" means containing no more than an insignificant amount. In some embodiments, a composition or preparation is "substantially free of" a recited element if it contains less than 5%, 4%, 3%, 2%, or 1%, by weight of the element. In some embodiments, the composition or preparation contains less than 0.9%, 0.8%, 0.7%, 0.6%, 0.5%, 0.4%, 0.3%, 0.2%, 0.1% or less of the recited element. In some embodiments, the composition or preparation contains an undetectable amount of the recited element.

As used herein, "reconstituted aqueous solution" or "reconstituted aqueous composition" or "reconstituted aqueous formulation" refers to an aqueous solution obtained by dissolving a lyophilized composition provided herein in an aqueous solvent.

The term "aqueous diluent" used herein refers to an aqueous liquid capable of being included in a parenteral formulation. Such aqueous diluents can include, for example, saline or dextrose if desired, as well as any of the known ancillary preservatives or excipients commonly found as part of parenteral formulations. Exemplary aqueous diluents include water, 5% dextrose solution, and the like.

As used herein, and unless otherwise specified, the expression "unit dose" refers to a physically discrete unit of a formulation appropriate for a subject to be treated (e.g., for a single dose); each unit containing a predetermined quantity of an active agent selected to produce a desired therapeutic effect (it being understood that multiple doses may be required to achieve a desired or optimum effect), optionally together with a pharmaceutically acceptable carrier, which may be provided in a predetermined amount. The unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may contain a variety of components in addition to the therapeutic agent(s). For example, acceptable carriers (e.g., pharmaceutically acceptable carriers), diluents, stabilizers, buffers, preservatives, etc., may be included as described infra. It will be understood, however, that the total daily usage of a formulation of the present disclosure will be decided by the attending physician within the scope of sound medical judgment. The specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

As used herein, the term "solid form" refers a crystal form or an amorphous form or a mixture thereof of 2-(4-chlorophenyl)-N-((2-(2,6-dioxopiperidin-3-yl)-1-oxoisoindolin-5-yl)methyl)-2,2-difluoroacetamide or a stereoisomer or mixture of stereoisomers, pharmaceutically acceptable salt, tautomer, prodrug, solvate, hydrate, co-crystal, clathrate, or polymorph thereof.

As used herein, unless otherwise specified, the term "pharmaceutically acceptable salt(s)," as used herein includes, but is not limited to, salts of acidic or basic moieties of compounds described herein (e.g., Compound 1). Basic moieties are capable of forming a wide variety of salts with various inorganic and organic acids. The acids that can be used to prepare pharmaceutically acceptable acid addition salts of such basic compounds are those that form non-toxic acid addition salts, e.g., salts containing pharmacologically acceptable anions. Suitable organic acids include, but are not limited to, maleic, fumaric, benzoic, ascorbic, succinic, acetic, formic, oxalic, propionic, tartaric, salicylic, citric, gluconic, lactic, mandelic, cinnamic, oleic, tannic, aspartic, stearic, palmitic, glycolic, glutamic, gluconic, glucaronic, saccharic, isonicotinic, methanesulfonic, ethanesulfonic, p-toluenesulfonic, benzenesulfonic acids, or pamoic (e.g., 1,1'-methylene-bis-(2-hydroxy-3-naphthoate) acids. Suitable inorganic acids include, but are not limited to, hydrochloric, hydrobromic, hydroiodic, sulfuric, phosphoric, or nitric acids. Compounds that include an amine moiety can form pharmaceutically acceptable salts with various amino acids, in addition to the acids mentioned above. Chemical moieties that are acidic in nature are capable of forming base salts with various pharmacologically acceptable cations. Examples of such salts are alkali metal or alkaline earth metal salts and, particularly, calcium, magnesium, sodium, lithium, zinc, potassium, or iron salts.

As used herein, and unless otherwise specified, the term "solvate" means a compound provided herein or a salt thereof that further includes a stoichiometric or non-stoichiometric amount of solvent bound by non-covalent intermolecular forces. Where the solvent is water, the solvate is a hydrate.

As used herein and unless otherwise indicated, the term "prodrug" means a derivative of a compound that can hydrolyze, oxidize, or otherwise react under biological conditions (in-vitro or in-vivo) to provide the compound. Examples of prodrugs include, but are not limited to, derivatives of compounds described herein (e.g., Compound 1) that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds described herein (e.g., Compound 1) that include NO, $NO_2$, ONO, or $ONO_2$ moieties.

A "pharmaceutically acceptable excipient," refers to a substance that aids the administration of an active agent to a subject by for example modifying the stability of an active agent or modifying the absorption by a subject upon administration. A pharmaceutically acceptable excipient typically has no significant adverse toxicological effect on the patient. Examples of pharmaceutically acceptable excipients include, for example, water, NaCl (including salt solutions), normal saline solutions, sucrose, glucose, bulking agents, buffers, binders, fillers, disintegrants, lubricants, coatings, sweeteners, flavors, alcohols, oils, gelatins, carbohydrates such as amylose or starch, fatty acid esters, hydroxymethylcellulose, polyvinyl pyrrolidine, and colors, and the like. One of skill in the art will recognize that other pharmaceutical excipients known in the art are useful in the present invention and include those listed in for example the *Handbook of Pharmaceutical Excipients*, Rowe R. C., Shesky P. J., and Quinn M. E., $6^{th}$ Ed., The Pharmaceutical Press, RPS Publishing (2009). The terms "bulking agent", and "buffer" are used in accordance with the plain and ordinary meaning within the art.

As used herein, "administer" or "administration" refers to the act of physically delivering a substance as it exists outside the body into a subject. Administration includes all forms known in the art for delivering therapeutic agents, including but not limited to topical, mucosal, injections, intradermal, intravenous, intramuscular delivery or other method of physical delivery described herein or known in the art (e.g., implantation of a slow-release device, such as a mini-osmotic pump to a subject; liposomal formulations; buccal; sublingual; palatal; gingival; nasal; vaginal; rectal; intra-arteriole; intraperitoneal; intraventricular; intracranial; or transdermal).

"Anti-cancer agents" refer to anti-metabolites (e.g., 5-fluoro-uracil, methotrexate, fludarabine), antimicrotubule agents (e.g., *vinca* alkaloids such as vincristine, vinblastine; taxanes such as paclitaxel, docetaxel), alkylating agents (e.g., cyclophosphamide, melphalan, carmustine, nitrosoureas such as bischloroethylnitrosurea and hydroxyurea), platinum agents (e.g. cisplatin, carboplatin, oxaliplatin, JM-216 or satraplatin, CI-973), anthracyclines (e.g., doxorubicin, daunorubicin), antitumor antibiotics (e.g., mitomycin, idarubicin, adriamycin, daunomycin), topoisomerase inhibitors (e.g., etoposide, camptothecins), anti-angiogenesis agents (e.g. Sutent® and Bevacizumab) or any other cytotoxic agents, (estramustine phosphate, prednimustine), hormones or hormone agonists, antagonists, partial agonists or partial antagonists, kinase inhibitors, checkpoint inhibitors, and radiation treatment.

By "co-administer" it is meant that a composition described herein is administered at the same time, just prior to, or just after the administration of one or more additional therapeutic compositions, including for example an anti-cancer agent. Co-administration is meant to include simultaneous or sequential administration of compounds individually or in combination (more than one compound or agent). Co-administration includes administering two active agents simultaneously, approximately simultaneously (e.g., within about 1, 5, 10, 15, 20, or 30 minutes of each other), or sequentially in any order. Thus, co-administration can include administering one active agent (e.g. a compound described herein) within 0.5, 1, 2, 4, 6, 8, 10, 12, 16, 20, or 24 hours of a second active agent. Co-administration can also be accomplished by co-formulation, e.g., preparing a single dosage form including both active agents. The active agents can be formulated separately. In such instances, the active agents are admixed and included together in the final form of the dosage unit. Alternatively, co-administration as described herein can include administering two separate unit dosage forms of at least two separate active agents (e.g., Compound 1 and a second active agent described herein).

As used herein, the term "daily" is intended to mean that a therapeutic compound, such as Compound 1, is administered once or more than once each day for a period of time. The term "continuous" is intended to mean that a therapeutic compound, such as Compound 1, is administered daily for an uninterrupted period of at least 10 days to 52 weeks. The term "intermittent" or "intermittently" as used herein is intended to mean stopping and starting at either regular or irregular intervals. For example, intermittent administration of Compound 1 is administration for one to six days per week, administration in cycles (e.g., daily administration for one to ten consecutive days of a 28 day cycle, then a rest period with no administration for rest of the 28 day cycle or daily administration for two to eight consecutive weeks, then a rest period with no administration for up to one week), or administration on alternate days. The term "cycling" as used herein is intended to mean that a therapeutic compound, such as Compound 1, is administered daily or continuously but with a rest period.

An "effective amount" is an amount sufficient to achieve the effect for which it is administered (e.g., treat a disease or reduce one or more symptoms of a disease or condition). Thus, administration of an "amount" of a compound described herein to a subject refers to administration of "an amount effective," to achieve the desired therapeutic result. A "therapeutically effective amount" of a compound described herein for purposes herein is thus determined by such considerations as are known in the art. The term "therapeutically effective amount" of a composition described herein refers to the amount of the composition that, when administered, is sufficient to treat one or more of the symptoms of a disease described herein (e.g., AML). Administration of a compound described herein can be determined according to factors such as, for example, the disease state, age, sex, and weight of the individual. A therapeutically effective amount also refers to any toxic or detrimental effects of Compound 1 are outweighed by the therapeutically beneficial effects.

As used herein the terms "treat," "treating" and "treatment" contemplate an action that occurs while a subject is suspected, diagnosed or suffering from a disease described herein (e.g., leukemia, including AML or MDS), which reduces the severity or symptoms of the disease, or retards or slows the progression or symptoms of the disease.

The terms "subject," "patient," "subject in need thereof," and "patient in need thereof" are herein used interchangeably and refer to a living organism suffering from one or more of the diseases described herein (e.g., AML or MDS) that can be treated by administration of a composition described herein. Non-limiting examples of organisms include humans, other mammals, bovines, rats, mice, dogs, monkeys, goat, sheep, cows, deer, and other non-mammalian animals. In embodiments, a subject is human. A human subject can be between the ages of about 1 year old to about 100 years old. In embodiments, subjects herein can be characterized by the disease being treated (e.g., a "AML subject", a "cancer subject", an "MDS subject" or a "leukemia subject").

As used herein, and unless otherwise specified, the terms "prevent," "preventing" and "prevention" refer to the prevention of the onset, recurrence or spread of a disease or disorder, or of one or more symptoms thereof. The terms "prevent," "preventing" and "prevention" contemplate an action that occurs before a patient begins to suffer from the specified disease or disorder or symptoms thereof, which inhibits or reduces the severity of the disease or disorder.

As used herein, and unless otherwise indicated, the terms "manage," "managing" and "management" encompass preventing the recurrence of the specified disease or disorder in a patient who has already suffered from the disease or disorder, or lengthening the time that a patient who has suffered from the disease or disorder remains in remission. The terms encompass modulating the threshold, development or duration of the disease or disorder, or changing the way that a patient responds to the disease or disorder.

As used herein, and unless otherwise specified, the term "about," when used in connection with doses, amounts, or weight percent of ingredients of a composition or a dosage form, means dose, amount, or weight percent that is recognized by those of ordinary skill in the art to provide a pharmacological effect equivalent to that obtained from the specified dose, amount, or weight percent is encompassed. Specifically, the term "about" contemplates a dose, amount, or weight percent within 30%, 25%, 20%, 15%, 10%, or 5% of the specified dose, amount, or weight percent is encompassed.

As used herein, and unless otherwise specified, the term "stable," when used in connection with a formulation or a dosage form, means that the active ingredient of the formulation or dosage form remains solubilized for a specified amount of time and does not significantly degrade or aggregate or become otherwise modified (e.g., as determined, for example, by HPLC). In some embodiments, about 70% or greater, about 80% or greater or about 90% or greater of the compound remains solubilized after the specified period. Stability can also refer to the compatibility of pharmaceutically acceptable excipients described herein. Accordingly, a dosage form can be considered stable when the combined pharmaceutically acceptable excipients and active agent(s) described herein do not degrade or otherwise modify (e.g., react with) the effectiveness or therapeutic value of an active agent described herein.

As used herein, the term "tumor," refers to all neoplastic cell growth and proliferation, whether malignant or benign, and all pre-cancerous and cancerous cells and tissues. "Neoplastic," as used herein, refers to any form of dysregulated or unregulated cell growth, whether malignant or benign, resulting in abnormal tissue growth. Thus, "neoplastic cells" include malignant and benign cells having dysregulated or unregulated cell growth.

As used herein, "hematologic malignancy" refers to cancer of the body's blood-forming and immune system—the bone marrow and lymphatic tissue. Such cancers include leukemias, lymphomas (Non-Hodgkin's Lymphoma), Hodgkin's disease (also called Hodgkin's Lymphoma), myelodysplastic syndrome (MDS), and myeloma. In one embodiment, the myeloma is multiple myeloma. In some embodiments, the leukemia is, for example, acute myelogenous leukemia (AML), acute lymphocytic leukemia (ALL), adult T-cell leukemia, chronic lymphocytic leukemia (CLL), hairy cell leukemia, myelodysplasia, myeloproliferative disorders, chronic myelogenous leukemia (CML), myelodysplastic syndrome (MDS), human lymphotrophic virus-type 1 (HTLV-1) leukemia, mastocytosis, or B-cell acute lymphoblastic leukemia. In some embodiments, the lymphoma is, for example, diffuse large B-cell lymphoma (DLBCL), B-cell immunoblastic lymphoma, small non-cleaved cell lymphoma, human lymphotrophic virus-type 1 (HTLV-1) leukemia/lymphoma, adult T-cell lymphoma, peripheral T-cell lymphoma (PTCL), cutaneous T-cell lymphoma (CTCL), mantle cell lymphoma (MCL), Hodgkin lymphoma (HL), non-Hodgkin lymphoma (NHL), AIDS-related lymphoma, follicular lymphoma, small lymphocytic lymphoma, T-cell/histiocyte rich large B-cell lymphoma, transformed lymphoma, primary mediastinal (thymic) large B-cell lymphoma, splenic marginal zone lymphoma, Richter's transformation, nodal marginal zone lymphoma, or ALK-positive large B-cell lymphoma. In one embodiment, the hematological cancer is indolent lymphoma including, for example, DLBCL, follicular lymphoma, or marginal zone lymphoma.

The term "leukemia" refers to malignant neoplasms of the blood-forming tissues. The leukemia includes, but is not limited to, chronic lymphocytic leukemia, chronic myelocytic leukemia, acute lymphoblastic leukemia, acute myeloid leukemia, and acute myeloblastic leukemia. The leukemia can be relapsed, refractory or resistant to conventional therapy.

The term "myelodysplastic syndrome" refers to hematological conditions characterized by abnormalities in the production of one or more of the cellular components of blood (red cells, white cells (other than lymphocytes) and platelets (or their progenitor cells, megakaryocytes)), and includes the following disorders: refractory anemia (RA); RA with ringed sideroblasts (RARS); RA with excess of blasts (RAEB); refractory cytopenia with multilineage dysplasia (RCMD), refractory cytopenia with unilineage dysplasia (RCUD); unclassifiable myelodysplastic syndrome (MDS-U), myelodysplastic syndrome associated with an isolated del(5q) chromosome abnormality, therapy-related myeloid neoplasms and chronic myelomonocytic leukemia (CMML).

As used herein, "promyelocytic leukemia" or "acute promyelocytic leukemia" refers to a malignancy of the bone marrow in which there is a deficiency of mature blood cells in the myeloid line of cells and an excess of immature cells called promyelocytes. It is usually marked by an exchange of regions of chromosomes 15 and 17.

As used herein, "acute lymphocytic leukemia (ALL)", also known as "acute lymphoblastic leukemia" refers to a malignant disease caused by the abnormal growth and development of early nongranular white blood cells, or lymphocytes.

As used herein, "T-cell leukemia" refers to a disease in which certain cells of the lymphoid system called T lymphocytes or T cells are malignant. T cells are white blood cells that normally can attack virus-infected cells, foreign cells, and cancer cells and produce substances that regulate the immune response.

The term "relapsed" refers to a situation where patients who have had a remission of cancer after therapy have a return of cancer cells in the marrow and/or a decrease in normal blood cells.

The term "refractory or resistant" refers to a circumstance where patients, even after intensive treatment, have residual cancer cells, for example in their marrow.

As used herein, overall survival (OS) means the time from randomization in a clinical trial until death from any cause. As used herein, progression-free survival (PFS) means the time from randomization in a clinical trial until progression or death. As used herein, event-free survival (EFS) means the time from study entry until any treatment failure, including disease progression, treatment discontinuation for any reason, or death. As used herein, overall response rate (ORR) means the sum of the percentage of patients who achieve complete and partial responses. As used herein, duration of response (DoR) is the time from achieving a response until relapse or disease progression.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. 1972, 11:942-944).

6.2 Polymorphs of 2-(4-chlorophenyl)-N-((2-(2,6-dioxopiperidin-3-yl)-1-oxoisoindolin-5-yl)methyl)-2,2-difluoroacetamide In one embodiment, Compound 1 is polymorph Form A, Form B, Form C, Form D, Form E or an amorphous form of 2-(4-chlorophenyl)-N-((2-(2,6-dioxopiperidin-3-yl)-1-oxoisoindolin-5-yl)methyl)-2,2-difluoroacetamide. Polymorphs of 2-(4-chlorophenyl)-N-((2-(2,6-dioxopiperidin-3-yl)-1-oxoisoindolin-5-yl)methyl)-2,2-difluoroacetamide are described in a U.S. provisional patent application filed concurrently herewith entitled SOLID FORMS OF 2-(4-CHLOROPHENYL)-N-((2-(2,6-DIOXOPIPERIDIN-3-YL)-1-OXOISOINDOLIN-5-YL)METHYL)-2,2-DIFLUOROACETAMIDE, AND THEIR PHARMACEUTICAL COMPOSITIONS AND USES", the disclosure of which is incorporated herein by reference in its entirety. Polymorphs of 2-(4-chlorophenyl)-N-((2-(2,6-dioxopiperidin-3-yl)-1-oxoisoindolin-5-yl)methyl)-2,2-difluoroacetamide are briefly described herein.

Form A of 2-(4-chlorophenyl)-N-((2-(2,6-dioxopiperidin-3-yl)-1-oxoisoindolin-5-yl)methyl)-2,2-difluoroacetamide In certain embodiments, the lyophilized formulations provided herein are prepared from Form A of Compound 1.

In one embodiment, Form A is an anhydrous form of Compound 1. In another embodiment, Form A of Compound 1 is crystalline.

In certain embodiments, Form A is obtained by crystallization from certain solvent systems, for example, solvent systems comprising one or more of the following solvents: acetone and the solvent mixture of isopropanol and water at room temperature. In certain embodiments, Form A is obtained as an intermediate solid form from slurries at elevated temperature, for example about 50° C., in ethanol/water (1:1), acetone or acetonitrile.

In certain embodiments, Form A is substantially crystalline, as indicated by, e.g., X-ray powder diffraction measurements. In one embodiment, Form A of Compound 1 has an X-ray powder diffraction pattern substantially as shown in FIG. 2.

Figure 1:
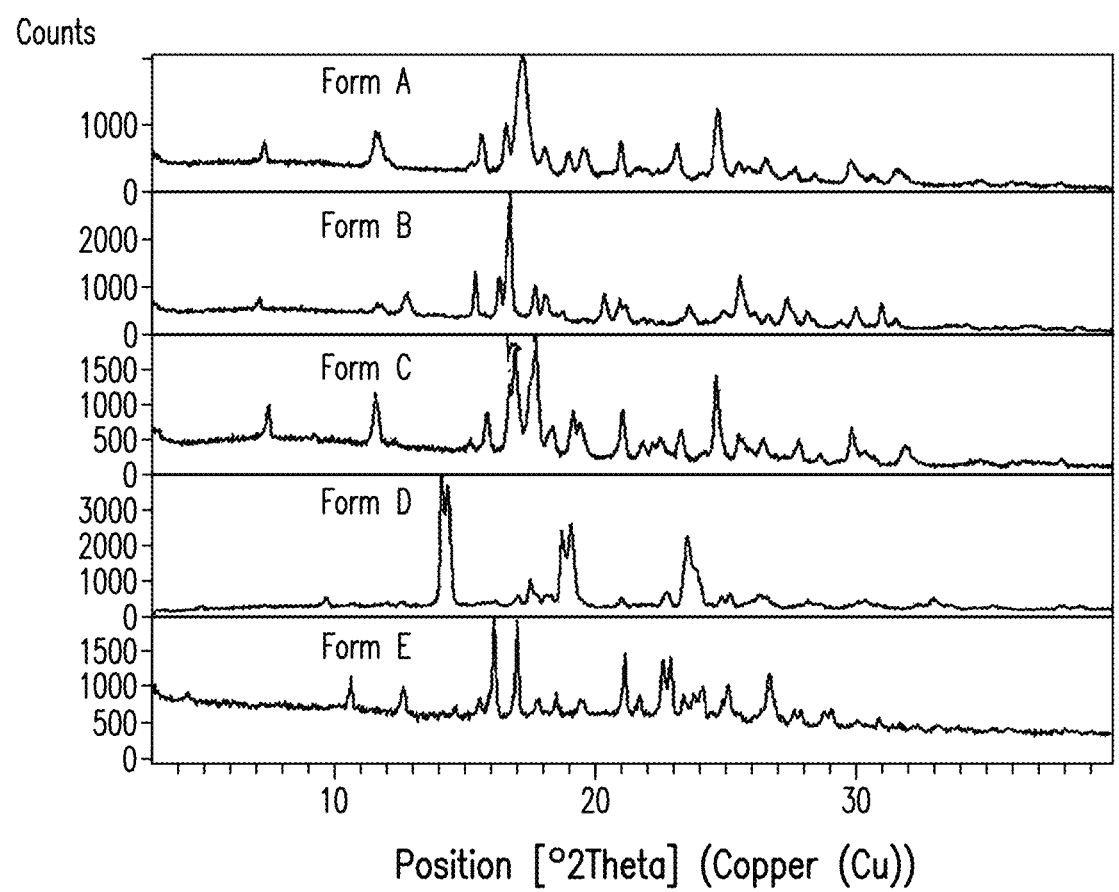
FIG. 1 depicts an X-ray powder diffractogram stack plot of Forms A, B, C, D, and E of Compound 1.
Figure 2:
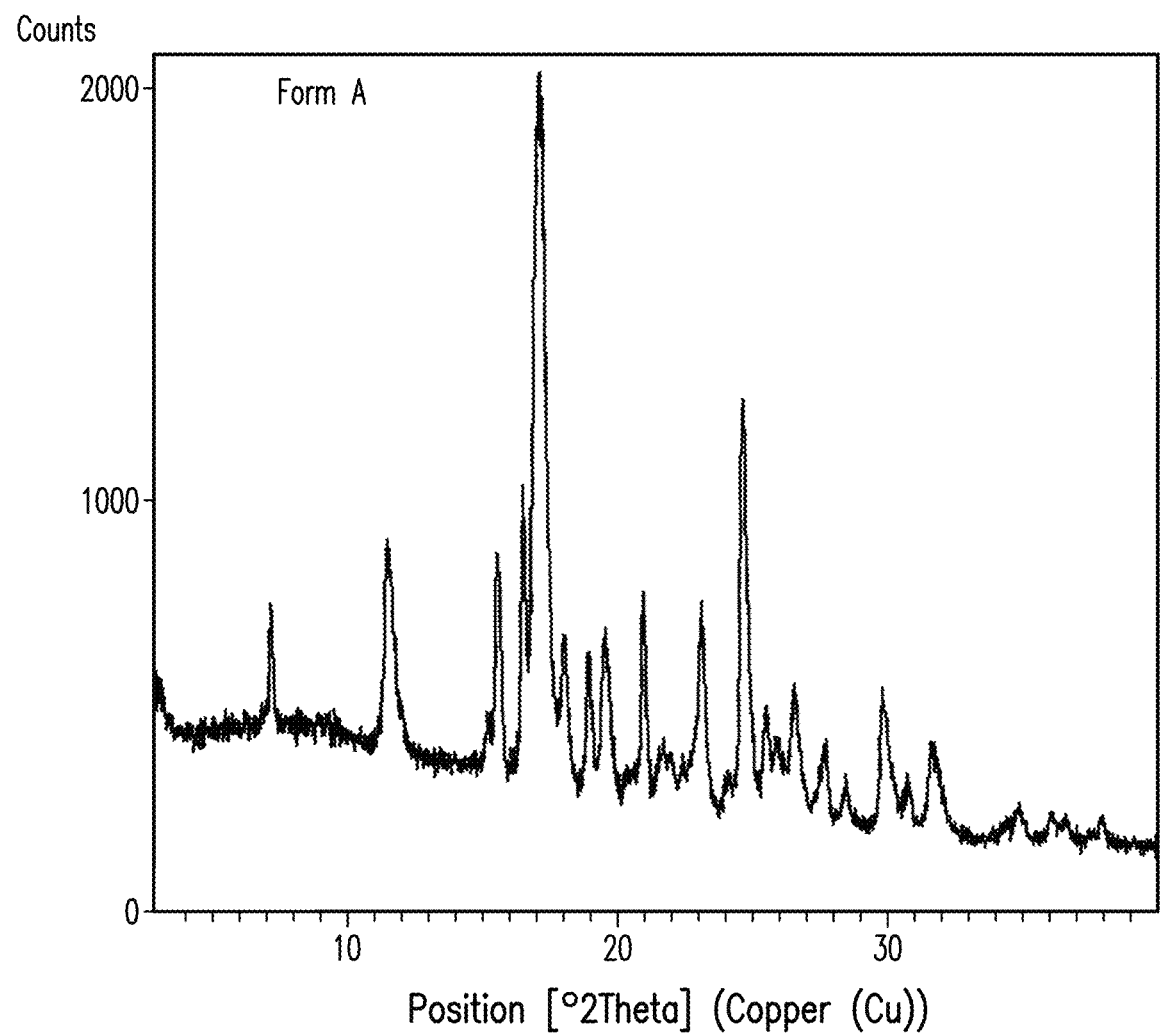
FIG. 2 depicts an X-ray powder diffractogram (XRPD) plot of Form A of Compound 1.

In one embodiment, Form A of Compound 1 has one or more characteristic X-ray powder diffraction peaks at a two-theta angle of approximately 11.5, 15.6, 16.6, 17.2, 18.1, 19.0, 19.6, 21.1, 23.2 or 24.8 degrees 2θ as depicted in FIG. 2. In another embodiment, Form A of Compound 1 has one, two, three or four characteristic X-ray powder diffraction peaks at a two-theta angle of approximately 15.6, 16.6, 17.2 or 24.8 degrees 2θ. In another embodiment, Form A of Compound 1 has one, two, three, four, five, six or seven characteristic X-ray powder diffraction peaks as set forth in Table 1. In another embodiment, Form A of Compound 1 has one, two, or three characteristic X-ray powder diffraction peaks as set forth in Table 1.

Figure 3:
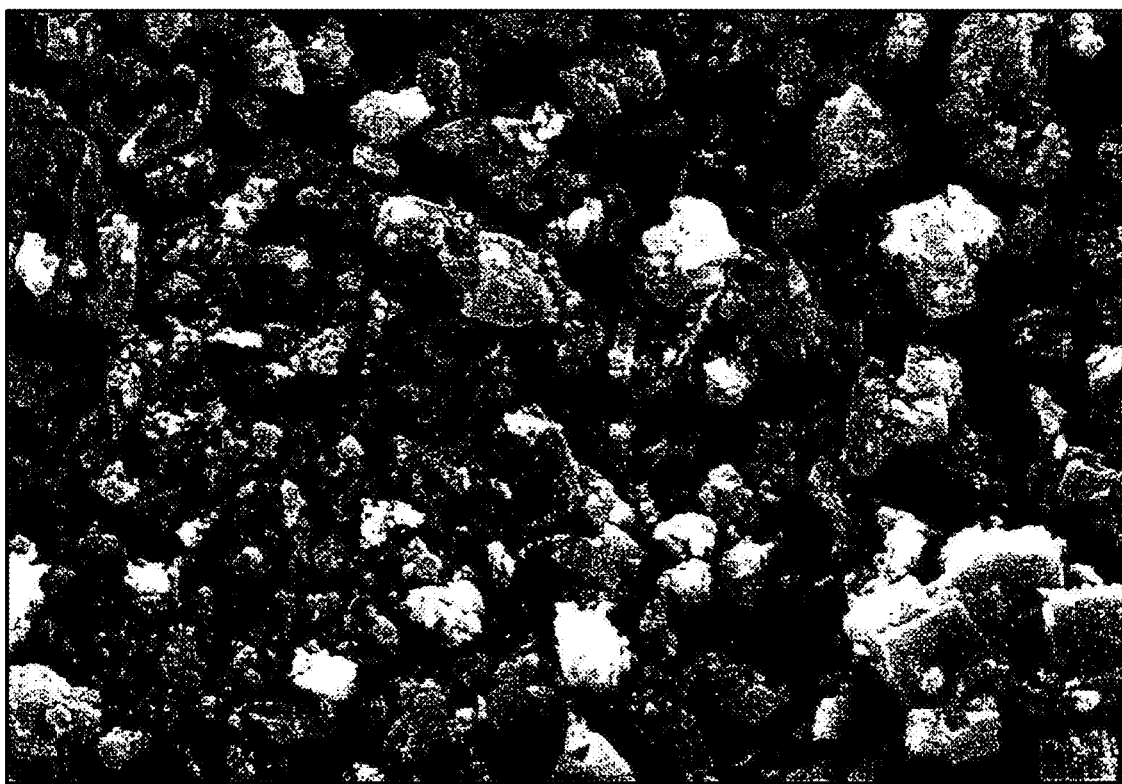
FIG. 3 depicts a SEM image of Form A of Compound 1.

In one embodiment, Form A of Compound 1 has the SEM picture as shown in FIG. 3.

Figure 4:
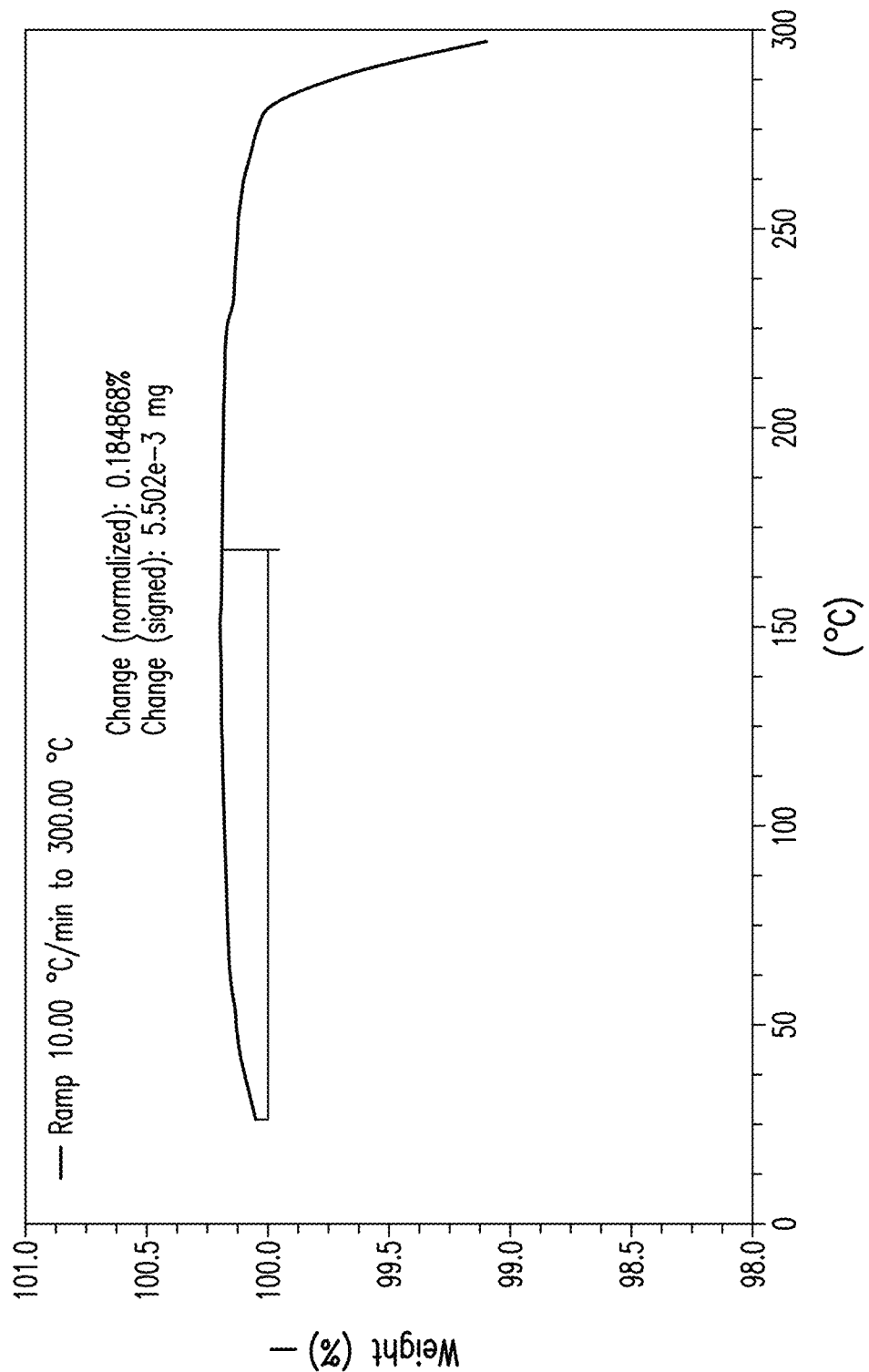
FIG. 4 depicts a thermogravimetrical analysis (TGA) plot of Form A of Compound 1.

In one embodiment, the crystalline form of Compound 1 has a thermogravimetric (TGA) thermograph corresponding substantially to the representative TGA thermogram as depicted in FIG. 4. In certain embodiments, no TGA weight loss is observed for Form A.

Figure 5:
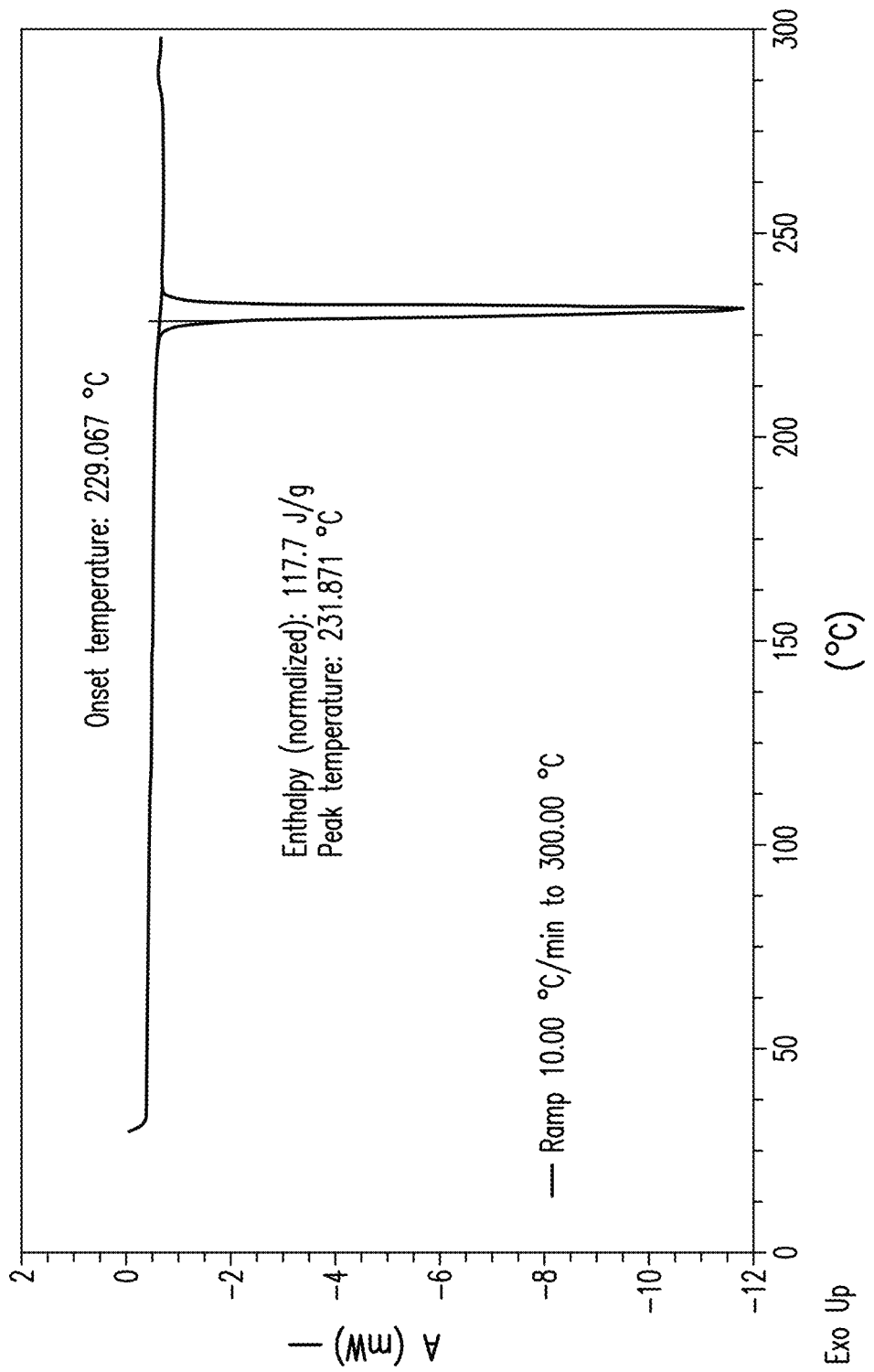
FIG. 5 depicts a differential scanning calorimetry (DSC) thermogram plot of Form A of Compound 1.

In one embodiment, crystalline form A of Compound 1 has a DSC thermogram corresponding substantially as depicted in FIG. 5. In certain embodiments, Form A is characterized by a DSC plot comprising a melting event with an onset temperature of 229° C. and heat of fusion of 118 J/g.

In certain embodiments, Form A is characterized by dynamic vapor sorption analysis. A representative dynamic vapor sorption (DVS) isotherm plot is shown in FIG. 6. In certain embodiments, when the relative humidity ("RH") is increased from about 0% to about 90% RH, Form A exhibits less than 1.5%, less than 1.2% or about 1.2% w/w water uptake. In certain embodiments, Form A comprises less than 0.1% water as determined in a coulemetric Karl Fischer (KF) titrator equipped with an oven sample processor set at 225° C.

In certain embodiments, no significant degradation or residual solvent for Form A is observed by $^1$H NMR (FIG. 7).

In certain embodiments, Form A of Compound 1 is characterized by its stability profile upon compression. In certain embodiments, Form A is stable, e.g., its XRPD pattern remains substantially unchanged with broader diffraction peaks, upon application of 2000-psi pressure for about 1 minute (FIG. 8).

In still another embodiment, Form A of Compound 1 is substantially pure. In certain embodiments, the substantially pure Form A of Compound 1 is substantially free of other solid forms, e.g., amorphous form. In certain embodiments, the purity of the substantially pure Form A of Compound 1 is no less than about 95% pure, no less than about 96% pure, no less than about 97% pure, no less than about 98% pure, no less than about 98.5% pure, no less than about 99% pure, no less than about 99.5% pure, or no less than about 99.8% pure.

Certain embodiments Form A of Compound 1 is substantially pure. In certain embodiments herein Form A of Compound 1 is substantially free of other solid forms comprising Compound 1 including, e.g., Forms B, C, D, E and/or an amorphous solid form comprising Compound 1. In certain embodiments, Form A is a mixture of solid forms comprising Compound 1, including, e.g., a mixture comprising one or more of the following: Forms B, C, D, E and an amorphous solid form comprising Compound 1.

Form B of 2-(4-chlorophenyl)-N-((2-(2,6-dioxopiperidin-3-yl)-1-oxoisoindolin-5-yl)methyl)-2,2-difluoroacetamide In certain embodiments, the lyophilized formulations provided herein are prepared from anhydrous Form B of Compound 1.

In certain embodiments, Form B is obtained by antisolvent recrystallization from certain solvent systems, for example, solvent systems comprising one or more of the following solvents: methanol/water, DMSO/isopropanol, DMSO/toluene, and DMSO/water. In certain embodiments, Form B is obtained by cooling recrystallization from THF/water (1:1).

In certain embodiments, Form B is crystalline, as indicated by, e.g., X-ray powder diffraction measurements. In one embodiment, Form B of Compound 1 has an X-ray powder diffraction pattern substantially as shown in FIG. 9.

In one embodiment, Form B of Compound 1 has one or more characteristic X-ray powder diffraction peaks at a two-theta angle of approximately 15.4, 16.3, 16.7, 17.7, 20.4, 25.6 or 27.5, degrees 2θ as depicted in FIG. 9. In another embodiment, Form B of Compound 1 has one, two, three or four characteristic X-ray powder diffraction peaks at a two-theta angle of approximately 16.7, 25.6, 15.4 or 16.3 degrees 2θ. In another embodiment, Form B of Compound 1 has one, two, three, four, five, six or seven characteristic X-ray powder diffraction peaks as set forth in Table 2. In another embodiment, Form B of Compound 1 has one, two, or three characteristic X-ray powder diffraction peaks as set forth in Table 2.

In one embodiment, Form B of Compound 1 has the SEM picture as shown in FIG. 10. In one embodiment, a crystalline form of Compound 1 has a thermogravimetric (TGA) thermograph corresponding substantially to the representative TGA thermogram as depicted in FIG. 11. In certain embodiments, Form B shows no TGA weight loss below 170° C. In certain embodiments, Form B shows a TGA weight loss of 0.4% between 170~230° C.

In one embodiment, crystalline Form B of Compound 1 has a DSC thermogram corresponding substantially as depicted in FIG. 12. In certain embodiments, Form B is characterized by a DSC plot comprising a melt/recrystallization event at 219~224° C. and a major melting event with a peak temperature of 231° C.

In certain embodiments, Form B is characterized by dynamic vapor sorption analysis. A representative dynamic vapor sorption (DVS) isotherm plot is shown in FIG. 13. In certain embodiments, when the relative humidity ("RH") is increased from about 0% to about 90% RH, Form B exhibits about 1.4% w/w water uptake. In certain embodiments, Form B comprises less than 0.1% water as determined in a coulemetric Karl Fischer (KF) titrator equipped with an oven sample processor set at 225° C.

In certain embodiments, Form B shows no significant degradation or residual solvent by $^1$H NMR (FIG. 14).

In certain embodiments, Form B of Compound 1 is characterized by its stability profile upon compression. In certain embodiments, Form B is stable, e.g., its XRPD pattern remains substantially unchanged with broader diffraction peaks, upon application of 2000-psi pressure for about 1 minute (FIG. 15).

In still another embodiment, Form B of Compound 1 is substantially pure. In certain embodiments, the substantially pure Form B of Compound 1 is substantially free of other solid forms, e.g., amorphous form. In certain embodiments, the purity of the substantially pure Form B of Compound 1 is no less than about 95% pure, no less than about 96% pure, no less than about 97% pure, no less than about 98% pure, no less than about 98.5% pure, no less than about 99% pure, no less than about 99.5% pure, or no less than about 99.8% pure.

Certain embodiments, Form B of Compound 1 is substantially pure. In certain embodiments, Form B of Compound 1 is substantially free of other solid forms comprising Compound 1 including, e.g., Forms A, C, D, E, and/or an amorphous solid form comprising Compound 1. In certain embodiments, Form B is a mixture of solid forms comprising Compound 1, including, e.g., a mixture comprising one or more of the following: Forms A, C, D, E, and an amorphous solid form comprising Compound 1.

Form C of 2-(4-chlorophenyl)-N-((2-(2,6-dioxopiperidin-3-yl)-1-oxoisoindolin-5-yl)methyl)-2,2-difluoroacetamide In certain embodiments, the lyophilized formulations provided herein are prepared from anhydrous Form C of Compound 1. In certain embodiments, Form C is the most thermodynamically stable anhydrate among the crystal forms of Compound 1.

In certain embodiments, Form C is obtained by slurrying Compound 1 in certain solvent systems, for example, solvent systems comprising one or more of the following solvents: acetonitril/water, acetone, or ethanol/water for extended period of time.

In certain aspects, Form C is obtained by slurrying Form B (1×wt) in acetone (30×vol) at an elevated temperature, for example, from 60-80° C. or 70-75° C. for at least 24 hours, and cooling the mixture to room temperature. In one aspect, the slurrying is conducted at a temperature of 70-75° C. under nitrogen pressure of 50-55-psi. In one aspect, the mixture is cooled to room temperature over at least 6 hours.

In certain embodiments, Form C is crystalline, as indicated by, e.g., X-ray powder diffraction measurements. In one embodiment, Form C of Compound 1 has an X-ray powder diffraction pattern substantially as shown in FIG. 16.

In one embodiment, Form C of Compound 1 has one or more characteristic X-ray powder diffraction peaks at a two-theta angle of approximately 7.4, 11.5, 15.8, 16.7, 16.9, 17.7, 18.4, 19.2, 19.5, 21.1, 23.4, 24.7, or 29.9, degrees 2θ as depicted in FIG. 16. In another embodiment, Form C of Compound 1 has one, two, three or four characteristic X-ray powder diffraction peaks at a two-theta angle of approximately 16.7, 16.9, 17.7 or 24.7 degrees 2θ. In another embodiment, Form C of Compound 1 has one, two, three, four, five, six or seven characteristic X-ray powder diffraction peaks as set forth in Table 3. In another embodiment, Form C of Compound 1 has one, two, or three characteristic X-ray powder diffraction peaks as set forth in Table 3.

In one embodiment, Form C of Compound 1 has the SEM picture as shown in FIG. 17. In one embodiment, a crystalline form of Compound 1 has a thermogravimetric (TGA) thermograph corresponding substantially to the representative TGA thermogram as depicted in FIG. 18. In certain embodiments, Form C shows no TGA weight loss.

In one embodiment, crystalline Form C of Compound 1 has a DSC thermogram corresponding substantially as depicted in FIG. 19. In certain embodiments, Form C is characterized by a DSC plot comprising melting event with an onset temperature of 232° C. and heat of fusion of 126 J/g.

In certain embodiments, Form C is characterized by dynamic vapor sorption analysis. A representative dynamic vapor sorption (DVS) isotherm plot is shown in FIG. 20. In certain embodiments, when the relative humidity ("RH") is increased from about 0% to about 90% RH, Form C exhibits about 0.6% w/w water uptake. In certain embodiments, Form C comprises less than 0.1% water as determined in a coulemetric Karl Fischer (KF) titrator equipped with an oven sample processor set at 225° C.

In certain embodiments, Form C shows no significant degradation or residual solvent by $^1$H NMR (FIG. 21).

In certain embodiments, Form C of Compound 1 is characterized by its stability profile upon compression. In certain embodiments, Form C is stable, e.g., its XRPD pattern remains substantially unchanged with broader diffraction peaks, upon application of 2000-psi pressure for about 1 minute (FIG. 22).

In still another embodiment, Form C of Compound 1 is substantially pure. In certain embodiments, the substantially pure Form C of Compound 1 is substantially free of other solid forms, e.g., amorphous form. In certain embodiments, the purity of the substantially pure Form C of Compound 1 is no less than about 95% pure, no less than about 96% pure, no less than about 97% pure, no less than about 98% pure, no less than about 98.5% pure, no less than about 99% pure, no less than about 99.5% pure, or no less than about 99.8% pure.

In certain embodiments, Form C of Compound 1 is substantially pure. In certain embodiments, Form C of Compound 1 is substantially free of other solid forms comprising Compound 1 including, e.g., Forms A, B, D, E, and/or an amorphous solid form comprising Compound 1. In certain embodiments, Form C is a mixture of solid forms comprising Compound 1, including, e.g., a mixture comprising one or more of the following: Forms A, B, D, E, and an amorphous solid form comprising Compound 1.

Form D of 2-(4-chlorophenyl)-N-((2-(2,6-dioxopiperidin-3-yl)-1-oxoisoindolin-5-yl)methyl)-2,2-difluoroacetamide In certain embodiments, the lyophilized formulations provided herein are prepared from Form D of Compound 1. In certain embodiments, Form D of Compound 1 is a DMSO solvate.

In certain embodiments, Form D is obtained by heating Form B in DMSO/methyl isobutyl ketone and cooling the solution.

In certain embodiments, Form D is crystalline, as indicated by, e.g., X-ray powder diffraction measurements. In one embodiment, Form D of Compound 1 has an X-ray powder diffraction pattern substantially as shown in FIG. 23.

In one embodiment, Form D of Compound 1 has one or more characteristic X-ray powder diffraction peaks at a two-theta angle of approximately 14.1, 14.3, 18.8, 19.1, 23.6 or 24.0 degrees 2θ as depicted in FIG. 23. In another embodiment, Form D of Compound 1 has one, two, three or four characteristic X-ray powder diffraction peaks at a two-theta angle of approximately 14.1, 14.3, 18.8 or 19.1 degrees 2θ. In another embodiment, Form D of Compound 1 has one, two, three, four, five, six or seven characteristic X-ray powder diffraction peaks as set forth in Table 4. In another embodiment, Form D of Compound 1 has one, two, or three characteristic X-ray powder diffraction peaks as set forth in Table 4.

In one embodiment, provided herein is a crystalline form of Compound 1 having a thermogravimetric (TGA) thermograph corresponding substantially to the representative TGA thermogram as depicted in FIG. 24. In certain embodiments, Form D shows TGA weight loss of about 14.1% up to 140° C.

In certain embodiments, Form D comprises DMSO in about 14.3 wt % as measured by gas chromatography.

In still another embodiment, Form D of Compound 1 is substantially pure. In certain embodiments, the substantially pure Form D of Compound 1 is substantially free of other solid forms, e.g., amorphous form. In certain embodiments, the purity of the substantially pure Form D of Compound 1 is no less than about 95% pure, no less than about 96% pure, no less than about 97% pure, no less than about 98% pure, no less than about 98.5% pure, no less than about 99% pure, no less than about 99.5% pure, or no less than about 99.8% pure.

In certain embodiments Form D of Compound 1 is substantially pure. In certain embodiments, Form D of Compound 1 is substantially free of other solid forms comprising Compound 1 including, e.g., Forms A, B, C, E, and/or an amorphous solid form comprising Compound 1 as provided herein. In certain embodiments, Form D is a mixture of solid forms comprising Compound 1, including, e.g., a mixture comprising one or more of the following: Forms A, B, C, E, and an amorphous solid form comprising Compound 1.

Form E of 2-(4-chlorophenyl)-N-((2-(2,6-dioxopiperidin-3-yl)-1-oxoisoindolin-5-yl)methyl)-2,2-difluoroacetamide In certain embodiments, the lyophilized formulations provided herein are prepared from Form E of Compound 1. In certain embodiments, Form E of Compound 1 is a DMSO solvate.

In certain embodiments, Form E is obtained from Form C in DMSO/MIBK or DMSO/IPA or DMSO/anisole at room temperature.

In certain embodiments, Form E is crystalline, as indicated by, e.g., X-ray powder diffraction measurements. In one embodiment, Form E of Compound 1 has an X-ray powder diffraction pattern substantially as shown in FIG. 25.

In one embodiment, Form E of Compound 1 has one or more characteristic X-ray powder diffraction peaks at a two-theta angle of approximately 10.5, 12.5, 16.1, 17.0, 18.5, 21.2, 21.7, 22.6, 22.9, 23.4, 23.8, 24.1, 25.1 or 26.7, degrees 2θ as depicted in FIG. 25. In another embodiment, Form E of Compound 1 has one, two, three or four characteristic X-ray powder diffraction peaks at a two-theta angle of approximately 16.1, 17.0, 21.2 or 22.9 degrees 2θ. In another embodiment, Form E of Compound 1 has one, two, three, four, five, six or seven characteristic X-ray powder diffraction peaks as set forth in Table 5. In another embodiment, Form E of Compound 1 has one, two, or three characteristic X-ray powder diffraction peaks as set forth in Table 5.

In one embodiment, provided herein is a crystalline form of Compound 1 having a thermogravimetric (TGA) thermograph corresponding substantially to the representative TGA thermogram as depicted in FIG. 26. In certain embodiments, Form E shows TGA weight loss of about 19.4% up to 120° C. In certain embodiments, Form E shows additional weight loss of 24.9% between 120 and 220° C.

In one embodiment, Form E of Compound 1 is substantially pure. In certain embodiments, the substantially pure Form E of Compound 1 is substantially free of other solid forms, e.g., amorphous form. In certain embodiments, the purity of the substantially pure Form E of Compound 1 is no less than about 95% pure, no less than about 96% pure, no less than about 97% pure, no less than about 98% pure, no less than about 98.5% pure, no less than about 99% pure, no less than about 99.5% pure, or no less than about 99.8% pure.

In certain embodiments, Form E of Compound 1 is substantially pure. In certain embodiments herein, Form E of Compound 1 is substantially free of other solid forms comprising Compound 1 including, e.g., Forms A, B, C, D and/or an amorphous solid form comprising Compound 1. In certain embodiments, Form E is a mixture of solid forms comprising Compound 1, including, e.g., a mixture comprising one or more of the following: Forms A, B, C, D and an amorphous solid form comprising Compound 1.

Amorphous Form of 2-(4-chlorophenyl)-N-((2-(2,6-dioxopiperidin-3-yl)-1-oxoisoindolin-5-yl)methyl)-2,2-difluoroacetamide In certain embodiments, the lyophilized formulations provided herein comprise amorphous Compound 1.

In certain embodiments, provided herein are methods for making the amorphous form by heating Compound 1 in THF and water and cooling the solution.

In one embodiment, provided herein is an amorphous solid form of Compound 1 having a modulated DSC thermogram as depicted in FIG. 27.

In one embodiment, amorphous Compound 1 has an X-ray powder diffraction pattern substantially as shown in FIG. 28.

In one embodiment, amorphous Compound 1 has a $^1$H NMR spectrum substantially as shown in FIG. 29.

In still another embodiment, amorphous Compound 1 is substantially pure. In certain embodiments, the substantially pure amorphous Compound 1 is substantially free of other solid forms, e.g., Form A, Form B, Form C, Form D or Form E. In certain embodiments, the purity of the substantially pure amorphous Compound 1 is no less than about 95% pure, no less than about 96% pure, no less than about 97% pure, no less than about 98% pure, no less than about 98.5% pure, no less than about 99% pure, no less than about 99.5% pure, or no less than about 99.8% pure.

6.3 Exemplary Formulations

Provided herein are stable lyophilized formulations of Compound 1. In one embodiment, the lyophilized formulations of Compound 1 comprise a solid form of 2-(4-chlorophenyl)-N-((2-(2,6-dioxopiperidin-3-yl)-1-oxoisoindolin-5-yl)methyl)-2,2-difluoroacetamide. In one embodiment, the lyophilized formulations of Compound 1 comprise an amorphous form of 2-(4-chlorophenyl)-N-((2-(2,6-dioxopiperidin-3-yl)-1-oxoisoindolin-5-yl)methyl)-2,2-difluoroacetamide.

In certain embodiment, the lyophilized formulations provided herein comprise Compound 1, a buffer and a bulking agent. In one embodiment, a lyophilized formulation provided herein comprises about 0.1-2% Compound 1, about 2-15% buffer and about 70-95% bulking agent based on the total weight of the lyophilized formulation.

In one aspect, the lyophilized formulation provided herein comprises Compound 1 in an amount of about 0.1 to about 2% based on the total weight of the lyophilized formulation. In certain embodiments, the amount of Compound 1 is from about 0.1% to about 1.5%, about 0.1% to about 1% or about 0.35% to about 0.9% based on the total weight of the lyophilized formulation. In certain embodiments, the amount of Compound 1 is about 0.1%, 0.2%, 0.3%, 0.35%, 0.36%, 0.4%, 0.5%, 0.6%, 0.7%, 0.8%, 0.9%, or 1.0% based on the total weight of the lyophilized formulation. In one embodiment, the amount of Compound 1 in the lyophilized formulation is about 0.3 to about 0.4% based on the total weight of the lyophilized formulation. In one embodiment, the amount of Compound 1 in the lyophilized formulation is about 0.36% based on the total weight of the lyophilized formulation. In one embodiment, the amount of Compound 1 in the lyophilized formulation is about 0.9 to about 1% based on the total weight of the lyophilized formulation. In one embodiment, the amount of Compound 1 in the lyophilized formulation is about 0.93% based on the total weight of the lyophilized formulation.

In another aspect is a lyophilized formulation that comprises Compound 1 in an amount of about 0.1 mg to about 5 mg in a 20 cc vial. In still another aspect is a lyophilized formulation that comprises Compound 1 in an amount of about 0.1 mg to about 5 mg, about 0.1 mg to about 4 mg, about 0.1 mg to about 3 mg, about 0.1 mg to about 2 mg, about 0.5 mg to about 5 mg, about 0.5 mg to about 3 mg, about 0.5 mg to about 2 mg, about 0.5 mg to about 1.5 mg in a 20 cc vial. In one aspect Compound 1 is present in an amount of about 0.5, 0.6, 0.7, 0.75, 0.76, 0.8, 0.9, 1.0, 1.2 mg in a 20 cc vial. In one aspect Compound 1 is present in an amount of about 0.76 mg in a 20 cc vial. In one aspect Compound 1 is present in an amount of about 1 mg in a 20 cc vial.

In one aspect, the lyophilized formulations provided herein contain a citrate buffer. In one aspect, the amount of citrate buffer in the formulations provided herein is from about 5% to about 25% based on total weight of the lyophilized formulation. In one aspect, the amount of citrate buffer in the formulations provided herein is about 10, 11, 12, 12.5, 12.7, 12.78, 12.8, 13, 14, 15, 16, 17, 17.3, 17.42, 17.5, 17.7, 18, 19 or 20% based on total weight of the lyophilized formulation. In one aspect, the amount of citrate buffer in the formulations provided herein is about 12.78% based on total weight of the lyophilized formulation. In one aspect, the amount of citrate buffer in the formulations provided herein is about 17.42% based on total weight of the lyophilized formulation.

In one embodiment, the citrate buffer comprises anhydrous citric acid and anhydrous sodium citrate. In certain embodiments, the amount of anhydrous citric acid is from about 2% to about 10%, about 3% to about 9%, about 5% to about 8% or about 6% to about 8% based on total weight of the lyophilized formulation. In certain embodiments, the amount of anhydrous citric acid in the lyophilized formulation is about 2%, 4%, 6%, 6.2%, 6.4%, 6.6%, 6.8%, 7%, 7.3%, 7.4%, 7.5%, 8%, 8.5% or 9% based on total weight of the lyophilized formulation. In one embodiment, the amount of anhydrous citric acid in the lyophilized formulation is about 6%, 6.2%, 6.4%, 6.41%, 6.6%, 6.8% or 7% based on total weight of the lyophilized formulation. In one embodiment, the amount of anhydrous citric acid in the lyophilized formulation is about 7%, 7.3%, 7.4%, 7.43%, 7.5% or 8% based on total weight of the lyophilized formulation. In one embodiment, the amount of anhydrous citric acid in the lyophilized formulation is about 6.41% based on total weight of the lyophilized formulation. In one embodiment, the amount of anhydrous citric acid in the lyophilized formulation is about 7.43% based on total weight of the lyophilized formulation.

In still another aspect is a lyophilized formulation that comprises anhydrous citric acid in an amount of about 5 mg to about 20 mg in a 20 cc vial. In one embodiment, the amount of anhydrous citric acid is about 5, 6, 7, 8, 9, 10, 11, 12, 13, 14, 15, 16, 17, 18, 19 or 20 mg in a 20 cc vial. In one embodiment, the amount of anhydrous citric acid is about 17.7 mg in a 20 cc vial. In one embodiment, the amount of anhydrous citric acid is about 6.1 mg in a 20 cc vial.

In certain embodiments, the amount of anhydrous sodium citrate is from about 2% to about 15%, about 4% to about 15% or about 5% to about 10% based on total weight of the lyophilized formulation. In certain embodiments, the amount of anhydrous sodium citrate in the lyophilized formulation is about 2%, 3%, 4%, 5%, 6%, 6.2%, 6.37%, 6.4%, 6.6%, 6.8%, 7%, 7.5%, 8%, 8.5%, 9%, 9.5%, 10%, 12% or about 15% based on total weight of the lyophilized formulation. In one embodiment, the amount of anhydrous sodium citrate in the lyophilized formulation is about 6%, 6.2%, 6.37% 6.4%, 6.6%, 6.8% or 7% based on total weight of the lyophilized formulation. In one embodiment, the amount of anhydrous sodium citrate in the lyophilized formulation is about 8%, 8.5%, 9%, 9.5%, 9.99%, 10% or 10.5% based on total weight of the lyophilized formulation. In one embodiment, the amount of anhydrous sodium citrate in the lyophilized formulation is about 6.37% based on total weight of the lyophilized formulation. In one embodiment, the amount of anhydrous sodium citrate in the lyophilized formulation is about 9.99% based on total weight of the lyophilized formulation.

In still another aspect is a lyophilized formulation that comprises anhydrous sodium citrate in an amount of about 5 mg to about 20 mg in a 20 cc vial. In one embodiment, the amount of anhydrous sodium citrate is about 5, 6, 7, 8, 9, 10, 11, 12, 13, 14, 15, 16, 17, 18, 19 or 20 mg in a 20 cc vial. In one embodiment, the amount of anhydrous sodium citrate is about 17.6 mg in a 20 cc vial. In one embodiment, the amount of anhydrous sodium citrate is about 8.2 mg in a 20 cc vial.

In certain embodiments, the amount of anhydrous citric acid in the lyophilized formulation is about 2%, 4%, 6%, 6.2%, 6.4%, 6.6%, 6.8%, 7%, 7.3%, 7.4%, 7.5%, 8%, 8.5% or 9% and the amount of anhydrous sodium citrate in the lyophilized formulation is about 2%, 3%, 4%, 5%, 6%, 6.2%, 6.4%, 6.6%, 6.8%, 7%, 7.5%, 8%, 8.5%, 9%, 9.5%, 10%, 12% or about 15% based on total weight of the lyophilized formulation. In one embodiment, the amount of anhydrous citric acid in the lyophilized formulation is about 6%, 6.2%, 6.4%, 6.6%, 6.8% or 7% and the amount of anhydrous sodium citrate in the lyophilized formulation is about 6%, 6.2%, 6.4%, 6.6%, 6.8% or 7% based on total weight of the lyophilized formulation. In one embodiment, the amount of anhydrous citric acid in the lyophilized formulation is about 7%, 7.3%, 7.4%, 7.5% or 8% and the amount of anhydrous sodium citrate in the lyophilized formulation is about 8%, 8.5%, 9%, 9.5%, 10% or 10.5% based on total weight of the lyophilized formulation. In one embodiment, the amount of anhydrous citric acid is about 6.1 mg and the amount of anhydrous sodium citrate is about 8.2 mg in a 20 cc vial. In one embodiment, the amount of anhydrous citric acid is about 17.7 mg and the amount of anhydrous sodium citrate is about 17.6 mg in a 20 cc vial.

In one aspect, the bulking agent in the lyophilized formulations provided herein comprises Captisol®, mannitol or Kleptose®, for example, β-cyclodextrin, hydroxypropyl β-cyclodextrin and methylated β-cyclodextrin. In certain embodiments, the bulking agent in the lyophilized formulations provided herein comprises Kleptose® hydroxypropyl β-cyclodextrins (Kleptose®HPB). In certain embodiments, the amount of the bulking agent in the lyophilized compositions provided herein is from about 70% to about 95%, about 75% to about 90% or about 80% to about 90% based on total weight of the lyophilized formulation. In certain embodiments, the amount of hydroxypropyl β-cyclodextrin in the lyophilized compositions provided herein is from about 70% to about 95%, about 75% to about 90% or about 80% to about 90% based on total weight of the lyophilized formulation. In certain embodiments, the amount of hydroxypropyl β-cyclodextrin in the lyophilized compositions provided herein is about 75%, 80%, 81%, 81.61%, 82%, 83%, 84%, 85%, 86%, 86.86%, 87%, 88%, 89% or 90% based on total weight of the lyophilized formulation. In one embodiment, the amount of hydroxypropyl β-cyclodextrin in the lyophilized compositions provided herein is about 86.86% based on total weight of the lyophilized formulation. In one embodiment, the amount of hydroxypropyl β-cyclodextrin in the lyophilized compositions provided herein is about 81.61% based on total weight of the lyophilized formulation.

In another aspect is a lyophilized formulation that comprises Kleptose®HPB in an amount of about 67 mg in a 20 cc vial. In still another aspect is a lyophilized formulation that comprises Kleptose®HPB in an amount of about 240 mg in a 20 cc vial.

In certain embodiments, the lyophilized formulation upon reconstitution has a pH of about 4 to 5. In one embodiment, the lyophilized formulation upon reconstitution has a pH of about 4, 4.1, 4.2, 4.3, 4.4, 4.5, 4.6, 4.7, 4.8, 4.9 or 5.

In certain embodiments, provided herein is a container comprising a lyophilized composition provided herein. In one aspect, the container is a glass vial. In one aspect, the container is a 20 cc glass vial.

In certain embodiments, the lyophilized formulation has a composition as described in the Table 21. In certain embodiments, the lyophilized formulation has a composition as described in the Table 34.

The lyophilized formulations of Compound 1 provided herein can be administered to a patient in need thereof using standard therapeutic methods for delivering Compound 1 including, but not limited to, the methods described herein. In one embodiment, the lyophilized formulations provided herein are reconstituted in a pharmaceutically acceptable solvent to produce a pharmaceutically acceptable solution, wherein the solution is administered (such as by intravenous injection) to the patient.

The lyophilized formulation provided herein can be constituted for parenteral administration to a patient using any pharmaceutically acceptable diluent. Such diluents include, but are not limited to Sterile Water for Injection (SWFI), Dextrose 5% in Water (D5W), or a cosolvent system. Any quantity of diluent may be used to constitute the lyophilized formulation such that a suitable solution for injection is prepared. Accordingly, the quantity of the diluent must be sufficient to dissolve the lyophilized formulation. In one embodiment, 1-5 mL or 1 to 3 mL of a diluent are used to constitute the lyophilized formulation to yield a final concentration of, about 0.1-5 mg/mL, about 0.1-1 mg/mL, about 0.5-1 mg/mL of Compound 1. In certain embodiments, the final concentration of Compound 1 in the reconstituted solution is about 0.5 mg/mL. In certain embodiment, the volume of the reconstitution diluent varies between 2 ml and 20 ml to yield a final concentration of 0.05-0.5 mg/mL. In certain embodiment, depending on the required dose, multiple vials may be used for reconstitution.

The constituted solutions of lyophilized formulation can be stored and used within up to about 24 hours, about 12 hours or about 8 hours. In some embodiments, the solution is used within 8 hour of preparation. In some embodiments, the solution is used within 5 hour of preparation. In some embodiments, the solution is used within 1 hour of preparation.

The lyophilized formulation can be a formulation as set forth in Table 21 and/or Table 34. Thus, in certain embodiments, the lyophilized formulation is represented by the designations in Table 21 and/or Table 34 (e.g., Formulation IA, Formulation IC, Formulation II, Formulation III, Formulation IX, or Formulation ID). In one embodiment, the formulation is Formulation IX. In one embodiment, the formulation is Formulation IC. In one embodiment, the formulation is Formulation ID.

In one aspect provided herein is a lyophilized formulation in a 20 cc vial that includes: Compound 1 at an amount that provides 1 mg 2-(4-chlorophenyl)-N-((2-(2,6-dioxopiperidin-3-yl)-1-oxoisoindolin-5-yl)methyl)-2,2-difluoroacetamide and a pharmaceutically acceptable carrier or excipient that includes a buffer and bulking agent as described herein. The buffer and bulking agent can be present at an amount as described herein.

In one aspect provided herein is a lyophilized formulation in a 20 cc vial that includes: Compound 1 at an amount that provides 1 mg 2-(4-chlorophenyl)-N-((2-(2,6-dioxopiperidin-3-yl)-1-oxoisoindolin-5-yl)methyl)-2,2-difluoroacetamide, 17.7 mg anhydrous citric acid, 17.6 mg anhydrous sodium citrate and 240 mg HPB as described herein. In one embodiment, the lyophilized formulation in a 20 cc vial is reconstituted with 2 mL sterile water for injection.

In one aspect provided herein is an aqueous composition comprising a lyophilized formulation provided herein. In one embodiment, the aqueous solution comprises 0.5 mg/mL Compound 1.

6.4 Process for Making Formulations

The lyophilized formulations provided herein can be prepared by any of the methods known in the art and as described herein, but all methods include the step of bringing the active ingredient into association with the pharmaceutically acceptable excipient, which constitutes one or more necessary ingredients (such as buffer and bulking agent).

In one aspect, the formulations provided herein are prepared by dissolving Compound 1 and a bulking agent in a citrate buffer to obtain a solution and lyophilizing the solution. A flow chart illustrating an exemplary process is provided in FIG. 32. In one embodiment, the process comprises dissolving Kleptose® HPB in a 20 mM, pH 4.3 citrate buffer to obtain a mixture, adding Compound 1 dissolved in DMA to the mixture to obtain a solution, filtering the solution into a 20 cc vial, and lyophilizing the solution. In one embodiment, the solution is filtered through one or more 0.45 μm and/or 0.22 μm filters. In one embodiment, the vial is sealed under nitrogen after lyophilization.

In one aspect, the lyophilization process contains three stages: freezing, primary drying, and secondary drying. A liquid formulation is transformed to a lyophilized powder form by going through complete solidification through freezing stage, sublimation of ice and solvents through primary drying, and desorption of residual moisture and solvents through secondary drying. The shelf temperature and chamber pressure in the primary drying and secondary drying are controlled to obtained the desired quality of the finished drug product. In one aspect of the process, the cake appearance and structure was characterized by visual inspection.

6.5 Kits

Pharmaceutical packs or kits which comprise pharmaceutical compositions or dosage forms provided herein are also provided. Exemplary kits include notice in the form prescribed by a governmental agency regulating the manufacture, use or sale of pharmaceuticals products, which notice reflects approval by the agency of manufacture, use or sale for human administration 6.6 Methods of Treating In one embodiment, provided herein is a method of treating and preventing cancer, which comprises administering to a patient a lyophilized formulation of Compound 1 provided herein.

In another embodiment, provided herein is method of managing cancer, which comprises administering to a patient a lyophilized formulation of Compound 1 provided herein.

Also provided herein are methods of treating patients who have been previously treated for cancer but are non-responsive to standard therapies, as well as those who have not previously been treated. The invention also encompasses methods of treating patients regardless of patient's age, although some diseases or disorders are more common in certain age groups. The invention further encompasses methods of treating patients who have undergone surgery in an attempt to treat the disease or condition at issue, as well as those who have not. Because patients with cancer have heterogeneous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with cancer.

As used herein, the term "cancer" includes, but is not limited to, solid tumors and blood borne tumors. The term "cancer" refers to disease of skin tissues, organs, blood, and vessels, including, but not limited to, cancers of the bladder, bone, blood, brain, breast, cervix, chest, colon, endometrium, esophagus, eye, head, kidney, liver, lymph nodes, lung, mouth, neck, ovaries, pancreas, prostate, rectum, stomach, testis, throat, and uterus. Specific cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, colorectal cancer, including stage 3 and stage 4, unresectable colorectal carcinoma, metastatic hepatocellular carcinoma, Kaposi's sarcoma, karyotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma.

In certain embodiments, the cancer is a solid tumor. In certain embodiments, the solid tumor is metastatic. In certain embodiments, the solid tumor is drug-resistant. In certain embodiments, the solid tumor is hepatocellular carcinoma, prostate cancer, ovarian cancer, or glioblastoma.

In certain embodiments, the cancer is a blood borne tumor. In certain embodiments, the blood borne tumor is metastatic. In certain embodiments, the blood borne tumor is drug resistant. In certain embodiments, the cancer is leukemia. In another embodiment, the cancer is MDS.

In one embodiment, methods provided herein encompass treating, preventing and/or managing various types of leukemias such as chronic lymphocytic leukemia (CLL), chronic myelocytic leukemia (CML), acute lymphoblastic leukemia (ALL), acute myeloid leukemia (AML), and acute myeloblastic leukemia (AML) by administering a therapeutically effective amount of a lyophilized formulation provided herein.

In some embodiments, the methods provided herein encompass treating, preventing and/or managing acute leukemia in a subject. In some embodiments, the acute leukemia is acute myeloid leukemia (AML), which includes, but is not limited to, undifferentiated AML (M0), myeloblastic leukemia (M1), myeloblastic leukemia (M2), promyelocytic leukemia (M3 or M3 variant (M3V)), myelomonocytic leukemia (M4 or M4 variant with eosinophilia (M4E)), monocytic leukemia (M5), erythroleukemia (M6), and megakaryoblastic leukemia (M7). In one embodiment, the acute myeloid leukemia is undifferentiated AML (M0). In one embodiment, the acute myeloid leukemia is myeloblastic leukemia (M1). In one embodiment, the acute myeloid leukemia is myeloblastic leukemia (M2). In one embodiment, the acute myeloid leukemia is promyelocytic leukemia (M3 or M3 variant (M3V)). In one embodiment, the acute myeloid leukemia is myelomonocytic leukemia (M4 or M4 variant with eosinophilia (M4E)). In one embodiment, the acute myeloid leukemia is monocytic leukemia (M5). In one embodiment, the acute myeloid leukemia is erythroleukemia (M6). In one embodiment, the acute myeloid leukemia is megakaryoblastic leukemia (M7).

In certain embodiments, the methods of treating, preventing and/or managing acute myeloid leukemia in a subject comprise the step of administering to the subject an amount of a lyophilized formulation of Compound 1 provided herein effective to treat, prevent and/or manage acute myeloid leukemia alone or in combination.

In one embodiment, provided herein are methods of treating, preventing and/or managing acute myeloid leukemia by intravenous administration of a lyophilized formulation of Compound 1. In one embodiment, the a lyophilized formulation of Compound 1 is dissolved in water to form an aqueous solution for intravenous administration in methods of treating, preventing and/or managing acute myeloid leukemia provided herein.

In some embodiments, the methods comprise the step of administering to the subject a lyophilized formulation of Compound 1 provided herein in combination with a second active agent in amounts effective to treat, prevent and/or manage acute myeloid leukemia.

In some embodiments, the methods provided herein encompass treating, preventing and/or managing acute lymphocytic leukemia (ALL) in a subject. In some embodiments, acute lymphocytic leukemia includes leukemia that originates in the blast cells of the bone marrow (B-cells), thymus (T-cells), and lymph nodes. The acute lymphocytic leukemia can be categorized according to the French-American-British (FAB) Morphological Classification Scheme as L1—Mature-appearing lymphoblasts (T-cells or pre-B-cells), L2—Immature and pleomorphic (variously shaped) lymphoblasts (T-cells or pre-B-cells), and L3—Lymphoblasts (B-cells; Burkitt's cells). In one embodiment, the acute lymphocytic leukemia originates in the blast cells of the bone marrow (B-cells). In one embodiment, the acute lymphocytic leukemia originates in the thymus (T-cells). In one embodiment, the acute lymphocytic leukemia originates in the lymph nodes. In one embodiment, the acute lymphocytic leukemia is L1 type characterized by mature-appearing lymphoblasts (T-cells or pre-B-cells). In one embodiment, the acute lymphocytic leukemia is L2 type characterized by immature and pleomorphic (variously shaped) lymphoblasts (T-cells or pre-B-cells). In one embodiment, the acute lymphocytic leukemia is L3 type characterized by lymphoblasts (B-cells; Burkitt's cells). In certain embodiments, the acute lymphocytic leukemia is T-cell leukemia. In one embodiment, the T-cell leukemia is peripheral T-cell leukemia. In another embodiment, the T-cell leukemia is T-cell lymphoblastic leukemia. In another embodiment, the T-cell leukemia is cutaneous T-cell leukemia. In another embodiment, the T-cell leukemia is adult T-cell leukemia. Thus, the methods of treating, preventing and/or managing acute lymphocytic leukemia in a subject comprise the step of administering to the subject an amount of a lyophilized formulation of Compound 1 provided herein effective to treat, prevent and/or manage acute lymphocytic leukemia alone or in combination with a second active agent. In some embodiments, the methods comprise the step of administering to the subject a lyophilized formulation of Compound 1 provided herein in combination with a second active agent in amounts effective to treat, prevent and/or manage acute lymphocytic leukemia.

In some embodiments, the methods provided herein encompass treating, preventing and/or managing chronic myelogenous leukemia (CML) in a subject. The methods comprise the step of administering to the subject an amount of a lyophilized formulation of Compound 1 provided herein effective to treat, prevent and/or manage chronic myelogenous leukemia. In some embodiments, the methods comprise the step of administering to the subject a lyophilized formulation of Compound 1 provided herein in combination with a second active agent in amounts effective to treat, prevent and/or manage chronic myelogenous leukemia.

In some embodiments, the methods provided herein encompass treating, preventing and/or managing chronic lymphocytic leukemia (CLL) in a subject. The methods comprise the step of administering to the subject an amount of a lyophilized formulation of Compound 1 provided herein effective to treat, prevent and/or manage chronic lymphocytic leukemia. In some embodiments, the methods comprise the step of administering to the subject a lyophilized formulation of Compound 1 provided herein in combination with a second active agent in amounts effective to treat, prevent and/or manage chronic lymphocytic leukemia.

In certain embodiments, provided herein are methods of treating, preventing, and/or managing disease in patients with impaired renal function. In certain embodiments, provided herein are method of treating, preventing, and/or managing cancer in patients with impaired renal function. In certain embodiments, provided herein are methods of providing appropriate dose adjustments for patients with impaired renal function due to, but not limited to, disease, aging, or other patient factors.

In certain embodiments, provided herein are methods of treating, preventing, and/or managing lymphoma, including non-Hodgkin's lymphoma. In some embodiments, provided herein are methods for the treatment and/or management of non-Hodgkin's lymphoma (NHL), including but not limited to, diffuse large B-cell lymphoma (DLBCL), using prognostic factors.

In certain embodiments, provided herein are methods of treating, preventing, and/or managing multiple myeloma, including relapsed/refractory multiple myeloma in patients with impaired renal function or a symptom thereof, comprising administering a therapeutically effective amount of a lyophilized formulation of Compound 1 provided herein to a patient having relapsed/refractory multiple myeloma with impaired renal function.

In one embodiment, provided herein are methods of treating, preventing, and/or managing a myelodysplastic syndrome (MDS) in a subject. The methods comprise the step of administering to the subject a therapeutically active amount of a lyophilized formulation of Compound 1 provided herein. In one embodiment, the MDS is relapsed, resistant or refractory MDS. In one embodiment, MDS is selected from refractory anemia (RA); RA with ringed sideroblasts (RARS); RA with excess of blasts (RAEB); refractory cytopenia with multilineage dysplasia (RCMD), refractory cytopenia with unilineage dysplasia (RCUD); unclassifiable myelodysplastic syndrome (MDS-U), myelodysplastic syndrome associated with an isolated del(5q) chromosome abnormality, therapy-related myeloid neoplasms and chronic myelomonocytic leukemia (CMML). In some embodiments, the methods comprise the step of administering to the subject a lyophilized formulation of Compound 1 provided herein in combination with a second active agent in amounts effective to treat, prevent and/or manage MDS.

In certain embodiments, a therapeutically or prophylactically effective amount of Compound 1 is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, from about 0.05 to about 10 mg per day, from about 0.05 to about 5 mg per day, from about 0.1 to about 5 mg per day, or from about 0.5 to about 5 mg per day.

In certain embodiments, the therapeutically or prophylactically effective amount is about 0.1, about 0.2, about 0.5, about 1, about 2, about 3, about 4, about 5, about 6, about 7, about 8, about 9, about 10, about 15, about 20, about 25, about 30, about 40, about 45, about 50, about 60, about 70, about 80, about 90, about 100, or about 150 mg per day. In some such embodiments, the therapeutically or prophylactically effective amount is about 2, about 3, about 4, about 5, about 6 or about 7 mg per day.

In one embodiment, the recommended daily dose range of Compound 1, for the conditions described herein lie within the range of from about 0.05 mg to about 50 mg per day, preferably given as a single once-a-day dose, or in divided doses throughout a day. In some embodiments, the dosage ranges from about 1 mg to about 50 mg per day. In other embodiments, the dosage ranges from about 0.5 to about 5 mg per day. Specific doses per day include 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg per day.

In a specific embodiment, the recommended starting dosage may be 0.1, 0.5, 1, 2, 3, 4, 5, 10, 15, 20, 25 or 50 mg per day. In another embodiment, the recommended starting dosage may be 0.1, 0.5, 1, 2, 3, 4, or 5 mg per day. The dose may be escalated to 15, 20, 25, 30, 35, 40, 45 and 50 mg/day. In a specific embodiment, Compound 1 can be administered in an amount of about 25 mg/day to patients with leukemia, including AML. In a particular embodiment, Compound 1 can be administered in an amount of about 10 mg/day to patients with leukemia, including AML. In a particular embodiment, Compound 1 can be administered in an amount of about 5 mg/day to patients with leukemia, including AML. In a particular embodiment, Compound 1 can be administered in an amount of about 4 mg/day to patients with leukemia, including AML. In a particular embodiment, Compound 1 provided herein can be administered in an amount of about 3 mg/day to patients with leukemia, including AML. In a particular embodiment, Compound 1 provided herein can be administered in an amount of about 2 mg/day to patients with leukemia, including AML. In a particular embodiment, Compound 1 provided herein can be administered in an amount of about 1 mg/day to patients with leukemia, including AML. In a particular embodiment, Compound 1 provided herein can be administered in an amount of about 0.5 mg/day to patients with leukemia, including AML.

In a specific embodiment, Compound 1 can be administered in an amount of about 25 mg/day to patients with MDS. In a particular embodiment, Compound 1 can be administered in an amount of about 10 mg/day to patients with MDS. In a particular embodiment, Compound 1 can be administered in an amount of about 5 mg/day to patients with MDS. In a particular embodiment, Compound 1 can be administered in an amount of about 4 mg/day to patients with MDS. In a particular embodiment, Compound 1 provided herein can be administered in an amount of about 3 mg/day to patients with MDS. In a particular embodiment, Compound 1 provided herein can be administered in an amount of about 2 mg/day to patients with MDS. In a particular embodiment, Compound 1 provided herein can be administered in an amount of about 1 mg/day to patients with MDS. In a particular embodiment, Compound 1 provided herein can be administered in an amount of about 0.5 mg/day to patients with MDS.

In certain embodiments, the therapeutically or prophylactically effective amount is from about 0.001 to about 100 mg/kg/day, from about 0.01 to about 50 mg/kg/day, from about 0.01 to about 25 mg/kg/day, from about 0.01 to about 10 mg/kg/day, from about 0.01 to about 9 mg/kg/day, 0.01 to about 8 mg/kg/day, from about 0.01 to about 7 mg/kg/day, from about 0.01 to about 6 mg/kg/day, from about 0.01 to about 5 mg/kg/day, from about 0.01 to about 4 mg/kg/day, from about 0.01 to about 3 mg/kg/day, from about 0.01 to about 2 mg/kg/day, from about 0.01 to about 1 mg/kg/day, or from about 0.01 to about 0.05 mg/kg/day.

The administered dose can also be expressed in units other than mg/kg/day. For example, doses for parenteral administration can be expressed as mg/m$^2$/day. One of ordinary skill in the art would readily know how to convert doses from mg/kg/day to mg/m$^2$/day to given either the height or weight of a subject or both (see, www.fda.gov/cder/cancer/animalframe.htm). For example, a dose of 1 mg/kg/day for a 65 kg human is approximately equal to 38 mg/m$^2$/day.

In certain embodiments, the amount of Compound 1 administered is sufficient to provide a plasma concentration of the compound at steady state, ranging from about 0.001 to about 500 μM, about 0.002 to about 200 μM, about 0.005 to about 100 μM, about 0.01 to about 50 μM, from about 1 to about 50 μM, about 0.02 to about 25 μM, from about 0.05 to about 20 μM, from about 0.1 to about 20 μM, from about 0.5 to about 20 μM, or from about 1 to about 20 μM.

In other embodiments, the amount of a lyophilized formulation of Compound 1 administered is sufficient to provide a plasma concentration of the compound at steady state, ranging from about 5 to about 100 nM, about 5 to about 50 nM, about 10 to about 100 nM, about 10 to about 50 nM or from about 50 to about 100 nM.

As used herein, the term "plasma concentration at steady state" is the concentration reached after a period of administration of a lyophilized formulation provided herein. Once steady state is reached, there are minor peaks and troughs on the time dependent curve of the plasma concentration of the solid form.

In certain embodiments, the amount of a lyophilized formulation of Compound 1 administered is sufficient to provide a maximum plasma concentration (peak concentration) of the compound, ranging from about 0.001 to about 500 μM, about 0.002 to about 200 μM, about 0.005 to about 100 μM, about 0.01 to about 50 μM, from about 1 to about 50 μM, about 0.02 to about 25 μM, from about 0.05 to about 20 μM, from about 0.1 to about 20 μM, from about 0.5 to about 20 μM, or from about 1 to about 20 μM.

In certain embodiments, the amount of a lyophilized formulation of Compound 1 administered is sufficient to provide a minimum plasma concentration (trough concentration) of the compound, ranging from about 0.001 to about 500 μM, about 0.002 to about 200 μM, about 0.005 to about 100 μM, about 0.01 to about 50 μM, from about 1 to about 50 μM, about 0.01 to about 25 μM, from about 0.01 to about 20 μM, from about 0.02 to about 20 μM, from about 0.02 to about 20 μM, or from about 0.01 to about 20 μM.

In certain embodiments, the amount of a lyophilized formulation of Compound 1 administered is sufficient to provide an area under the curve (AUC) of the compound, ranging from about 100 to about 100,000 ng*hr/mL, from about 1,000 to about 50,000 ng*hr/mL, from about 5,000 to about 25,000 ng*hr/mL, or from about 5,000 to about 10,000 ng*hr/mL.

In certain embodiments, the patient to be treated with one of the methods provided herein has not been treated with anticancer therapy prior to the administration of a lyophilized formulation of Compound 1 provided herein. In certain embodiments, the patient to be treated with one of the methods provided herein has been treated with anticancer therapy prior to the administration of a lyophilized formulation of Compound 1 provided herein. In certain embodiments, the patient to be treated with one of the methods provided herein has developed drug resistance to the anticancer therapy.

The methods provided herein encompass treating a patient regardless of patient's age, although some diseases or disorders are more common in certain age groups.

The lyophilized formulation of Compound 1 provided herein can be delivered as a single dose such as, e.g., a single bolus injection, or over time, such as, e.g., continuous infusion over time or divided bolus doses over time. The lyophilized formulation of Compound 1 can be administered repeatedly if necessary, for example, until the patient experiences stable disease or regression, or until the patient experiences disease progression or unacceptable toxicity. For example, stable disease for solid tumors generally means that the perpendicular diameter of measurable lesions has not increased by 25% or more from the last measurement. Response Evaluation Criteria in Solid Tumors (RECIST) Guidelines, *Journal of the National Cancer Institute* 92(3): 205-216 (2000). Stable disease or lack thereof is determined by methods known in the art such as evaluation of patient symptoms, physical examination, visualization of the tumor that has been imaged using X-ray, CAT, PET, or MRI scan and other commonly accepted evaluation modalities.

The a lyophilized formulation of Compound 1 provided herein can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest without drug). As used herein, the term "daily" is intended to mean that a therapeutic compound, is administered once or more than once each day, for example, for a period of time. The term "continuous" is intended to mean that a therapeutic compound, is administered daily for an uninterrupted period of at least 10 days to 52 weeks. The term "intermittent" or "intermittently" as used herein is intended to mean stopping and starting at either regular or irregular intervals. For example, intermittent administration of the lyophilized formulation of Compound 1 is administration for one to six days per week, administration in cycles (e.g., daily administration for one to ten consecutive days of a 28 day cycle, then a rest period with no administration for rest of the 28 day cycle or daily administration for two to eight consecutive weeks, then a rest period with no administration for up to one week), or administration on alternate days. The term "cycling" as used herein is intended to mean that a therapeutic compound is administered daily or continuously but with a rest period. In some such embodiments, administration is once a day for two to six days, then a rest period with no administration for five to seven days. In some other such embodiments, administration is once a day for the first two to five or ten days of a 28 day cycle, followed by a rest period with no administration for the rest of the 28 day cycle.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, Compound 1 is administered once a day. In another embodiment, Compound 1 is administered twice a day. In yet another embodiment, Compound 1 provided herein is administered three times a day. In still another embodiment, Compound 1 provided herein is administered four times a day.

In certain embodiments, a lyophilized formulation of Compound 1 provided herein is administered once per day from one day to six months, from one week to three months, from one week to four weeks, from one week to three weeks, or from one week to two weeks. In certain embodiments, a lyophilized formulation of Compound 1 provided herein is administered once per day for one week, two weeks, three weeks, or four weeks. In one embodiment, a lyophilized formulation of Compound 1 provided herein is administered once per day for 1 day. In one embodiment, a lyophilized formulation of Compound 1 provided herein is administered once per day for 2 days. In one embodiment, a lyophilized formulation of Compound 1 provided herein is administered once per day for 3 days. In one embodiment, a lyophilized formulation of Compound 1 provided herein is administered once per day for 4 days. In one embodiment, a lyophilized formulation of Compound 1 provided herein is administered once per day for 5 days. In one embodiment, a lyophilized formulation of Compound 1 provided herein is administered once per day for 6 days. In one embodiment, a lyophilized formulation of Compound 1 provided herein is administered once per day for one week. In one embodiment, a lyophilized formulation of Compound 1 provided herein is administered once per day for up to 10 days. In another embodiment, a lyophilized formulation of Compound 1 provided herein is administered once per day for two weeks. In yet another embodiment, a lyophilized formulation of Compound 1 provided herein is administered once per day for three weeks. In still another embodiment, a lyophilized formulation of Compound 1 provided herein is administered once per day for four weeks.

6.6.1 Combination Therapy

The lyophilized formulation of Compound 1 provided herein can also be combined or used in combination with other therapeutic agents useful in the treatment and/or prevention of cancer described herein.

In one embodiment, provided herein is a method of treating, preventing, and/or managing cancer, comprising administering to a patient a lyophilized formulation of Compound 1 provided herein in combination with one or more second active agents, and optionally in combination with radiation therapy, blood transfusions, or surgery. Examples of second active agents are disclosed herein.

A lyophilized formulation of Compound 1 provided herein can also be combined or used in combination with other therapeutic agents useful in the treatment and/or prevention of MDS described herein.

In one embodiment, provided herein is a method of treating, preventing, and/or managing MDS, comprising administering to a patient a lyophilized formulation of Compound 1 provided herein in combination with one or more second active agents, and optionally in combination with radiation therapy, blood transfusions, or surgery. Examples of second active agents are disclosed herein.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a patient with a disease or disorder. A first therapy (e.g., a prophylactic or therapeutic agent such as a lyophilized formulation of Compound 1 provided herein, can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

Administration of a lyophilized formulation of Compound 1 provided herein and one or more second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the cancer being treated.

The route of administration of a lyophilized formulation of Compound 1 is independent of the route of administration of a second therapy. Thus, in accordance with these embodiments, a lyophilized formulation of Compound 1 is administered intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraocularly, via local delivery by catheter or stent, subcutaneously, intraadiposally, intraarticularly, intrathecally, or in a slow release dosage form. In one embodiment, a lyophilized formulation of Compound 1 and a second therapy are administered by the same mode of administration, by IV. In another embodiment, a lyophilized formulation of Compound 1 is administered by one mode of administration, e.g., by IV, whereas the second agent (an anticancer agent) is administered by another mode of administration, e.g., orally.

In one embodiment, the second active agent is administered intravenously or subcutaneously and once or twice daily in an amount of from about 1 to about 1,000 mg, from about 5 to about 500 mg, from about 10 to about 350 mg, or from about 50 to about 200 mg. The specific amount of the second active agent will depend on the specific agent used, the type of disease being treated and/or managed, the severity and stage of disease, and the amount of Compound 1 and any optional additional active agents concurrently administered to the patient.

One or more second active ingredients or agents can be used together with a lyophilized formulation of Compound 1 in the methods and compositions provided herein. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies, particularly, therapeutic antibodies to cancer antigens. Typical large molecule active agents are biological molecules, such as naturally occurring or synthetic or recombinant proteins. Proteins that are particularly useful in the methods and compositions provided herein include proteins that stimulate the survival and/or proliferation of hematopoietic precursor cells and immunologically active poietic cells in vitro or in vivo. Other useful proteins stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; GM-CF and GM-CSF; and EPO.

In certain embodiments, GM-CSF, G-CSF, SCF or EPO is administered subcutaneously during about five days in a four or six week cycle in an amount ranging from about 1 to about 750 mg/m$^2$/day, from about 25 to about 500 mg/m$^2$/day, from about 50 to about 250 mg/m$^2$/day, or from about 50 to about 200 mg/m$^2$/day. In certain embodiments, GM-CSF may be administered in an amount of from about 60 to about 500 mcg/m$^2$ intravenously over 2 hours or from about 5 to about 12 mcg/m$^2$/day subcutaneously. In certain embodiments, G-CSF may be administered subcutaneously in an amount of about 1 mcg/kg/day initially and can be adjusted depending on rise of total granulocyte counts. The maintenance dose of G-CSF may be administered in an amount of about 300 (in smaller patients) or 480 mcg subcutaneously. In certain embodiments, EPO may be administered subcutaneously in an amount of 10,000 Unit 3 times per week.

Particular proteins that can be used in the methods and compositions include, but are not limited to: filgrastim, which is sold in the United States under the trade name Neupogen® (Amgen, Thousand Oaks, Calif.); sargramostim, which is sold in the United States under the trade name Leukine® (Immunex, Seattle, Wash.); and recombinant EPO, which is sold in the United States under the trade name Epogen® (Amgen, Thousand Oaks, Calif.).

Recombinant and mutated forms of GM-CSF can be prepared as described in U.S. Pat. Nos. 5,391,485; 5,393,870; and 5,229,496; all of which are incorporated herein by reference. Recombinant and mutated forms of G-CSF can be prepared as described in U.S. Pat. Nos. 4,810,643; 4,999,291; 5,528,823; and 5,580,755; the entireties of which are incorporated herein by reference.

Also provided for use in combination with a lyophilized formulation of Compound 1 provided herein are native, naturally occurring, and recombinant proteins. Further encompassed are mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., *J. Immunol. Methods* 248:91-101 (2001).

Antibodies that can be used in combination with a lyophilized formulation of Compound 1 provided herein include monoclonal and polyclonal antibodies. Examples of antibodies include, but are not limited to, trastuzumab (Herceptin®), rituximab (Rituxan®), bevacizumab (Avastin™), pertuzumab (Omnitarg™), tositumomab (Bexxar®), edrecolomab (Panorex®), and G250. The lyophilized formulation of Compound 1 can also be combined with, or used in combination with, anti-TNF-α antibodies, and/or anti-EGFR antibodies, such as, for example, Erbitux or panitumumab.

Large molecule active agents may be administered in the form of anti-cancer vaccines. For example, vaccines that secrete, or cause the secretion of, cytokines such as IL-2, G-CSF, and GM-CSF can be used in the methods and pharmaceutical compositions provided. See, e.g., Emens, L. A., et al., *Curr. Opinion Mol. Ther.* 3(1):77-84 (2001).

Second active agents that are small molecules can also be used to alleviate adverse effects associated with the administration of a lyophilized formulation of Compound 1 provided herein. However, like some large molecules, many are believed to be capable of providing a synergistic effect when administered with (e.g., before, after or simultaneously) a lyophilized formulation of Compound 1 provided herein. Examples of small molecule second active agents include, but are not limited to, anti-cancer agents, antibiotics, immunosuppressive agents, and steroids.

In certain embodiments, the second agent is an HSP inhibitor, a proteasome inhibitor, a FLT3 inhibitor or a TOR kinase inhibitor.

Examples of anti-cancer agents to be used within the methods or compositions described herein include, but are not limited to: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; clofarabine; crisnatol mesylate; cyclophosphamide; Ara-C; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; omacetaxine; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sorafenib; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs to be included within the methods or compositions include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-aletheine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomiphene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; Ara-C ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., Gleevec®); imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); $O^6$-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin;

SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

In certain embodiments, a lyophilized formulation of Compound 1 is administered in combination with checkpoint inhibitors. In one embodiment, one checkpoint inhibitor is used in combination with a lyophilized formulation of Compound 1 in connection with the methods provided herein. In another embodiment, two checkpoint inhibitors are used in combination with a lyophilized formulation of Compound 1 in connection with the methods provided herein. In yet another embodiment, three or more checkpoint inhibitors are used in combination with a lyophilized formulation of Compound 1 in connection with the methods provided herein.

As used herein, the term "immune checkpoint inhibitor" or "checkpoint inhibitor" refers to molecules that totally or partially reduce, inhibit, interfere with or modulate one or more checkpoint proteins. Without being limited by a particular theory, checkpoint proteins regulate T-cell activation or function. Numerous checkpoint proteins are known, such as CTLA-4 and its ligands CD80 and CD86; and PD-1 with its ligands PD-L1 and PD-L2 (Pardoll, Nature Reviews Cancer, 2012, 12, 252-264). These proteins appear responsible for co-stimulatory or inhibitory interactions of T-cell responses. Immune checkpoint proteins appear to regulate and maintain self-tolerance and the duration and amplitude of physiological immune responses. Immune checkpoint inhibitors include antibodies or are derived from antibodies.

In one embodiment, the checkpoint inhibitor is a CTLA-4 inhibitor. In one embodiment, the CTLA-4 inhibitor is an anti-CTLA-4 antibody. Examples of anti-CTLA-4 antibodies include, but are not limited to, those described in U.S. Pat. Nos. 5,811,097; 5,811,097; 5,855,887; 6,051,227; 6,207,157; 6,682,736; 6,984,720; and 7,605,238, all of which are incorporated herein in their entireties. In one embodiment, the anti-CTLA-4 antibody is tremelimumab (also known as ticilimumab or CP-675,206). In another embodiment, the anti-CTLA-4 antibody is ipilimumab (also known as MDX-010 or MDX-101). Ipilimumab is a fully human monoclonal IgG antibody that binds to CTLA-4. Ipilimumab is marketed under the trade name Yervoy™.

In one embodiment, the checkpoint inhibitor is a PD-1/PD-L1 inhibitor. Examples of PD-1/PD-L1 inhibitors include, but are not limited to, those described in U.S. Pat. Nos. 7,488,802; 7,943,743; 8,008,449; 8,168,757; 8,217, 149, and PCT Patent Application Publication Nos. WO2003042402, WO2008156712, WO2010089411, WO2010036959, WO2011066342, WO2011159877, WO2011082400, and WO2011161699, all of which are incorporated herein in their entireties.

In one embodiment, the checkpoint inhibitor is a PD-1 inhibitor. In one embodiment, the PD-1 inhibitor is an anti-PD-1 antibody. In one embodiment, the anti-PD-1 antibody is nivolumab (also known as ONO-4538, BMS-936558, or MDX1106) or pembrolizumab (also known as MK-3475, SCH 900475, or lambrolizumab). In one embodiment, the anti-PD-1 antibody is nivolumab. Nivolumab is a human IgG4 anti-PD-1 monoclonal antibody, and is marketed under the trade name Opdivo™. In another embodiment, the anti-PD-1 antibody is pembrolizumab. Pembrolizumab is a humanized monoclonal IgG4 antibody and is marketed under the trade name Keytruda™. In yet another embodiment, the anti-PD-1 antibody is CT-011, a humanized antibody. CT-011 administered alone has failed to show response in treating acute myeloid leukemia (AML) at relapse. In yet another embodiment, the anti-PD-1 antibody is AMP-224, a fusion protein.

In one embodiment, the checkpoint inhibitor is a PD-L1 inhibitor. In one embodiment, the PD-L1 inhibitor is an anti-PD-L1 antibody. In one embodiment, the anti-PD-L1 antibody is MEDI4736 (durvalumab). In another embodiment, the anti-PD-L1 antibody is BMS-936559 (also known as MDX-1105-01). In yet another embodiment, the PD-L1 inhibitor is atezolizumab (also known as MPDL3280A, and Tecentriq®).

In one embodiment, the checkpoint inhibitor is a PD-L2 inhibitor. In one embodiment, the PD-L2 inhibitor is an anti-PD-L2 antibody. In one embodiment, the anti-PD-L2 antibody is rHIgM12B7A.

In one embodiment, the checkpoint inhibitor is a lymphocyte activation gene-3 (LAG-3) inhibitor. In one embodiment, the LAG-3 inhibitor is IMP321, a soluble Ig fusion protein (Brignone et al., J. Immunol., 2007, 179, 4202-4211). In another embodiment, the LAG-3 inhibitor is BMS-986016.

In one embodiment, the checkpoint inhibitors is a B7 inhibitor. In one embodiment, the B7 inhibitor is a B7-H3 inhibitor or a B7-H4 inhibitor. In one embodiment, the B7-H3 inhibitor is MGA271, an anti-B7-H3 antibody (Loo et al., Clin. Cancer Res., 2012, 3834).

In one embodiment, the checkpoint inhibitors is a TIM3 (T-cell immunoglobulin domain and mucin domain 3) inhibitor (Fourcade et al., J. Exp. Med., 2010, 207, 2175-86; Sakuishi et al., J. Exp. Med., 2010, 207, 2187-94).

In one embodiment, the checkpoint inhibitor is an OX40 (CD134) agonist. In one embodiment, the checkpoint inhibitor is an anti-OX40 antibody. In one embodiment, the anti-OX40 antibody is anti-OX-40. In another embodiment, the anti-OX40 antibody is MEDI6469.

In one embodiment, the checkpoint inhibitor is a GITR agonist. In one embodiment, the checkpoint inhibitor is an anti-GITR antibody. In one embodiment, the anti-GITR antibody is TRX518.

In one embodiment, the checkpoint inhibitor is a CD137 agonist. In one embodiment, the checkpoint inhibitor is an anti-CD137 antibody. In one embodiment, the anti-CD137 antibody is urelumab. In another embodiment, the anti-CD137 antibody is PF-05082566.

In one embodiment, the checkpoint inhibitor is a CD40 agonist. In one embodiment, the checkpoint inhibitor is an anti-CD40 antibody. In one embodiment, the anti-CD40 antibody is CF-870,893.

In one embodiment, the checkpoint inhibitor is recombinant human interleukin-15 (rhIL-15).

In one embodiment, the checkpoint inhibitor is an IDO inhibitor. In one embodiment, the IDO inhibitor is INCB024360. In another embodiment, the IDO inhibitor is indoximod.

In certain embodiments, the combination therapies provided herein include two or more of the checkpoint inhibitors described herein (including checkpoint inhibitors of the same or different class). Moreover, the combination therapies described herein can be used in combination with second active agents as described herein where appropriate for treating diseases described herein and understood in the art.

In certain embodiments, Compound 1 can be used in combination with one or more immune cells expressing one or more chimeric antigen receptors (CARs) on their surface (e.g., a modified immune cell). Generally, CARs comprise an extracellular domain from a first protein e.g., an antigen-binding protein), a transmembrane domain, and an intracellular signaling domain. In certain embodiments, once the extracellular domain binds to a target protein such as a tumor-associated antigen (TAA) or tumor-specific antigen (TSA), a signal is generated via the intracellular signaling domain that activates the immune cell, e.g., to target and kill a cell expressing the target protein.

Extracellular domains: The extracellular domains of the CARs bind to an antigen of interest. In certain embodiments, the extracellular domain of the CAR comprises a receptor, or a portion of a receptor, that binds to said antigen. In certain embodiments, the extracellular domain comprises, or is, an antibody or an antigen-binding portion thereof. In specific embodiments, the extracellular domain comprises, or is, a single chain Fv (scFv) domain. The single-chain Fv domain can comprise, for example, a $V_L$ linked to $V_H$ by a flexible linker, wherein said $V_L$ and $V_H$ are from an antibody that binds said antigen.

In certain embodiments, the antigen recognized by the extracellular domain of a polypeptide described herein is a tumor-associated antigen (TAA) or a tumor-specific antigen (TSA). In various specific embodiments, the tumor-associated antigen or tumor-specific antigen is, without limitation, Her2, prostate stem cell antigen (PSCA), alpha-fetoprotein (AFP), carcinoembryonic antigen (CEA), cancer antigen-125 (CA-125), CA19-9, calretinin, MUC-1, B cell maturation antigen (BCMA), epithelial membrane protein (EMA), epithelial tumor antigen (ETA), tyrosinase, melanoma-24 associated antigen (MAGE), CD19, CD22, CD27, CD30, CD34, CD45, CD70, CD99, CD117, EGFRvIII (epidermal growth factor variant III), mesothelin, PAP (prostatic acid phosphatase), prostein, TARP (T cell receptor gamma alternate reading frame protein), Trp-p8, STEAP1 (six-transmembrane epithelial antigen of the prostate 1), chromogranin, cytokeratin, desmin, glial fibrillary acidic protein (GFAP), gross cystic disease fluid protein (GCDFP-15), HMB-45 antigen, protein melan-A (melanoma antigen recognized by T lymphocytes; MART-I), myo-D1, muscle-specific actin (MSA), neurofilament, neuron-specific enolase (NSE), placental alkaline phosphatase, synaptophysis, thyroglobulin, thyroid transcription factor-1, the dimeric form of the pyruvate kinase isoenzyme type M2 (tumor M2-PK), an abnormal ras protein, or an abnormal p53 protein. In certain other embodiments, the TAA or TSA recognized by the extracellular domain of a CAR is integrin αvβ3 (CD61), galactin, or Ral-B.

In certain embodiments, the TAA or TSA recognized by the extracellular domain of a CAR is a cancer/testis (CT) antigen, e.g., BAGE, CAGE, CTAGE, FATE, GAGE, HCA661, HOM-TES-85, MAGEA, MAGEB, MAGEC, NA88, NY-ES0-1, NY-SAR-35, OY-TES-1, SPANXBI, SPA17, SSX, SYCPI, or TPTE.

In certain other embodiments, the TAA or TSA recognized by the extracellular domain of a CAR is a carbohydrate or ganglioside, e.g., fuc-GMI, GM2 (oncofetal antigen-immunogenic-1; OFA-I-1); GD2 (OFA-I-2), GM3, GD3, and the like.

In certain other embodiments, the TAA or TSA recognized by the extracellular domain of a CAR is alpha-actinin-4, Bage-1, BCR-ABL, Bcr-Abl fusion protein, beta-catenin, CA 125, CA 15-3 (CA 27.29\BCAA), CA 195, CA 242, CA-50, CAM43, Casp-8, cdc27, cdk4, cdkn2a, CEA, coa-1, dek-can fusion protein, EBNA, EF2, Epstein Barr virus antigens, ETV6-AML1 fusion protein, HLA-A2, HLA-All, hsp70-2, KIAA0205, Mart2, Mum-1, 2, and 3, neo-PAP, myosin class I, OS-9, pml-RARα fusion protein, PTPRK, K-ras, N-ras, triosephosphate isomerase, Gage 3,4,5,6,7, GnTV, Herv-K-mel, Lage-1, NA-88, NY-Eso-1/Lage-2, SP17, SSX-2, TRP2-Int2, gp100 (Pmel17), tyrosinase, TRP-1, TRP-2, MAGE-1, MAGE-3, RAGE, GAGE-1, GAGE-2, p15(58), RAGE, SCP-1, Hom/Mel-40, PRAME, p53, HRas, HER-2/neu, E2A-PRL, H4-RET, IGH-IGK, MYL-RAR, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, 13-Catenin, Mum-1, p16, TAGE, PSMA, CT7, telomerase, 43-9F, 5T4, 791Tgp72, 13HCG, BCA225, BTAA, CD68\KP1, C0-029, FGF-5, G250, Ga733 (EpCAM), HTgp-175, M344, MA-50, MG7-Ag, MOV18, NB\70K, NY-C0-1, RCAS1, SDCCAG16, TA-90, TAAL6, TAG72, TLP, or TPS.

In various specific embodiments, the tumor-associated antigen or tumor-specific antigen is an AML-related tumor antigens, as described in S. Anguille et al, *Leukemia* (2012), 26, 2186-2196.

Other tumor-associated and tumor-specific antigens are known to those in the art.

Receptors, antibodies, and scFvs that bind to TSAs and TAAs, useful in constructing chimeric antigen receptors, are known in the art, as are nucleotide sequences that encode them.

In certain specific embodiments, the antigen recognized by the extracellular domain of a chimeric antigen receptor is an antigen not generally considered to be a TSA or a TAA, but which is nevertheless associated with tumor cells, or damage caused by a tumor. In certain embodiments, for example, the antigen is, e.g., a growth factor, cytokine or interleukin, e.g., a growth factor, cytokine, or interleukin associated with angiogenesis or vasculogenesis. Such growth factors, cytokines, or interleukins can include, e.g., vascular endothelial growth factor (VEGF), basic fibroblast growth factor (bFGF), platelet-derived growth factor (PDGF), hepatocyte growth factor (HGF), insulin-like growth factor (IGF), or interleukin-8 (IL-8). Tumors can also create a hypoxic environment local to the tumor. As such, in other specific embodiments, the antigen is a hypoxia-associated factor, e.g., HIF-1α, HIF-1β, HIF-2α, HIF-2β, HIF-3α, or HIF-3β. Tumors can also cause localized damage to normal tissue, causing the release of molecules known as damage associated molecular pattern molecules (DAMPs; also known as alarmins). In certain other specific embodiments, therefore, the antigen is a DAMP, e.g., a heat shock protein, chromatin-associated protein high mobility group box 1 (HMGB 1), S100A8 (MRP8, calgranulin A), S100A9 (MRP14, calgranulin B), serum amyloid A (SAA), or can be a deoxyribonucleic acid, adenosine triphosphate, uric acid, or heparin sulfate.

Transmembrane domain: In certain embodiments, the extracellular domain of the CAR is joined to the transmembrane domain of the polypeptide by a linker, spacer or hinge polypeptide sequence, e.g., a sequence from CD28 or a sequence from CTLA4. The transmembrane domain can be obtained or derived from the transmembrane domain of any transmembrane protein, and can include all or a portion of such transmembrane domain. In specific embodiments, the transmembrane domain can be obtained or derived from, e.g., CD8, CD16, a cytokine receptor, and interleukin receptor, or a growth factor receptor, or the like.

Intracellular signaling domains: In certain embodiments, the intracellular domain of a CAR is or comprises an intracellular domain or motif of a protein that is expressed on the surface of T cells and triggers activation and/or proliferation of said T cells. Such a domain or motif is able to transmit a primary antigen-binding signal that is necessary for the activation of a T lymphocyte in response to the antigen's binding to the CAR's extracellular portion. Typically, this domain or motif comprises, or is, an ITAM (immunoreceptor tyrosine-based activation motif). ITAM-containing polypeptides suitable for CARs include, for example, the zeta CD3 chain (CD3L) or ITAM-containing portions thereof. In a specific embodiment, the intracellular domain is a CD3 intracellular signaling domain. In other specific embodiments, the intracellular domain is from a lymphocyte receptor chain, a TCR/CD3 complex protein, an Fe receptor subunit or an IL-2 receptor subunit. In certain embodiments, the CAR additionally comprises one or more co-stimulatory domains or motifs, e.g., as part of the intracellular domain of the polypeptide. The one or more co-stimulatory domains or motifs can be, or can comprise comprise, one or more of a co-stimulatory CD27 polypeptide sequence, a co-stimulatory CD28 polypeptide sequence, a co-stimulatory OX40 (CD134) polypeptide sequence, a co-stimulatory 4-1BB (CD137) polypeptide sequence, or a co-stimulatory inducible T-cell co-stimulatory (ICOS) polypeptide sequence, or other costimulatory domain or motif, or any combination thereof.

The CAR may also comprise a T cell survival motif. The T cell survival motif can be any polypeptide sequence or motif that facilitates the survival of the T lymphocyte after stimulation by an antigen. In certain embodiments, the T cell survival motif is, or is derived from, CD3, CD28, an intracellular signaling domain of IL-7 receptor (IL-7R), an intracellular signaling domain of IL-12 receptor, an intracellular signaling domain of IL-15 receptor, an intracellular signaling domain of IL-21 receptor, or an intracellular signaling domain of transforming growth factor β (TGFβ) receptor.

The modified immune cells expressing the CARs can be, e.g., T lymphocytes (T cells, e.g., CD4+ T cells or CD8+ T cells), cytotoxic lymphocytes (CTLs) or natural killer (NK) cells. T lymphocytes used in the compositions and methods provided herein may be naive T lymphocytes or MHC-restricted T lymphocytes. In certain embodiments, the T lymphocytes are tumor infiltrating lymphocytes (TILs). In certain embodiments, the T lymphocytes have been isolated from a tumor biopsy, or have been expanded from T lymphocytes isolated from a tumor biopsy. In certain other embodiments, the T cells have been isolated from, or are expanded from T lymphocytes isolated from, peripheral blood, cord blood, or lymph. Immune cells to be used to generate modified immune cells expressing a CAR can be isolated using art-accepted, routine methods, e.g., blood collection followed by apheresis and optionally antibody-mediated cell isolation or sorting.

The modified immune cells are preferably autologous to an individual to whom the modified immune cells are to be administered. In certain other embodiments, the modified immune cells are allogeneic to an individual to whom the modified immune cells are to be administered. Where allogeneic T lymphocytes or NK cells are used to prepare modified T lymphocytes, it is preferable to select T lymphocytes or NK cells that will reduce the possibility of graft-versus-host disease (GVHD) in the individual. For example, in certain embodiments, virus-specific T lymphocytes are selected for preparation of modified T lymphocytes; such lymphocytes will be expected to have a greatly reduced native capacity to bind to, and thus become activated by, any recipient antigens. In certain embodiments, recipient-mediated rejection of allogeneic T lymphocytes can be reduced by co-administration to the host of one or more immunosuppressive agents, e.g., cyclosporine, tacrolimus, sirolimus, cyclophosphamide, or the like.

T lymphocytes, e.g., unmodified T lymphocytes, or T lymphocytes expressing CD3 and CD28, or comprising a polypeptide comprising a CD3ζ signaling domain and a CD28 co-stimulatory domain, can be expanded using antibodies to CD3 and CD28, e.g., antibodies attached to beads; see, e.g., U.S. Pat. Nos. 5,948,893; 6,534,055; 6,352,694; 6,692,964; 6,887,466; and 6,905,681.

The modified immune cells, e.g., modified T lymphocytes, can optionally comprise a "suicide gene" or "safety switch" that enables killing of substantially all of the modified immune cells when desired. For example, the modified T lymphocytes, in certain embodiments, can comprise an HSV thymidine kinase gene (HSV-TK), which causes death of the modified T lymphocytes upon contact with gancyclovir. In another embodiment, the modified T lymphocytes comprise an inducible caspase, e.g., an inducible caspase 9 (icaspase9), e.g., a fusion protein between caspase 9 and human FK506 binding protein allowing for dimerization using a specific small molecule pharmaceutical. See Straathof et al., *Blood* 105(11):4247-4254 (2005).

Specific second active agents particularly useful in the methods or compositions include, but are not limited to, rituximab, oblimersen (Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, interferon alpha, pegylated interferon alpha (e.g., PEG INTRON-A), capecitabine, cisplatin, thiotepa, fludarabine, carboplatin, liposomal daunorubicin, Ara-C, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, and etoposide.

In certain embodiments of the methods provided herein, use of a second active agent in combination with a lyophilized formulation of Compound 1 provided herein may be modified or delayed during or shortly following administration of a lyophilized formulation of Compound 1 provided herein as deemed appropriate by the practitioner of skill in the art. In certain embodiments, subjects being administered a lyophilized formulation of Compound 1 provided herein alone or in combination with other therapies may receive supportive care including antiemetics, myeloid growth factors, and transfusions of platelets, when appropriate. In some embodiments, subjects being administered a lyophilized formulation of Compound 1 provided herein may be administered a growth factor as a second active agent according to the judgment of the practitioner of skill in the art. In some embodiments, provided is administration of a lyophilized formulation of Compound 1 provided herein in combination with erythropoietin or darbepoetin (Aranesp).

In certain embodiments, a lyophilized formulation of Compound 1 provided herein is administered with gemcitabine, cisplatinum, 5-fluorouracil, mitomycin, methotrexate, vinblastine, doxorubicin, carboplatin, thiotepa, paclitaxel or docetaxel to patients with locally advanced or metastatic transitional cell bladder cancer.

In certain embodiments, a lyophilized formulation of Compound 1 provided herein is administered in combination with a second active ingredient as follows: temozolomide to pediatric patients with relapsed or progressive brain tumors or recurrent neuroblastoma; celecoxib, etoposide and cyclophosphamide for relapsed or progressive CNS cancer; temodar to patients with recurrent or progressive meningioma, malignant meningioma, hemangiopericytoma, multiple brain metastases, relapsed brain tumors, or newly diagnosed glioblastoma multiforms; irinotecan to patients with recurrent glioblastoma; carboplatin to pediatric patients with brain stem glioma; procarbazine to pediatric patients with progressive malignant gliomas; cyclophosphamide to patients with poor prognosis malignant brain tumors, newly diagnosed or recurrent glioblastoma multiforms; Gliadel® for high grade recurrent malignant gliomas; temozolomide and tamoxifen for anaplastic astrocytoma; or topotecan for gliomas, glioblastoma, anaplastic astrocytoma or anaplastic oligodendroglioma.

In certain embodiments, a lyophilized formulation of Compound 1 provided herein is administered with methotrexate, cyclophosphamide, 5-fluorouracil, taxane, everolimus, abraxane, lapatinib, herceptin, pamidronate disodium, eribulin mesylate, everolimus, gemcitabine, palbociclib, ixabepilone, kadcyla, pertuzumab, theotepa, aromatase inhibitors, exemestane, selective estrogen modulators, estrogen receptor antagonists, anthracyclines, emtansine, and/or pexidartinib to patients with metastatic breast cancer.

In certain embodiments, a lyophilized formulation of Compound 1 provided herein is administered with temozolomide, doxorubicin (Adriamycin), fluorouracil (Adrucil, 5-fluorouracil), or streptozocin (Zanosar) to patients with neuroendocrine tumors.

In certain embodiments, a lyophilized formulation of Compound 1 provided herein is administered with methotrexate, gemcitabine, cisplatin, cetuximab, 5-fluorouracil, bleomycin, docetaxel or carboplatin to patients with recurrent or metastatic head or neck cancer.

In certain embodiments, a lyophilized formulation of Compound 1 provided herein is administered with gemcitabine, abraxane, 5-fluorouracil, afinitor, irinotecan, mitomycin C, sunitinib or tarceva to patients with pancreatic cancer.

In certain embodiments, a lyophilized formulation of Compound 1 provided herein is administered to patients with colon cancer in combination with ARISA®, avastatin, oxaliplatin, 5-fluorouracil, irinotecan, capecitabine, cetuximab, ramucirumab, panitumumab, bevacizumab, leucovorin calcium, lonsurf, regorafenib, ziv-aflibercept, taxol, and/or taxotere.

In certain embodiments, a lyophilized formulation of Compound 1 provided herein is administered with capecitabine and/or vemurafenib to patients with refractory colorectal cancer or patients who fail first line therapy or have poor performance in colon or rectal adenocarcinoma.

In certain embodiments, a lyophilized formulation of Compound 1 provided herein is administered in combination with fluorouracil, leucovorin, and irinotecan to patients with Dukes C & D colorectal cancer or to patients who have been previously treated for metastatic colorectal cancer.

In certain embodiments, a lyophilized formulation of Compound 1 provided herein is administered to patients with refractory colorectal cancer in combination with capecitabine, xeloda, and/or irinotecan.

In certain embodiments, a lyophilized formulation of Compound 1 provided herein is administered with capecitabine and irinotecan to patients with refractory colorectal cancer or to patients with unresectable or metastatic colorectal carcinoma.

In certain embodiments, a lyophilized formulation of Compound 1 provided herein is administered alone or in combination with interferon alpha or capecitabine to patients with unresectable or metastatic hepatocellular carcinoma; or with cisplatin and thiotepa, or with sorafenib tosylate to patients with primary or metastatic liver cancer.

In certain embodiments, a lyophilized formulation of Compound 1 provided herein is administered in combination with doxorubicin, paclitaxel, vinblastine or pegylated interferon alpha to patients with Kaposi's sarcoma.

In certain embodiments, a lyophilized formulation of Compound 1 provided herein is administered in combination with arsenic trioxide, fludarabine, carboplatin, daunorubicin, cyclophosphamide, cytarabine, doxorubicin, idarubicin, mitoxantrone hydrochloride, thioguanine, vincritine, and/or topotecan to patients with acute myeloid leukemia, including refractory or relapsed or high-risk acute myeloid leukemia.

In certain embodiments, a lyophilized formulation of Compound 1 provided herein is administered in combination with liposomal daunorubicin, topotecan and/or cytarabine to patients with unfavorable karotype acute myeloblastic leukemia.

In certain embodiments, a lyophilized formulation of Compound 1 provided herein is administered in combination with methotrexate, mechlorethamine hydrochloride, afatinib dimaleate, pemetrexed, bevacizumab, carboplatin, cisplatin, ceritinib, crizotinib, ramucirumab, pembrolizumab, docetaxel, vinorelbine tartrate, gemcitabine, abraxane, erlotinib, geftinib, and/or irinotecan to patients with non-small cell lung cancer.

In certain embodiments, a lyophilized formulation of Compound 1 provided herein is administered in combination with carboplatin and irinotecan to patients with non-small cell lung cancer.

In certain embodiments, a lyophilized formulation of Compound 1 provided herein is administered with doxetaxol to patients with non-small cell lung cancer who have been previously treated with carbo/etoposide and radiotherapy.

In certain embodiments, a lyophilized formulation of Compound 1 provided herein is administered in combination with carboplatin and/or taxotere, or in combination with carboplatin, paclitaxel and/or thoracic radiotherapy to patients with non-small cell lung cancer.

In certain embodiments, a lyophilized formulation of Compound 1 provided herein is administered in combination with taxotere to patients with stage IIIB or IV non-small cell lung cancer.

In certain embodiments, a lyophilized formulation of Compound 1 provided herein is administered in combination with oblimersen (Genasense®), methotrexate, mechlorethamine hydrochloride, etoposide, topotecan or doxorubicin to patients with small cell lung cancer.

In certain embodiments, a lyophilized formulation of Compound 1 provided herein is administered in combination with ABT-737 (Abbott Laboratories) and/or obatoclax (GX15-070) to patients with lymphoma and other blood cancers.

In certain embodiments, a lyophilized formulation of Compound 1 provided herein is administered alone or in combination with a second active ingredient such as vinblastine or fludarabine adcetris, ambochlorin, becenum, bleomycin, brentuximab vedotin, carmustinem chlorambucil, cyclophosphamide, dacarbazine, doxorubicin, lomustine, matulane, mechlorethamine hydrochloride, prednisone, procarbazine hydrochloride or vincristine to patients with various types of lymphoma, including, but not limited to, Hodgkin's lymphoma, non-Hodgkin's lymphoma, cutaneous T-Cell lymphoma, cutaneous B-Cell lymphoma, diffuse large B-Cell lymphoma or relapsed or refractory low grade follicular lymphoma.

In certain embodiments, a lyophilized formulation of Compound 1 provided herein is administered in combination with taxotere, dabrafenib, imlygic, ipilimumab, pembrolizumab, nivolumab, trametinib, vemurafenib, talimogene laherparepvec, IL-2, IFN, GM-CSF, and/or dacarbazine to patients with various types or stages of melanoma.

In certain embodiments, a lyophilized formulation of Compound 1 provided herein is administered alone or in combination with vinorelbine to patients with malignant mesothelioma, or stage IIIB non-small cell lung cancer with pleural implants or malignant pleural effusion mesothelioma syndrome.

In certain embodiments, a lyophilized formulation of Compound 1 provided herein is administered to patients with various types or stages of multiple myeloma in combination with dexamethasone, zoledronic acid, palmitronate, GM-CSF, biaxin, vinblastine, melphalan, busulphan, cyclophosphamide, IFN, prednisone, bisphosphonate, celecoxib, arsenic trioxide, PEG INTRON-A, vincristine, becenum, bortezomib, carfilzomib, doxorubicin, panobinostat, lenalidomide, pomalidomide, thalidomide, mozobil or a combination thereof.

In certain embodiments, a lyophilized formulation of Compound 1 provided herein is administered to patients with various types or stages of multiple myeloma in combination with chimeric antigen receptor (CAR) T-cells.

In certain embodiments, a lyophilized formulation of Compound 1 provided herein is administered to patients with relapsed or refractory multiple myeloma in combination with doxorubicin (Doxil®), vincristine and/or dexamethasone (Decadron®).

In certain embodiments, a lyophilized formulation of Compound 1 provided herein is administered to patients with various types or stages of ovarian cancer such as peritoneal carcinoma, papillary serous carcinoma, refractory ovarian cancer or recurrent ovarian cancer, in combination with taxol, carboplatin, doxorubicin, gemcitabine, cisplatin, xeloda, paclitaxel, dexamethasone, avastin, cyclophosphamide, topotecan, olaparib, thiotepa, or a combination thereof.

In certain embodiments, a lyophilized formulation of Compound 1 provided herein is administered to patients with various types or stages of prostate cancer, in combination with xeloda, 5 FU/LV, gemcitabine, irinotecan plus gemcitabine, cyclophosphamide, vincristine, dexamethasone, GM-CSF, celecoxib, taxotere, ganciclovir, paclitaxel, adriamycin, docetaxel, estramustine, Emcyt, denderon, zytiga, bicalutamide, cabazitaxel, degarelix, enzalutamide, zoladex, leuprolide acetate, mitoxantrone hydrochloride, prednisone, sipuleucel-T, radium 223 dichloride, or a combination thereof.

In certain embodiments, a lyophilized formulation of Compound 1 provided herein is administered to patients with various types or stages of renal cell cancer, in combination with capecitabine, IFN, tamoxifen, IL-2, GM-CSF, Celebrex®, or a combination thereof.

In certain embodiments, a lyophilized formulation of Compound 1 provided herein is administered to patients with various types or stages of gynecologic, uterus or soft tissue sarcoma cancer in combination with IFN, dactinomycin, doxorubicin, imatinib mesylate, pazopanib, hydrochloride, trabectedin, a COX-2 inhibitor such as Celebrex®, and/or sulindac.

In certain embodiments, a lyophilized formulation of Compound 1 provided herein is administered to patients with various types or stages of solid tumors in combination with celebrex, etoposide, cyclophosphamide, docetaxel, apecitabine, IFN, tamoxifen, IL-2, GM-CSF, or a combination thereof.

In certain embodiments, a lyophilized formulation of Compound 1 provided herein is administered to patients with scleroderma or cutaneous vasculitis in combination with celebrex, etoposide, cyclophosphamide, docetaxel, apecitabine, IFN, tamoxifen, IL-2, GM-CSF, or a combination thereof.

In certain embodiments, a lyophilized formulation of Compound 1 provided herein is administered to patients with MDS in combination with azacitidine, cytarabine, daunorubicin, decitabine, idarubicin, lenalidomide or a combination thereof.

Also encompassed herein is a method of increasing the dosage of an anti-cancer drug or agent that can be safely and effectively administered to a patient, which comprises administering to the patient (e.g., a human) a lyophilized formulation of Compound 1 provided herein. Patients that can benefit by this method are those likely to suffer from an adverse effect associated with anti-cancer drugs for treating a specific cancer of the skin, subcutaneous tissue, lymph nodes, brain, lung, liver, bone, intestine, colon, heart, pancreas, adrenal, kidney, prostate, breast, colorectal, or combinations thereof. The administration of a lyophilized formulation of Compound 1 provided herein alleviates or reduces adverse effects which are of such severity that it would otherwise limit the amount of anti-cancer drug.

In one embodiment, a lyophilized formulation of Compound 1 provided herein is administered daily in an amount ranging from about 0.1 to about 150 mg, from about 1 to about 50 mg, from about 2 to about 25 mg, or from about 1 to about 10 mg prior to, during, or after the occurrence of the adverse effect associated with the administration of an anti-cancer drug to a patient. In certain embodiments, a lyophilized formulation of Compound 1 provided herein is administered in combination with specific agents such as heparin, aspirin, coumadin, or G-CSF to avoid adverse effects that are associated with anti-cancer drugs such as but not limited to neutropenia or thrombocytopenia.

In one embodiment, a lyophilized formulation of Compound 1 provided herein is administered to patients with diseases and disorders associated with or characterized by, undesired angiogenesis in combination with additional active ingredients, including, but not limited to, anti-cancer drugs, anti-inflammatories, antihistamines, antibiotics, and steroids.

In another embodiment, encompassed herein is a method of treating, preventing and/or managing cancer, which comprises administering a lyophilized formulation of Compound 1 provided herein in conjunction with (e.g. before, during, or after) conventional therapy including, but not limited to, surgery, immunotherapy, biological therapy, radiation therapy, or other non-drug based therapy presently used to treat, prevent and/or manage cancer. The combined use of the compound provided herein and conventional therapy may provide a unique treatment regimen that is unexpectedly effective in certain patients. Without being limited by theory, it is believed that a lyophilized formulation of Compound 1 provided herein may provide additive or synergistic effects when given concurrently with conventional therapy.

As discussed elsewhere herein, encompassed herein is a method of reducing, treating and/or preventing adverse or undesired effects associated with conventional therapy including, but not limited to, surgery, chemotherapy, radiation therapy, hormonal therapy, biological therapy and immunotherapy. A lyophilized formulation of Compound 1 provided herein and other active ingredient can be administered to a patient prior to, during, or after the occurrence of the adverse effect associated with conventional therapy.

In certain embodiments, the methods provided herein comprise administration of calcium, calcitriol, and vitamin D supplementation with a lyophilized formulation of Compound 1. In certain embodiments, the methods provided herein comprise administration of calcium, calcitriol, and vitamin D supplementation prior to the treatment with a lyophilized formulation of Compound 1.

In certain embodiments, calcium supplementation is administered to deliver at least 1200 mg of elemental calcium per day given in divided doses. In certain embodiments, calcium supplementation is administered as calcium carbonate in a dose of 500 mg administered three times a day per orally (PO).

In certain embodiments, calcitriol supplementation is administered to deliver 0.25 µg calcitriol (PO) once daily.

In certain embodiments, vitamin D supplementation is administered to deliver about 500 IU to about 5,000 IU vitamin D once daily. In certain embodiments, vitamin D supplementation is administered to deliver about 1,000 IU vitamin D once daily. In certain embodiments, vitamin D supplementation is administered to deliver about 50,000 IU vitamin D weekly. In certain embodiments, vitamin D supplementation is administered to deliver about 1,000 IU vitamin D2 or D3 once daily. In certain embodiments, vitamin D supplementation is administered to deliver about 50,000 IU vitamin D2 or D3 weekly.

In certain embodiments, a lyophilized formulation of Compound 1 provided herein and doxetaxol are administered to patients with non-small cell lung cancer who were previously treated with carbo/VP 16 and radiotherapy.

6.6.2 Use With Transplantation Therapy

The lyophilized formulation of Compound 1 provided herein provided herein can be used to reduce the risk of Graft Versus Host Disease (GVHD). Therefore, encompassed herein is a method of treating, preventing and/or managing cancer, which comprises administering a lyophilized formulation of Compound 1 provided herein in conjunction with transplantation therapy.

As those of ordinary skill in the art are aware, the treatment of cancer is often based on the stages and mechanism of the disease. For example, as inevitable leukemic transformation develops in certain stages of cancer, transplantation of peripheral blood stem cells, hematopoietic stem cell preparation or bone marrow may be necessary. The combined use of a lyophilized formulation of Compound 1 provided herein provided herein and transplantation therapy provides a unique and unexpected synergism. In particular, a lyophilized formulation of Compound 1 provided herein exhibits immunomodulatory activity that may provide additive or synergistic effects when given concurrently with transplantation therapy in patients with cancer.

The lyophilized formulation of Compound 1 provided herein can work in combination with transplantation therapy reducing complications associated with the invasive procedure of transplantation and risk of GVHD. Encompassed herein is a method of treating, preventing and/or managing cancer which comprises administering to a patient (e.g., a human) lyophilized formulation of Compound 1 provided herein before, during, or after the transplantation of umbilical cord blood, placental blood, peripheral blood stem cell, hematopoietic stem cell preparation, or bone marrow. Some examples of stem cells suitable for use in the methods provided herein are disclosed in U.S. Pat. No. 7,498,171, the disclosure of which is incorporated herein by reference in its entirety.

In one embodiment, a lyophilized formulation of Compound 1 provided herein is administered to patients with acute myeloid leukemia before, during, or after transplantation.

In one embodiment, a lyophilized formulation of Compound 1 provided herein is administered to patients with multiple myeloma before, during, or after the transplantation of autologous peripheral blood progenitor cell.

In one embodiment, a lyophilized formulation of Compound 1 provided herein is administered to patients with NHL (e.g., DLBCL) before, during, or after the transplantation of autologous peripheral blood progenitor cell.

6.6.3 Cycling Therapy

In certain embodiments, the prophylactic or therapeutic agents provided herein are cyclically administered to a patient. Cycling therapy involves the administration of an active agent for a period of time, followed by a rest for a period of time, and repeating this sequential administration. Cycling therapy can reduce the development of resistance to one or more of the therapies, avoid, or reduce the side effects of one of the therapies, and/or improves the efficacy of the treatment.

Consequently, in certain embodiments, a lyophilized formulation of Compound 1 provided herein provided herein is administered daily in a single or divided dose in a four to six week cycle with a rest period of about a week or two weeks. In certain embodiments, a lyophilized formulation of Compound 1 provided herein provided herein is administered daily in a single or divided doses for one to ten consecutive days of a 28 day cycle, then a rest period with no administration for rest of the 28 day cycle. The cycling method further allows the frequency, number, and length of dosing cycles to be increased. Thus, encompassed herein in certain embodiments is the administration of a lyophilized formulation of Compound 1 provided herein for more cycles than are typical when it is administered alone. In certain embodiments, a lyophilized formulation of Compound 1 provided herein is administered for a greater number of cycles that would typically cause dose-limiting toxicity in a patient to whom a second active ingredient is not also being administered.

In one embodiment, a lyophilized formulation of Compound 1 provided herein is administered daily and continuously for three or four weeks at a dose of from about 0.1 to about 150 mg/d followed by a break of one or two weeks.

In another embodiment, a lyophilized formulation of Compound 1 provided herein is administered intravenously and a second active ingredient is administered orally, with administration of the lyophilized formulation of Compound 1 occurring 30 to 60 minutes prior to a second active ingredient, during a cycle of four to six weeks. In certain embodiments, the combination of a lyophilized formulation of Compound 1 provided herein and a second active ingredient is administered by intravenous infusion over about 90 minutes every cycle. In certain embodiments, one cycle comprises the administration from about 0.1 to about 150 mg/day of a lyophilized formulation of Compound 1 provided herein and from about 50 to about 200 mg/m$^2$/day of a second active ingredient daily for three to four weeks and then one or two weeks of rest. In certain embodiments, the number of cycles during which the combinatorial treatment is administered to a patient is ranging from about one to about 24 cycles, from about two to about 16 cycles, or from about four to about three cycles.

6.6.4 Patient Population

In certain embodiments of the methods provided herein, the subject is an animal, preferably a mammal, more preferably a non-human primate. In particular embodiments, the subject is a human. The subject can be a male or female subject.

Particularly useful subjects for the methods provided herein include human cancer patients, for example, those who have been diagnosed with leukemia, including acute myeloid leukemia, acute lymphocytic leukemia, chronic myelogenous leukemia, and chronic myelogenous leukemia. In certain embodiments, the subject has not been diagnosed with acute promyelocytic leukemia.

In some embodiments, the subject has a higher than normal blast population. In some embodiments, the subject has a blast population of at least 10%. In some embodiments, the subject has a blast population of between 10 and 15%. In some embodiments, the subject has a blast population of at least 15%. In some embodiments, the subject has a blast population of between 15 and 20%. In some embodiments, the subject has a blast population of at least 20%. In some embodiments, the subject has a blast population of about 10-15%, about 15-20%, or about 20-25%. In other embodiments, the subject has a blast population of less than 10%. In the context of the methods described herein, useful subjects having a blast population of less than 10% includes those subjects that, for any reason according to the judgment of the skilled practitioner in the art, are in need of treatment with a compound provided herein, alone or in combination with a second active agent.

In some embodiments, the subject is treated based on the Eastern Cooperative Oncology Group (ECOG) performance status score of the subject for leukemia. ECOG performance status can be scored on a scale of 0 to 5, with 0 denoting asymptomatic; 1 denoting symptomatic but completely ambulant; 2 denoting symptomatic and <50% in bed during the day; 3 denoting symptomatic and >50% in bed, but not bed bound; 4 denoting bed bound; and 5 denoting death. In some embodiments, the subject has an ECOG performance status score of 0 or 1. In some embodiments, the subject has an ECOG performance status score of 0. In some embodiments, the subject has an ECOG performance status score of 1. In other embodiments, the subject has an ECOG performance status score of 2.

In certain embodiments, the methods provided herein encompass the treatment of subjects who have not been previously treated for leukemia. In some embodiments, the subject has not undergone allogeneic bone marrow transplantation. In some embodiments, the subject has not undergone a stem cell transplantation. In some embodiments, the subject has not received hydroxyurea treatment. In some embodiments, the subject has not been treated with any investigational products for leukemia. In some embodiments, the subject has not been treated with systemic glucocorticoids.

In other embodiments, the methods encompass treating subjects who have been previously treated or are currently being treated for leukemia. For example, the subject may have been previously treated or are currently being treated with a standard treatment regimen for leukemia. The subject may have been treated with any standard leukemia treatment regimen known to the practitioner of skill in the art. In certain embodiments, the subject has been previously treated with at least one induction/reinduction or consolidation AML regimen. In some embodiments, the subject has undergone autologous bone marrow transplantation or stem cell transplantation as part of a consolidation regimen. In some embodiments, the bone marrow or stem cell transplantation occurred at least 3 months prior to treatment according to the methods provided herein. In some embodiments, the subject has undergone hydroxyurea treatment. In some embodiments, the hydroxyurea treatment occurred no later than 24 hours prior to treatment according to the methods provided herein. In some embodiments, the subject has undergone prior induction or consolidation therapy with cytarabine (Ara-C). In some embodiments, the subject has undergone treatment with systemic glucocorticosteroids. In some embodiments, the glucocorticosteroid treatment occurred no later 24 hours prior to treatment according to the methods described herein. In other embodiments, the methods encompass treating subjects who have been previously treated for cancer, but are non-responsive to standard therapies.

Also encompassed are methods of treating subjects having relapsed or refractory leukemia. In some embodiments, the subject has been diagnosed with a relapsed or refractory AML subtype, as defined by the World Health Organization (WHO). Relapsed or refractory disease may be de novo AML or secondary AML, e.g., therapy-related AML (t-AML).

In some embodiments, the methods provided herein are used to treat drug resistant leukemias, such as chronic myelogenous leukemia (CML). Thus, treatment with a compound provided herein could provide an alternative for patients who do not respond to other methods of treatment. In some embodiments, such other methods of treatment encompass treatment with Gleevec® (imatinib mesylate). In some embodiments, provided herein are methods of treatment of Philadelphia chromosome positive chronic myelogenous leukemia (Ph+CML). In some embodiments, provided herein are methods of treatment of Gleevec® (imatinib mesylate) resistant Philadelphia chromosome positive chronic myelogenous leukemia (Ph+CML).

Also encompassed are methods of treating a subject regardless of the subject's age, although some diseases or disorders are more common in certain age groups. In some embodiments, the subject is at least 18 years old. In some embodiments, the subject is more than 18, 25, 35, 40, 45, 50, 55, 60, 65, or 70 years old. In other embodiments, the subject is less than 65 years old. In some embodiments, the subject is less than 18 years old. In some embodiments, the subject is less than 18, 15, 12, 10, 9, 8 or 7 years old.

In some embodiments, the methods may find use in subjects at least 50 years of age, although younger subjects could benefit from the method as well. In other embodiments, the subjects are at least 55, at least 60, at least 65, and at least 70 years of age. In another embodiment, the subjects have adverse cytogenetics. "Adverse cytogenetics" is defined as any nondiploid karyotype, or greater than or equal to 3 chromosomal abnormalities. In another embodiment, the subjects are at least 60 years of age and have adverse cytogenetics. In another embodiment, the subjects are 60-65 years of age and have adverse cytogenetics. In another embodiment, the subjects are 65-70 years of age and have adverse cytogenetics.

In certain embodiments, the subject treated has no history of myocardial infarction within three months of treatment according to the methods provided herein. In some embodiments, the subject has no history of cerebrovascular accident or transient ischemic attack within three months of treatment according to the methods provided herein. In some embodiments, the subject has no suffered no thromboembolic event, including deep vein thrombosis or pulmonary embolus, within 28 days of treatment according to the methods provided herein. In other embodiments, the subject has not experienced or is not experiencing uncontrolled disseminated intravascular coagulation.

Because subjects with cancer have heterogeneous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual subject with cancer.

It will be appreciated that every suitable combination of the compounds provided herein with one or more of the aforementioned compounds and optionally one or more further pharmacologically active substances is contemplated herein.

6.7 Evaluation of Activity

Standard physiological, pharmacological and biochemical procedures are available for testing the compounds to identify those that possess the desired anti-proliferative activity.

Such assays include, for example, biochemical assays such as binding assays, radioactivity incorporation assays, as well as a variety of cell based assays, including KG-1 cell proliferation assay described in the Example section.

Embodiments provided herein may be more fully understood by reference to the following examples. These examples are meant to be illustrative of pharmaceutical compositions and dosage forms provided herein, but are not in any way limiting.

7. EXAMPLES

The following Examples are presented by way of illustration, not limitation. The following abbreviations are used in descriptions and examples.

SWFI—Sterile Water for Injection
WFI—Water for injection
D5W—Dextrose 5% in Water
HPIβCD—Hydroxypropyl-beta-cyclodextrin
SBEPβCD—Sulfobutylether-β-cyclodextrin sodium salt
TBA—Tert-butyl alcohol
DMA—Dimethylacetamide
HAS—Human serum albumin
FDM—Freeze-drying microscope
SEM—Scanning electron microscope
LT-DSC—Low temperature differential scanning calorimetry
DSC—Differential scanning calorimetry
DVS Dynamic vapor sorption
TGA—Thermogravimetic analysis
GC—Gas chromatography
KF—Karl Fisher "Compound 1, Form C" or "Form C" or "API"" in the Examples herein refers to polymorph Form C of 2-(4-Chlorophenyl)-N-((2-(2,6-dioxopiperidin-3-yl)-1-oxoisoindolin-5-yl)methyl)-2,2-difluoroacetamide. "Compound 1, Form A" or "Form A" in the Examples herein refers to polymorph Form A of 2-(4-Chlorophenyl)-N-((2-(2,6-dioxopiperidin-3-yl)-1-oxoisoindolin-5-yl)methyl)-2,2-difluoroacetamide. The physical and chemical properties of 2-(4-Chlorophenyl)-N-((2-(2,6-dioxopiperidin-3-yl)-1-oxoisoindolin-5-yl)methyl)-2,2-difluoroacetamide are summarized in Table 1.

TABLE 1

Summary of physical and chemical properties of 2-(4-Chlorophenyl)-N-((2-(2,6-dioxopiperidin-3-yl)-1-oxoisoindolin-5-yl)methyl)-2,2-difluoroacetamide

| | |
|---|---|
| Structure | (chemical structure shown) |
| Molecular Formula | $C_{22}H_{18}ClF_2N_3O_4$ |
| Molecular Weight | 461.85 |
| Log D | cLogP = 2.18 (Log D not measured due to solubility) |
| pKa | cpKa = 10.66 (Not measured due to low stability above pH 7) |
| Melting Point | 234° C. (Form C) |
| Appearance | White powder |
| Solubility | Practically insoluble in water (≤1 μg/ml across pH range of 1-8) |
| Solid State Stability | DS is physically stable under all storage conditions. |
| Solution Stability | DS is not stable in solution at pH of 5.0 or above. Hydrolysis is the major degradation pathway. |

TABLE 1-continued

Summary of physical and chemical properties of 2-(4-Chlorophenyl)-N-((2-(2,6-dioxopiperidin-3-yl)-1-oxoisoindolin-5-yl)methyl)-2,2-difluoroacetamide

| | |
|---|---|
| Hygroscopicity | Not hygroscopic |
| Pharmaceutical Form | Crystalline; Anhydrous; five polymorph forms (Form C being the most stable form) |

Example 1: First Formulation Screen

Due to the poor water solubility of Compound 1, Form C, a cosolvent system was required to solubilize the drug compound in a solution prior to lyophilization. Several solubilizing agents and solvents that were considered in this example include hydroxypropyl-beta-cyclodextrin (HPβCD), Sulfobutylether-β-cyclodextrin sodium salt (SBEβCD; Captisol®), Tert-butyl alcohol (TBA), and dimethylacetamide (DMA). The solubilities of Compound 1, Form A in various cosolvent systems were determined and the results are shown in Table 2.

TABLE 2

| Vehicle | Form C (mg/ml) | Form A (mg/ml) |
|---|---|---|
| 5% HP-β-CD | NT | 0.03 |
| 10% HP-β-CD | NT | 0.06 |
| 20% HP-β-CD | NT | 0.15 |
| 5% Captisol ® | NT | 0.03 |
| 10% Captisol ® | NT | 0.06 |
| 20% Captisol ® | 0.10 | 0.13 |
| 30% Captisol ® | 0.19 | 0.30 |
| 40% Captisol ® | NT | 0.32 |
| TBA | NT | 0.06 |
| DMA | <166, >125 | NT |
| 20:80 TBA/pH 4.5 buffer | NT | 0.01 |
| 40:60 TBA/pH 4.5 buffer | NT | 0.19 |
| 60:40 TBA/pH 4.5 buffer | 0.29 | 0.39 |
| 70:30 TBA/pH 4.5 buffer | 0.31 | 0.42 |
| 80:20 TBA/pH 4.5 buffer | 0.33 | 0.47 |
| 90:10 TBA/pH 4.5 buffer | 0.23 | 0.35 |
| 80% TBA/15% pH 4.5 buffer/5% DMA | 0.47 | NT |
| 80% TBA/10% pH 4.5 buffer/10% DMA | 0.58 | NT |
| 70% TBA/25% pH 4.5 buffer/5% DMA | 0.47 | NT |
| 70% TBA/20% pH 4.5 buffer/10% DMA | 0.66 | NT |

It was found that HPβCD and SBEβCD had comparable solubilizing effects on Form A at a concentration range of 5-20%. When the SBEβCD concentration increased from 30% to 40%, the enhancement in drug solubility was very limited. It was also found that the drug solubility reached the highest when the TBA/water ratio was at 80:20. The solubility measurements of Form C in selected cosolvent systems were conducted and the results are also shown in Table 2.

In the first formulation screen, the focus was on various combinations of solvents and excipients that provided a media which allowed adequate drug solubility and stability throughout the process of lyophilization and storage of the final product. The 20 mM citrate buffer solution at pH 4.5 was used as the aqueous phase noting that the drug compound undergoes hydrolysis degradation in solutions at pH 5 or above. Given a target drug loading of 2 mg/vial and the maximum fill volume of 8 ml in a 20 cc vial container, the minimum feasible drug concentration in the bulk solution was 0.25 mg/ml. As shown in Table 2, The API has the highest solubility of 0.33 mg/ml in 80:20 TBA/pH4.5 buffer. However, the solubilities of many commonly used bulking agents such as mannitol, sucrose, and glycine are significantly limited in the 70% v/v or higher TBA solution. To balance the solubility of both API and the excipients in the bulk solution, a 60:40 TBA/pH4.5 citrate buffer solution was used in the first screen as the starting point.

In the first run of formulation screen, seven prototype formulations were prepared with different excipients: mannitol, sucrose, Plasdone C17, Captisol®, proline and glycine.

Table 3 shows the formulations compositions of the seven sublots in the first screen.

TABLE 3

| Formulation No. | I | II | III | IV | V | VI | VII |
|---|---|---|---|---|---|---|---|
| API (mg/ml) | 0.24 | 0.24 | 0.28 | 0.24 | 0.24 | 0.24 | 0.26 |
| Mannitol (mg/ml) | 21 | | 25 | | 21 | | |
| Plasdone C17 (mg/ml) | | 17 | | | | | |
| Sucrose (mg/ml) | | | | 25 | | | |
| Glycine (mg/ml) | | | 17 | | | | 19 |
| PEG300 (mg/ml) | | | | | 4 | | |
| Captisol ® (mg/ml) | | | | | | 17 | |
| Proline (mg/ml) | | | | | | | 7 |
| TBA (% v/v) | 60 | 68.6 | 55.7 | 58.1 | 60 | 59.6 | 56.9 |
| 20 mM citric buffer (% v/v) | 40 | 31.4 | 39.3 | | 40 | | |
| DMA (% v/v) | | | 4.9 | | | | 1.6 |
| Purified water (% v/v) | | | | 39.7 | | 39.7 | 39 |
| 0.1N HCl (% v/v) | | | | 2.2 | | 0.3 | 2.5 |
| 0.1N NaOH (% v/v) | | | | | | 0.4 | |

In Formulations I, II and V, the excipients were dissolved in 20 mM citric buffer solution (pH=4.7) first, then mixed with TBA. Subsequently API was dissolved in the TBA/buffer mixture. In Formulations IV and VI, the excipients were dissolved in purified water followed by a pH adjustment with HCl and the addition of TBA. Then the drug was directly dissolved in the TBA/water mixture. In Formulations III and VII, the API was dissolved in a small amount of DMA first, and then added to the TBA/buffer or TBA/water solution. It was observed that the solution became hazy after the addition of TBA in Formulations IV and VII. It was suspected that glycine in those formulations may have reached its solubility limit in the TBA/water solution.

The pH values of the bulk solution in each preparation step were measured and reported in Table 4.

TABLE 4

| | Sublot (Formulation Nos.) | | | | | | |
|---|---|---|---|---|---|---|---|
| | I | II | III | IV | V | VI | VII |
| pH of excipients in Water or Buffer | 4.8 | 4.8 | 4.7 | 6.2 adjusted to 4.5 | 4.8 | 5.0 adjusted to 4.5 | 6.2 adjusted to 4.5 |
| pH of excipients post TBA addition | 5.7 | 6.1 | 5.6 | 5.0 | 5.8 | 5.2 | 4.9 |
| pH post API addition | 5.8 | 6.1 | 5.9 | 5.0 | 5.8 | 5.2 | 5.0 |

TABLE 4-continued

| | Sublot (Formulation Nos.) | | | | | | |
|---|---|---|---|---|---|---|---|
| | I | II | III | IV | V | VI | VII |
| Final pH (pre filtration) | 5.8 | 6.1 | 5.9 | 5.0 | 5.8 | 5.2 | 5.0 |
| Final pH (post filtration) | 5.8 | 6.1 | 5.9 | 5.0 | 5.6 | 5.3 | 5.1 |
| Post reconstitution | 4.9 | 5.0 | 5.0 | 4.7 | 5.0 | 7.7 | 4.6 |

API addition and filtration had no impact on the pH of the solution. The addition of TBA to the solution caused a big increase in the pH reading, which may not reflect the true pH of the solution because the presence of the organic solvent often interferes with the measurement of the pH meter probes. The pH values of the solutions post reconstitution with purified water were all kept at 5.0 or less except for Formulation VI. A generic and conservative lyophilization cycle was applied to all the seven screened formulations and the process parameters of each freeze drying step were described in Table 5.

TABLE 5

| Step | Shelf Temp. Setpoint (° C.) | Soak Time (hours) | Ramping Rate (° C./hour) | Pressure Setpoint | |
|---|---|---|---|---|---|
| Product Loading/Freezing | 5 | 2 | 30 | Evac. To 12 psia to ensure chamber is airtight | |
| Freezing | −50 | 3 | 30 | | |
| Primary Drying | −28 | 21 | 30 | | |
| Secondary Drying | 25 | 6 | | 60 | microns |
| Stoppering | 25 | | | 14.7 | PSIA |

All the seven formulations displayed acceptable cake appearances after lyophilization. The assay and purity of the lyophilized cakes were measured by HPLC and the moisture content of each formulation was measured by Karl Fisher. The results are shown in Table 6.

TABLE 6

| | Sublot (Formulation Nos.) | | | | | | |
|---|---|---|---|---|---|---|---|
| | I | II | III | IV | V | VI | VII |
| Purity (% area) | 99.3 | 71.7 | 99.3 | 99.2 | 99.4 | 99.2 | 84.6 |
| Assay (% LC) | 95.4 | 93.9 | 95.9 | 112.1 | 108.3 | 106.5 | 78.3 |
| Moisture content (% w/w) | −0.09 | 0.30 | 0.04 | 1.27 | 0.03 | 0.16 | 0.21 |

Formulation VII was ruled out due to its low assay and purity, indicating that glycine and proline may not be adequate stabilizers in the lyophilization process. Formulation II showed low purity due to many interfering peaks of the polymeric excipient in the HPLC chromotograph. It remained to be investigated in the next run.

A few key observations concluded from the first screen are:

Adjusting pH with HCl and/or NaOH exhibited limited buffering capacity and introduced pH variation during the process. Using citrate buffer offered more consistent and robust pH control.

Dissolving the drug substance first to DMA and then adding the API/DMA premix to the respective TBA/buffer solution aided in initial dissolution of the drug substance, which allowed for higher drug concentration and lower TBA concentration in the final bulk solution.

Formulation VI, the formulation containing Captisol®, was able to be reconstituted by purified water or D5W alone at a concentration of 0.24-0.5 mg/ml. All the other formulations required some cosolvents such as ethanol or PEG300 for complete reconstitution.

Example 2: Second Formulation Screen

The preliminary results from the first screen confirmed the lyophilization feasibility of the drug compound. The second formulation screen was designed to evaluate the physical and chemical stability of multiple prototype formulations and to select the lead formulation candidates. The same generic lyophilization cycle as used in the first screen was adopted. 20 mM citrate buffer at pH 4.5 was used in all the formulations except for the one containing glycine (Formulation XIV). API was dissolved in DMA first at a concentration of 40 mg/ml. Then the API/DMA premix was added to the TBA/buffer solution containing the excipients. Dexolve and Kleptose® HPB are the two derivatives of cyclodextrins which have similar physical and chemical properties as Captisol®. They were included in Formulations VIII, IX and X as the alternatives of Captisol®. Mannitol, Plasdone, sucrose and glycine exhibited acceptable formulation characteristics in the first screen and thus continued to be evaluated in the second screen. The excipient levels were adjusted empirically in order to obtain a clear and colorless bulk solution. Formulation XI, the formulation containing human serum albumin (HSA), was discarded during the preparation due to incomplete dissolution of the API. The formulation compositions of the seven sublots are shown in Table 7.

TABLE 7

| Formulation No. | VIII | IX | X | XII | XIII | XIV | XV |
|---|---|---|---|---|---|---|---|
| API (mg/ml) | 0.28 | 0.24 | 0.3 | 0.3 | 0.3 | 0.28 | 0.28 |
| Mannitol (mg/ml) | | | | | | | 12 |
| Plasdone C17 (mg/ml) | | | | 13.3 | | | |
| Sucrose (mg/ml) | | | | | 13.3 | 12 | |
| Glycine (mg/ml) | | | | | | 6.1 | |
| PEG300 (mg/ml) | | | 6.6 | | | | |
| Dexolve (mg/ml) | 24.5 | | | | | | |
| Kleptose ® (mg/ml) | | 21.5 | 13.3 | | | | |
| TBA (% v/v) | 50.4 | 56.6 | 46.3 | 46.3 | 46.3 | 50.4 | 50.4 |
| 20 mM citric buffer (% v/v) | 49 | 42.9 | 53 | 53 | 53 | | 49 |
| DMA (% v/v) | 0.7 | 0.6 | 0.7 | 0.7 | 0.7 | 0.7 | 0.7 |
| Purified water (% v/v) | | | | | | 49* | |

The fill volume of each vial was about 2.5-3 ml to deliver a drug loading of 0.75-0.77 mg/vial. The total solid content of the lyophilized cakes ranged from 40 mg to 75 mg per vial. As shown in Table 8, the pH values of the bulk solutions post reconstitution were all kept around 4.5, which confirmed the buffer capacity of the formulation.

TABLE 8

|  | Sublot (Formulation No.) | | | | | | |
|---|---|---|---|---|---|---|---|
|  | VIII | IX | X | XII | XIII | XIV | XV |
| pH of excipients in Water or Buffer plus TBA | 4.6 | 4.7 | 4.7 | 4.8 | 4.8 | 4.6 | 4.7 |
| pH post API and TBA addition | 5.2 | 5.5 | 5.2 | 5.2 | 5.3 | 4.7 | 5.3 |
| Final pH (post filtration) | 5.1 | 5.6 | 5.4 | 5.4 | 5.4 | 4.9 | 5.3 |
| pH Post reconstitution | 4.5 | 4.6 | 4.5 | 4.5 | 4.5 | 4.4 | 4.5 |

The physical structures of the seven formulations after lyophilization were fully characterized and the results are shown in Table 9.

TABLE 9

| Formulation | VIII | IX | X | XII |
|---|---|---|---|---|
| Color | White, Uniform | White, Uniform | White, Uniform | White, Uniform |
| Structure | Dense | Dense | Porous | Powder |
| Fill Height | 9 mm | 8 mm | 5 mm | 5 mm |
| Cake Height | 4 mm | 6 mm | 3 mm | n/a |
| Side Shrinkage | 2 mm uniform | 1 mm uniform | 2 mm | n/a |
| Top Surface | Matte | Sheen | Matte/Sheen | n/a |
| Side Surface | Matte | Matte | Matte | n/a |
| Topography | Textured, concave | Textured, concave | Textured, concave | n/a |
| Upon Inversion | Cake remains intact and falls to top of vial. | Cake remains intact and adhered to bottom of vial. | Cake remains mostly intact with some chunks dislodged. | n/a |
| Upon Jarring | Cake fractures into pieces. | Cake falls to the top of vial and remains intact | Cake fractures into chunks. | n/a powder. |
| Residual Material | Minimal; bottom with striations | Minimal; bottom with striations | Minimal | Minimal |

Formulations VIII, XIX and XV exhibited elegant cake appearances while Formulations X, XII, XIII and XIV did not retain a good cake structure, with collapsed or fractured chunks of powders in the vial.

All the lyophilized samples were put on stability at 25° C./60% RH and 40° C./75% RH condition. The assay and purity data of each formulation are shown in Table 10. The results indicated that all the formulations in the second screen remained chemically stable for at least 1 month at the long-term and the accelerated stability condition.

TABLE 10

|  |  | Formulation | | | | | | |
|---|---|---|---|---|---|---|---|---|
|  |  | VIII | IX | X | XII | XIII | XIV | XV |
| Initial | Purity (% area) | 97.8 | 98.5 | 99.5 | 98.7 | 98.2 | 98.5 | 99.0 |
|  | Assay (% LC) | 93.5 | 92.1 | 90.7 | 92.0 | 95.2 | 96.1 | 103.9 |
| 40° C./75% RH 1 wk | Purity (% area) | 97.8 | 98.6 | 99.3 | 98.8 | 98.4 | 98.7 | 99.2 |
|  | Assay (% LC) | 93.5 | 93.4 | 92.0 | 93.3 | 97.3 | 100.0 | 105.2 |
| 40° C./75% RH 2 wk | Purity (% area) | 97.9 | 98.5 | 99.3 | 98.8 | 98.2 | 98.7 | 99.1 |
|  | Assay (% LC) | 96.1 | 96.1 | 93.3 | 96.0 | 93.3 | 93.5 | 102.6 |
| 40° C./75% RH 4 wk | Purity (% area) | 97.8 | 98.6 | 99.1 | 98.9 | 98.4 | 98.9 | 99.2 |
|  | Assay (% LC) | 97.4 | 96.1 | 97.3 | 96.0 | 94.7 | 90.9 | 106.5 |
| 25° C./60% RH 2 wk | Purity (% area) | 97.9 | 98.5 | 99.3 | 98.8 | 98.2 | 98.6 | 99.1 |
|  | Assay (% LC) | 96.1 | 96.1 | 93.3 | 96.0 | 90.7 | 97.4 | 102.6 |
| 25° C./60% RH 4 wk | Purity (% area) | 97.8 | 98.6 | 99.4 | 98.8 | 98.2 | 98.7 | 99.2 |
|  | Assay (% LC) | 97.4 | 96.1 | 93.3 | 96.0 | 93.3 | 101.3 | 106.5 |

The physical stability of the seven formulations were characterized by XRPD. The results are illustrated in FIGS. 30A, 30B and 30C. For the initial samples, all the formulations exhibited amorphous forms except for Formulation XIV and XV. A further scan verified that Formulation XIV peaks corresponded to the β-form of glycine and Formulation XV peaks corresponded to the mixed α-form and β-form of mannitol. After the stability samples were stored at 25° C./60% RH for 1 month, a few small peaks of sucrose showed up in the XRPD profile of Formulation XIV in addition to the glycine peaks, and the sucrose peaks also showed up in the XRPD patterns of the Formulation XIII sample. The similar changes in XRPD patterns were observed in the Formulations XIII and XIV 1-month stability samples at 40° C./75% RH to a greater extent. In the mean time, a couple of Formulations XIII and XIV samples after one month storage at 40° C./75% RH were found to exhibit slight color change from off-white to yellowish and the lyophilized powders became tacky.

The reconstitution study was executed on each formulation with four different diluents, namely purified water, D5W, 50% v/v ethanol solution, and 50% v/v PEG300 in D5W solution. The shaking time required for the complete dissolution and the physical appearance of the reconstituted solution were inspected. The results are shown in Table 11.

TABLE 11

| Sublot | Purified Water (3 mL) | D5W (2 ml) | 50:50 Ethanol/water (4 ml) | 50:50 PEG300/D5W (2 ml) |
|---|---|---|---|---|
| Formulation VIII | 20 s c/c; became hazy after 2 h | 20 s c/c; became hazy after 2 h | 30 s, c/c | 30 s, c/c |
| Formulation IX | 40 s c/c; became hazy after 2 h | 40 s c/c; became hazy after 2 h | 30 s, c/c | 30 s, c/c |
| Formulation X | 40 s c/c; became hazy after 2 h | 40 s c/c; became hazy after 2 h | 30 s, c/c | 30 s, c/c |
| Formulation XII | >25 m Slightly cloudy | >25 m Slightly cloudy | 30 s, c/c | 30 s, c/c |
| Formulation XIII | >25 m Slightly cloudy | >25 m Slightly cloudy | 30 s, c/c | 30 s, c/c |
| Formulation XIV | >25 m Slightly cloudy | >25 m Slightly cloudy | 30 s, c/c | 30 s, c/c |
| Formulation XV | >25 m Slightly cloudy | >25 m Slightly cloudy | 30 s, c/c | 30 s, c/c |

Formulation VIII, the dexolve-based formulation, was able to be reconstituted to a clean and colorless solution with 2-3 ml purified water or D5W alone within 20 seconds. Formulations IX and X, the Kleptose®-based formulations, were able to be reconstituted with 2-3 ml purified water or D5W alone as well, but the complete reconstitution required 40-60 seconds. The reconstituted solutions of all the three formulations became hazy after 2 hours, implying that a larger volume of reconstitution diluent may be required to achieve longer in-use stability before the drug is precipitated out of the solution. The rest of the four formulations were not able to be reconstituted by the same volume of the purified water or D5W alone. When 50:50 ethanol/water solution or 50:50 PEG300/D5W solution was used as the reconstitution diluent, all the seven formulations were able to be reconstituted with 2 ml of the diluent within 30 seconds. As the solvent-free diluent is most preferable in terms of easiness of formulation preparation and excipient tolerability, the Dexolve or Kleptose® based formulations are advantageous over the other formulation candidates.

The moisture content of a lyophilized sample could have great impact on its physical and chemical stability. The water content of each lyophilized sample was measured by Karl Fisher. As shown in Table 12, the water contents of all the formulations were less than 0.5% except for Formulation XIV which had a water content of 1.25%.

TABLE 12

| Formulation Nos. | KF Residual Water (% w/w) | TGA Weight Loss (% w/w) | First (Lowest) thermal event (peak ° C.) |
|---|---|---|---|
| Formulation VIII | 0.50 | 3.07 (loss 1) 4.21 (loss 2) 7.28 (Total) | 120.8 |
| Formulation IX | 0.04 | 11.4 | 93.7 |
| Formulation X | −0.09 | 2.79 | 86.5 |
| Formulation XII | 0.08 | 6.04 | 80.8 |
| Formulation XIII | −0.17 | 2.98 | n/d |
| Formulation XIV | 1.25 | 6.74 | 47.3 |

TABLE 12-continued

| Formulation Nos. | KF Residual Water (% w/w) | TGA Weight Loss (% w/w) | First (Lowest) thermal event (peak ° C.) |
|---|---|---|---|
| Formulation XV | 0.14 | 3.07 (loss 1) 2.02 (loss 2) 5.09 (Total) | (46.8 exo) 179.1 |

The total weight loss of each lyophilized sample upon heating from room temperature up to 200° C. was obtained from the TGA measurement. Given the low water content of each sample as indicated in the Karl Fisher measurement, the majority of the weight loss was attributed to the residual solvent held in the lyophilized cake. It showed in Table 12 that the weight loss across all the formulations ranged from 2.8% to 11.4%, implying that most of the lyophilized samples carried relatively high residual solvents. Residual solvent level of the final drug products may cause serious toxicity concerns and therefore need to be tightly controlled according to the ICH guideline Q3C. A GC method was developed upon this point for the quantification of the residual solvent level of the lyophilized formulations for the further development work. The DSC measurement was also conducted on each sample to characterize the thermal response of the lyophilized material. The lowest peak temperature of the first endothermic event identified from the DSC profile reflects the glass transition temperature of the amorphous material. Formulations VIII, IX and XV showed relatively higher glass transition temperatures than the other formulations. In correspondence, these three formulations also exhibited better cake appearance and integrity than the others. Formulations XIII and XIV had the lowest glass transition temperatures among the seven screened formulations, which partially explained their weak physical stability observed at the accelerated stability condition.

Example 3: Third Formulation Screen

As the cake integrities of several formulations in the second screen were not as good as expected, the bulking agent level in the formulations was increased to help stabilize the cake structure during the lyophilization cycle. In order for the bulking agents to achieve a concentration of 50 mg/ml, it was found that the TBA concentration in the bulk solution should be kept at 55% v/v or less. The new lot of API material was dissolved in DMA at a concentration of 60 mg/ml and then added to 50% TBA in citrate buffer solution. The drug concentration in the final bulk solution may increase from previous 0.3 mg/ml up to 1 mg/ml with the increased ratio of API/DMA concentrate. In the third screen, in order to achieve a target drug loading of 2 mg/vial, the drug concentration in the final bulk solution was set at 0.5 mg/ml, corresponding to 4 ml of the fill volume in the vial. Formulations XVI-XXII carried on the same bulking agents as used in the previous screen but at a higher bulking agent level of 50 mg/ml. In Formulation XXIII, a combination of Captisol® and Plasdone C17 was used as bulking agents to test if the addition of the polymer would enhance the solubility of the drug compound so that the same drug concentration can be achieved at a lower TBA level of 30% v/v instead of 50% v/v. Table 13 shows the formulation compositions of the bulk solutions in the third screen.

TABLE 13

| Formulation No. | XVI | XVII | XVIII | XIX | XX | XXI | XXII* | XXIII |
|---|---|---|---|---|---|---|---|---|
| API (mg/ml) | | | | | 0.5 | | | |
| Mannitol (mg/ml) | | | | | | 50 | | |
| Plasdone C17 (mg/ml) | | | | 50 | | | | 5 |
| Sucrose (mg/ml) | | | | | | 50 | 35 | |
| Glycine (mg/ml) | | | | | | | 15 | |
| Captisol ® (mg/ml) | | 50 | | | | | | 45 |
| Dexolve (mg/ml) | 50 | | | | | | | |
| Kleptose ® (mg/ml) | | | 50 | | | | | |
| TBA (% v/v) | | | | 49.58 | | | | 29.75 |
| Citric buffer (% v/v) | | | | 49.58 | | | | 69.42 |
| DMA (% v/v) | | | | 0.83 | | | | |

*pH adjusted by HCl instead of citric buffer

The pH values of the final bulk solutions and the solution post reconstitution of all the screened formulations were kept well below 5.0, as shown in Table 14.

TABLE 14

| Sublot | Formulation XVI | Formulation XVII | Formulation XVIII | Formulation XIX | Formulation XX | Formulation XXI | Formulation XXII | Formulation XXIII |
|---|---|---|---|---|---|---|---|---|
| pH of excipients in 50% v/v TBA/water | 4.6 | 4.7 | 5.0 | 5.0 | 5.0 | 5.0 | 4.3 | 4.5 |
| Final pH including API (post filtration) | 4.9 | 4.9 | 5.2 | 5.2 | 5.1 | 5.1 | 4.4 | 4.7 |
| Post reconstitution | 4.3 | 4.3 | 4.2 | 4.3 | 4.1 | 4.3 | 3.9 | 4.3 |

The same generic lyophilization cycle as used in the first screen was adopted in this study. The physical structures of the eight lyophilized formulations were fully characterized and the results are shown in Table 15.

TABLE 15

| Characteristic | Formulation XVI | Formulation XVII | Formulation XVIII | Formulation XIX |
|---|---|---|---|---|
| Color | White, Uniform | White, Uniform | White, Uniform | White, Uniform |
| Structure | Dense | Dense | Dense | Dense |
| Fill Height | 8 mm | 8 mm | 8 mm | 8 mm |
| Cake Height | 3-5 mm | 4-5 mm | 6-8 mm | 3-6 mm |

TABLE 15-continued

| | | | | |
|---|---|---|---|---|
| Side Shrinkage | 3 mm uniform | 2 mm uniform | 1 mm uniform | 2 mm uniform |
| Top Surface | Matte | Matte | Matte w/a sheen skin | Matte and Sheen |
| Side Surface | Matte | Matte | Matte, with slight creep up the sides | Matte, with slight creep up the sides |
| Topography | Textured, concave at edges, multiple peaks | Textured, concave at edges, multiple peaks | Textured, concave at edges, ⅔ of surface has a sheen skin | Textured, concave at edges, surface is slightly porous |
| Upon Inversion | Cake remains intact and falls to top of vial. | Cake remains intact and falls to top of vial. | Cake remains intact and falls to top of vial. | Cake remains intact and falls to top of vial. |
| Upon Jarring | Cake falls to top of vial Small pieces fall off. | Cake falls to top of vial and breaks into pieces. | Cake falls to top of vial and breaks into pieces. | Cake falls to top of vial Small pieces fall off. |
| Residual Material | Minimal | Minimal | Minimal | Minimal |

| Characteristic | Formulation XX | Formulation XXI | Formulation XXII | Formulation XXIII |
|---|---|---|---|---|
| Color | White, Uniform | White, Uniform | White, Uniform | White, Uniform |
| Structure | Dense | Dense | Porous | Dense |
| Fill Height | 8 mm | 8 mm | 8 mm | 8 mm |
| Cake Height | 7-8 mm | 4-5 mm | 3-4 mm | 3-5 mm |
| Side Shrinkage | 2 mm uniform | 2 mm uniform | N/A | 2 mm uniform |
| Top Surface | Matte and Sheen | Matte and Sheen | Matte | Matte and Sheen |
| Side Surface | Matte, with small creep up the sides. | Matte, with slight creep up the sides | Matte | Matte |
| Topography | Textured, concave at edges, multiple peaks | Textured, concave at edges, multiple peaks | Textured | Smooth, concave along the edges, ½ of surface has a skin. |
| Upon Inversion | Cake remains intact and falls to top of vial. | Cake remains intact and falls to top of vial. | Cake remains intact and falls to top of vial. | Cake remains intact and falls to top of vial. |
| Upon Jarring | Cake falls to top of vial and powderizes | Cake falls to top of vial and breaks into pieces | Cake falls to top of vial and powderizes | Cake falls to top of vial Small amount falls off. |
| Residual Material | Significant | Minimal | Minimal | Minimal |

With the increased level of the bulking agents, all the formulations obtained acceptable cake appearance except for Formulation XXII, the one containing sucrose and glycine. The observation was consistent with what had been seen in Formulation XIV which contained lower levels of sucrose and glycine. As a result of the poor cake integrity and the deteriorated physical stability observed in the second screen, the formulations containing sucrose and/or glycine were ruled out.

The reconstitution performance of the eight formulations in the third screen was consistent with that observed in the second screen. Formulations XVI, XVII, XVIII, the cyclodextrin-based formulations, are the only three formulations that can be reconstituted by purified water or D5W alone. All the rest formulations required cosolvent diluent for complete dissolution including Formulation XXIII. Surprisingly, although it contained Captisol®, the drug solubility of Formulation XXIII was limited rather than enhanced by the presence of Plasdone. Therefore Formulation XXIII was abandoned from the screen.

The Karl Fisher, DSC, and TGA results were summarized in Table 16.

TABLE 16

| Sublot | KF Residual Water (% w/w), 2 vials | TGA Weight Loss (%w/w) | First (Lowest) DSC Thermal Event (peak ° C.) |
|---|---|---|---|
| Formulation XVI | 0.11, 0.03 | 2.42 (loss 1)<br>3.68 (loss 2)<br>6.10 (Total) | 112.7 |
| Formulation XVII | 0.18, 0.06 | 2.96 (loss 1)<br>5.05 (loss 2)<br>8.01 (Total) | 126.5 |
| Formulation XVIII | 0.08, 0.00 | 1.61 (loss 1)<br>9.29 (loss 2)<br>10.90 (Total) | 89.6 |
| Formulation XIX | 0.11, 0.02 | 1.81 (loss 1)<br>6.60 (loss 2)<br>3.55 (loss 3)<br>11.96 (Total) | 95.0 |
| Formulation XX | 0.15, 0.30 | 1.41 (loss 1)<br>0.21 (loss 2)<br>1.62 (Total) | 98.5 |

TABLE 16-continued

| Sublot | KF Residual Water (% w/w), 2 vials | TGA Weight Loss (%w/w) | First (Lowest) DSC Thermal Event (peak ° C.) |
|---|---|---|---|
| Formulation XXI | 0.03, 0.05 | 1.82 (loss 1) 0.78 (loss 2) 2.75 (loss 3) 2.46 (loss 4) 7.81 (Total) | 64.6 |
| Formulation XXII | 0.23, 0.33 | n/d | 58.7 |
| Formulation XXIII | 0.41, 0.28 | 2.09 (loss 1) 5.37 (loss 2) 7.46 (Total) | 105 |

The water contents detected by the Karl Fisher measurements showed that all the formulations contained less than 0.5% water. However, the TGA results indicated that the weight loss of each formulation upon heating varied in a wide range, which predominantly resulted from a high level of residual solvent in the lyophilized cakes. Formulations XVIII and XIX contained relatively higher residual solvent levels than the other formulations, plausibly due to the tendency of solvent molecules bound with the sugar ring of the cyclodextrin and polymeric chain of the povidone. Formulation XX, the mannitol-based formulation, contained the lowest residual solvent of 1.6%. Table 17 provides residual solvents of the selected formulations from the third screen.

TABLE 17

| Formulation | TBA (mg/vial) | DMA (mg/vial) |
|---|---|---|
| Formulation XVI (Dexolve) | 1.4 | 11.0 |
| Formulation XVII (Captisol ®) | 9.0 | 19.1 |
| Formulation XVIII (Kleptose ®) | 11.7 | 11.0 |
| Formulation XX (Mannitol) | 0.12 | 3.18 |

With the completion of the third formulation screen, the Captisol® or Dexolve-based formulation stood out as the lead candidate due to its good physical and chemical stability as well as its fast and simple reconstitution. The Kleptose®-based formulation was considered as the alternative as it displayed similar characteristics as the Captisol®-based formulation. The mannitol-based formulation was also considered as the backup due to its superior cake structure and the lowest residual solvent level among all the screened formulations.

The GC tests were conducted on the aforementioned four lead formulations to acquire a more definite amount of the residual solvents in each individual vial. Therefore, the next run of formulation screen was focused on reducing the solvent level used in the initial bulk solution. Dexolve was used as the sole bulking agent in the screen provided the drug has comparable solubility in Captisol®, Dexolve, or Kleptose® solutions.

Example 4: Fourth Formulation Screen

All the previous formulation development work was targeted at a drug loading of 2 mg/vial. A drug concentration as high as 0.5 mg/ml was achieved by dissolving the API first in DMA at the concentration of 60 mg/ml and then adding the DMA concentration in 50:50 TBA/citrate buffer solution. In order to minimize the residual solvent level in the finished lyophilized drug product, a few approaches were considered:

1. Reducing the initial TBA amount may lead to less residual TBA.
2. Reducing the initial DMA amount may lead to less residual DMA.
3. Reducing the initial cyclodextrin amount may diminish the solvent entrapment in this excipient.
4. Optimizing the freeze drying parameters may facilitate removal of solvents in both sublimation and desorption processes.

To reduce the initial TBA amount in the formulation, a small study was conducted to evaluate the API solubility in varying levels of TBA in the Dexolve-based lead formulations. API was dissolved in DMA at 50 mg/ml and then added to the solution containing Dexolve, citrate buffer and TBA. Table 18 shows the formulation compositions in the solubility study.

TABLE 18

| Formulation | XIV | XV | XVI |
|---|---|---|---|
| API (mg/ml) | 0.5 (added as a 50 mg/ml solution in DMA) | | |
| Dexolve-7 (mg/ml) | 50 | | |
| 20 mM Citrate Buffer (% v/v) | 80 | 70 | 60 |
| TBA (% v/v) | 20 | 30 | 40 |

It was observed that no clear solution was obtained when TBA level was 30% v/v or less. This suggested that a minimum 35-40% v/v TBA is required to maintain a drug concentration at 0.5 mg/ml in the bulk solution. If DMA and/or Dexolve level is also reduced, an even higher level of TBA would be needed. There is little room to move the TBA level down from 50% v/v level used in the third screen. Therefore, it was decided to reduce the target drug concentration in the fourth screen in order to achieve lower solvent content. Given a maximum fill volume of 8 ml in a 20 cc vial and a drug loading of 1 mg/vial instead of 2 mg/vial, the lowest drug concentration to be formulated is 0.125 mg/ml.

The bulk solution compositions of the five formulations in the fourth screen were described in Table 19.

TABLE 19

| Formulation | XXVII | XXVIII | XXIX | XXX | XXXI |
|---|---|---|---|---|---|
| API (mg/ml) | 0.125 | 0.125 | 0.125 | 0.25 | 0.40 |
| Dexolve-7 (mg/ml) | | | 20 | | |
| 20 mM Citrate Buffer (% v/v) | 100 | 75 | 75 | 70 | 65 |
| TBA (% v/v) | n/a | 25 | 25 | 30 | 35 |
| DMA (% v/v) | 0.25 | 0.25 | n/a | 0.50 | 0.79 |
| Fill volume (ml/vial) | 8.24 | 8.24 | 8.24 | 4.12 | 2.5 |
| Total solid content (mg/vial) | 203 | 194 | 194 | 74 | 68 |

Formulations XXVII, XXVIII and XXIX were all prepared at a drug concentration of 0.125 mg/ml. Formulation XXVII contained no TBA while Formulation XXVIII and XXIX contained 25% v/v TBA. Formulation XXIX contained no DMA while Formulation XXVII and XXVIII both had the drug added as a 50 mg/ml solution in DMA. Formulations XXX and XXXI had relatively higher levels of TBA at 30% v/v and 35% v/v, respectively. As a result, they were able to achieve a higher drug concentration at 0.25 mg/ml and 0.40 mg/ml, respectively. Based on the result from the first screen, the formulation containing Captisol® at 17 mg/ml obtained an acceptable cake structure. Therefore, Dexolve of 20 mg/ml instead of 50 mg/ml was used in the new screen to mitigate the solvent entrapment tendency. In the lyophilization cycle of the fourth screen, all the cycle parameters were kept the same as in the previous studies except for the secondary drying. The shelf temperature in the secondary drying step was increased from 25° C. to 40° C. and the drying time was prolonged from 6 hours to 12 hours.

All the five formulations obtained good freeze-dried cake materials, with Formulation XXVII providing the most elegant cake appearance. After being reconstituted with 4 ml D5W, drug precipitation was observed in Rx30 vial within 60 minutes. The other formulations post reconstitution stayed in clear solution for at least 3 hours based on visual observation.

The weight loss of the lyophilized samples measured by TGA was reduced to a great extent as compared with previous lots. In correspondence, the residual solvent level of each formulation detected by the GC method was also reduced, as shown in Table 20.

TABLE 20

| Formulation | TBA (mg/vial) | DMA (mg/vial) | Weight loss from TGA (% w/w) |
| --- | --- | --- | --- |
| XXVII | 0.05 | 11.34 | 1.55 |
| XXVIII | 8.81 | 8.18 | |
| XXIX | 4.67 | n/a | 3.99 |
| XXX | 3.01 | 4.69 | |
| XXXI | 2.25 | 2.86 | 2.17 |

Both the TBA level and the DMA level decreased with the decrease of the total solid content of the lyophilized cake. It was speculated that the less solid content led to the smaller cake thickness, which resulted in higher heat transfer efficiency for the solvent to be removed from the cake. The tiny amount of TBA found in Formulation XXVII was suspected to come from cross contamination. As the TBA-free formulation is the most preferable from the toxicology and regulatory perspective, Formulation XXVII was considered as the primary formulation to move forward in the next stage of formulation development. Formulation XXXI was considered as the backup along with Formulation XX, the mannitol-based formulation. During the formulation preparation, Dexolve revealed some quality issues such as the presence of unknown fibers and large colored particles. Besides, despite its comparable physical and chemical properties with Captisol®, it has not been used in any FDA approved IV drug products, which is a potential regulatory barrier for its use in the clinical study. Hence Captisol® and Kleptose® were used instead in the further development work.

Four formulations were selected out of the formulation screen as the lead candidates for the further process development. The four formulations are shown in Table 21.

TABLE 21

| | Formulation IA | Formulation IC | Formulation II | Formulation III |
| --- | --- | --- | --- | --- |
| API (mg/mL) * | 0.125 | 0.125 | 0.40 | 0.50 |
| Excipients | Captisol® (30 mg/mL) | Kleptose® (30 mg/mL) | Captisol® (20 mg/mL) | Mannitol (50 mg/mL) |
| Citrate buffer (% v/v) | 100 | 100 | 60 | 50 |
| TBA (% v/v) | 0 | 0 | 40 | 50 |

The cyclodextrin levels of the two TBA-free formulations, Formulations IA and IC, were increased from 20 mg/ml to 30 mg/ml to provide some solubility margin as the DMA cosolvent level in the bulk solution was to be further reduced in the process development. The other two formulations, II and III, contained 40-50% TBA to accommodate a higher drug loading than the TBA-free formulations.

Example 5: Thermal Analysis of Lyophilization Formulations

Prior to the process development work, a series of low temperature thermal analysis work were conducted on each of the four lead formulations listed in Table 21 to characterize the physical and chemical behaviors of the formulations in a freeze drying process. In the electrical resistance (ER) measurement, the material was cooled and warmed at an average controlled rate and the deviation in resistance was used to determine an onset temperature of the phase transition upon warming. In the freeze-drying microscope (FDM) measurement, the material was cooled and warmed in a sample cell under the temperature controlled freeze drying stage. Changes in the frozen and dried portions of the sample during the phase transition were visually observed under the microscope and the onset temperature was recorded. In the low temperature differential scanning calorimetry (LT-DSC) method, the sample was cooled to a complete freezing first, and then was warmed at a modulated heating rate. The glass transition event was detected in a resultant reversing heat flow. The minimum freezing temperature required for complete solidification during freezing, the phase transition temperature upon warming, and the temperature at which the first void in the frozen material was observed under FDM upon warming were identified and summarized in Table 22.

TABLE 22

| | Freezing Temp. (FDM) | Freezing Temp. (ER) | Phase Transition Temp. (ER) | Glass Transition Temp. (LT-DSC) | Initial Void Temp. upon warming (FDM) | Product Temp. Range |
| --- | --- | --- | --- | --- | --- | --- |
| Formulation IA | −21.2° C. | −26° C. | −27° C. | −36.6° C. | −30° C. | −32 to −34° C. |
| Formulation IC | −22.9° C. | −12° C. | −12° C. | −20.4° C. | −13.6° C. | −16 to −18° C. |
| Formulation III | −22.1° C. | −20° C. | −20° C. | −34.9° C. (Exotherm) | −41.2° C. | −44 to −46° C. |

TABLE 22-continued

| | Freezing Temp. (FDM) | Freezing Temp. (ER) | Phase Transition Temp. (ER) | Glass Transition Temp. (LT-DSC) | Initial Void Temp. upon warming (FDM) | Product Temp. Range |
|---|---|---|---|---|---|---|
| Formulation III | −21.2° C. | −20° C. | −17° C. | −33.5° C. (Endotherm) | −32° C. | −36 to −38° C. |

In general, the ER results are for reference only and not so specific as FDM or LT-DSC results. The visual results obtained from FDM are considered to be most representative to what occurs in the vial. A recommended product temperature range during primary drying was determined thereafter for complete sublimation with the retention of the cake structure and the absence of collapse. In some cases, the product may still remain stable when the product temperature is slightly higher than the glass transition temperature. Typically the product is kept 2-3° C. below the initial void temperature, which is considered to be representative of the collapse temperature of the lyophilized cake, to provide some safety margins. For the mannitol-based formulation III, LT-DSC results indicated an exothermic event in the 2° C./min scan which was not seen in the 10° C./min scan. This suggested that the event is warming rate dependent. The formulation may benefit from an annealing step prior to primary drying to allow efficient crystallization of the crystalline bulking agent mannitol. The thermal analysis results, especially the recommended product temperature range for primary drying, were used as references in the subsequent process development work.

Example 6: Development of Lyophilization Process

A lyophilization process may consist of three stages: freezing, primary drying, and secondary drying. A liquid formulation is transformed to a lyophilized powder form by going through complete solidification through freezing stage, sublimation of ice and solvents through primary drying, and desorption of residual moisture and solvents through secondary drying. The shelf temperature and chamber pressure in the primary drying and secondary drying are the key process parameters which have great impact on the quality of the finished drug product. Five process development studies were executed to investigate the effect of each key process parameter on the quality of the final lyophilized product. A series of tests were conducted on the finished drug product. The cake appearance and structure was characterized by visual inspection. The reconstituted solution was characterized by visual inspection and the pH measurement. The moisture content of the lyophilized cake was measured by Karl Fisher method. The physico-chemical behaviors of the dried cake at elevated temperatures were characterized by differential scanning calorimetry (DSC) and thermogravimetric analysis (TGA). The residual solvent level was quantified by gas chromatography (GC) method. The assay and purity was measured by HPLC.

Example 7: Influence of Shelf Temperature in Primary Drying on Finished Products The objective of this study was to evaluate the influence of the shelf temperature on the product temperature during primary drying. The shelf temperature was elevated from −34° C. to −16° C. stepwise with the constant chamber pressure of 60 mTorr throughout primary drying. The four lead formulations described in Table 21 were compounded, filled into 20 ml glass vials, and lyophilized with a target drug loading of 1 mg/vial. The cycle parameters were displayed in Table 23.

TABLE 23

| Step | Shelf Temp. Setpoint (° C.) | Soak Time (hours) | Ramping Rate (° C./hour) | Pressure Setpoint |
|---|---|---|---|---|
| Product Loading/ Freezing | 5 | 2 | 30 | Evac. To 12 psia to ensure chamber is airtight |
| Freezing | −50 | 3 | 30 | 60 microns |
| Annealing | −18 | 3 | 30 | |
| Freezing | −50 | 3 | 30 | |
| Primary Drying | −34 | 1.5 | 30 | |
| | −31 | 1.2 | | |
| | −28 | 1.0 | | |
| | −25 | 1.0 | | |
| | −22 | 0.8 | | |
| | −19 | 1.3 | | |
| | −16 | 77.6 | | |
| Secondary Drying | 40 | 12.1 | | |
| Stoppering | 40 | | | 14.7 PSIA |

During the primary drying, it was observed that the product temperature of each formulation increased on average 0.8-1.4° C. per 3° increase in shelf temperature. The product temperature change was more prominent in Formulations II and III than in Formulations IA and IC. The product break temperatures, denoted as the product temperature at which the ice sublimation was completed, were −35.9° C., −34.8° C., −40.7° C., and −40.1° C. for Formulations IA, IC, II and III, respectively. The break temperatures of all the formulations except for Formulation II were below the recommended product temperature ranges obtained from the low temperature thermal analysis. This suggested that collapse could have occurred in Formulation II while the other three formulations attained good retention of the cake structure.

The finished products of the four sublots showed acceptable cake appearance with varying degrees of shrinkage. The assay of each sublot was in an acceptable range of 95-105%. The residual moistures of the four sublots were all less than 0.2%. The lyophilized material was reconstituted with purified water at a volume of 2, 4, and 8 ml. Formulations IA, IC and II rendered a clear and colorless solution which stayed physically stable for 4 hours by visual inspection. Formulation III was cloudy and would require alternative diluent containing organic solvent. The pH of each reconstituted solution was in the range of 4.5-4.9. The residual solvent level of each sublot was quantified by GC and listed in Table 24.

TABLE 24

|  | Formulation IA | Formulation IC | Formulation II | Formulation III |
|---|---|---|---|---|
| Residual DMA (mg/vial) | 7.64 | 6.37 | 4.74 | 0.58 |
| Residual TBA (mu/vial) | 0.04 | 0.05 | 2.11 | 0.07 |

According to the ICH guidance, DMA was considered as Class 2 solvent and the maximum daily uptake was set as 10.9 mg/day. This guidance does not apply to potential new drug products used during the clinical research stages of development. Hence the stated DMA limit is only used as a benchmark. TBA is not listed in the ICH guidance. The maximum daily uptake of residual TBA was set as 0.15 mg/day. Given a top dose of 2 mg/day, the residual DMA and TBA in finished products are expected to be below 5.45 mg/vial and 0.075 mg/vial respectively. All the formulations except for Formulation III exceeded the residual solvent limit. Therefore, process optimization was conducted to further reduce the residual solvent.

Example 8: Influence of Chamber Pressure in Primary Drying on Finished Products This study was designed to evaluate the influence of the chamber pressure on the product temperature during primary drying. The chamber pressure was elevated from 40 mTorr to 200 mTorr stepwise with the constant shelf temperature at −34° C. throughout primary drying. The cycle parameters were described in table 25.

TABLE 25

| Step | Shelf Temp. Setpoint (° C.) | Soak Time (hours) | Ramping Rate (° C./hour) | Pressure Setpoint |
|---|---|---|---|---|
| Product Loading/Freezing |  5 | 2 | 30 | Evac. To 12 psia to ensure chamber is airtight |
| Freezing | −50 | 3 |  |  |
|  |  |  | 30 |  |
| Annealing | −18 | 3 |  |  |
|  |  |  | 30 |  |
| Freezing | −50 | 3 |  |  |
|  |  |  | 30 | 40 microns |
| Primary Drying | −34 | 5.0 |  | 50 microns |
|  |  | 0.8 |  | 60 microns |
|  |  | 1.0 |  | 70 microns |
|  |  | 1.2 |  | 80 microns |
|  |  | 0.3 |  | 90 microns |
|  |  | 21.5 |  | 100 microns |
|  |  | 25.4 |  | 120 microns |
|  |  | 16.8 |  | 140 microns |
|  |  | 5.6 |  | 160 microns |
|  |  | 27.5 |  | 200 microns |
|  |  |  | 30 | 200 microns |
| Secondary Drying | 40 | 12.0 |  | 200 microns |
| Stoppering | 40 |  |  | 14.7 PSIA |

Four sublots were formulated in this study. Formulations IA, III and III were the same as illustrated in Table 21. The only difference from the process study Run #1 was that, the starting concentration of API in DMA was increased from 75 mg/ml to 120 mg/ml to lower the initial amount of DMA in the bulk solution. Formulation IC was not evaluated in this study as it was theorized that Formulation IA containing Captisol® may demonstrate comparable physical and chemical behaviors as Formulation IC, the Kleptose®-based formulation. Instead, Rx4, a Captisol® based, solvent-free formulation was added to the study plan to assess the feasibility of compounding the bulk solution with no aid of TBA or DMA. The formulation dissolves 0.125 mg/ml Form C directly in the same 20 mM citrate buffer solution with 300 mg/ml Captisol®. Drug precipitation was observed in Rx4 during the compounding process and the precipitated drug particles were filtered out prior to the lyophilization. Later a low assay value of 28.8% in the lyophilized sample of Rx4 sublot confirmed that the solvent-free formulation is not a viable option even with ten folds higher cyclodextrin to facilitate solubilization of the drug. Therefore Rx4 was not considered in the further studies.

During the primary drying, it was observed that the product temperature of the sublot Formulation IA, 2, and 3 increased on average 1.1° C. per 10 micron increase in the chamber pressure from 50 to 70 microns. From 80 to 140 microns, product temperature increased approximately 0.5° C. for each 10 micron increment. The product break temperatures were −36.7° C. and −37.7° C. for Rx2 and 3 respectively. The break temperature of Rx3 was within the recommended product temperature range, suggesting that Rx3 sublot was freeze dried with retention and absence of collapse. In contrast, the product break temperature of Rx2 was higher than the recommended product temperature range. Obvious collapse was observed in a few Rx2 sample vials. Formulation IA did not undergo a break temperature implying incomplete sublimation in these sublot vials.

The finished products of the four sublots showed acceptable cake appearance with varying degrees of shrinkage. The assay of the three sublot Formulation IA, II, and III were all in an acceptable range of 95-100%. The moisture content and the reconstitution results of the sublots Formulation IA, II and III in the process Run #2 were similar to those obtained in the process Run #1. The residual solvent level of each sublot was quantified by GC and listed in Table 26.

TABLE 26

|  | Formulation IA | Formulation IC | Formulation II | Formulation III |
|---|---|---|---|---|
| Residual DMA (mg/vial) | 3.71 | NA | 2.21 | 0.4 |
| Residual TBA (mg/vial) | 0.04 | NA | 1.63 | 0.03 |

The reduced residual solvent levels of all the sublots in this study indicated that decreasing the initial amount of DMA charge in the bulk solution is an effective approach to minimize the residual DMA level in the finished drug product.

Example 9: Influence of Chamber Pressure in Secondary Drying on Finished Products This study was designed to evaluate the influence of a higher chamber pressure in the secondary drying on the residual solvent level of the finished drug products. Three formulation sublots, Formulation IC, II, and III were evaluated in this study. The compositions of each formulation were the same as listed in Table 21. The API was dissolved in DMA at a concentration of 120 mg/ml in all the three formulations in this study. Formulation IA was abandoned in this study as Kleptose® was considered advantageous over Captisol® due to similar chemical properties and lower material cost at this point. Based on the product temperature profiles derived from the previous two process studies, the shelf temperature and the chamber pressure of the primary drying in this study were set at −22° C. and 40 microns respectively in order to yield a product temperature range of −40° C. to −42° C. This conservative setting was to ensure all the three formulations retain the structure with absence of collapse during the primary drying. The chamber pressure of the secondary drying was increased from 40 microns to 600 microns in this study. It was expected that a higher chamber pressure would create a more nitrogen rich environment and more efficient heat transfer which may aid in desorption of residual solvents. The cycle parameters were described in Table 27.

TABLE 27

| Step | Shelf Temp. Setpoint (° C.) | Soak Time (hours) | Ramping Rate (° C./hour) | Pressure Setpoint |
|---|---|---|---|---|
| Product Loading/Freezing | 5 | 2 | 30 | Evac. To 12 psia to ensure chamber is airtight |
| Freezing | −50 | 3 | | |
| | | | 30 | |
| Annealing | −18 | 3 | | |
| | | | 30 | |
| Freezing | −50 | 3 | | |
| | | | 30 | 40 microns |
| Primary Drying | −22 | 111 | | 40 microns |
| | | 4 | | 600 microns |
| | | | 30 | 600 microns |
| Secondary Drying | 40 | 12 | | 600 microns |
| Stoppering | 40 | | | 14.7 PSIA |

In this study, the product break temperatures of Formulation IC ranged between −35.2° C. and −38.2° C., much lower than the recommended product temperature range of −16° C. to −18° C. This implied that there is still a lot of room in the further lyophilization cycle optimization. The product break temperatures of Formulations II and III were −38° C. and −39° C. respectively. The break temperatures of Formulation II exceeded the recommended product temperature range, suggesting that a more conservative cycle would be needed for this formulation to avoid the collapse.

The finished products of the three sublots showed acceptable cake appearance with varying degrees of shrinkage. The moisture content and the reconstitution results of the sublots IC, II and III in the process Run #3 were similar to the results in the previous studies. The residual solvent level of each sublot was quantified by GC and listed in Table 28.

TABLE 28

| | Formulation IA | Formulation IC | Formulation II | Formulation III |
|---|---|---|---|---|
| Residual DMA (mg/vial) | NA | 6.22 | 2.7 | 0.62 |
| Residual TBA (mg/vial) | NA | 0.11 | 3.3 | 0.05 |

It showed that the residual DMA level in Formulation IC was still higher than the desired upper limit. Increase in the chamber pressure of the secondary drying had minimal effect on the solvent desorption.

Example 10: Influence of Shelf Temperature and Drying Time in Secondary Drying on Finished Products This study was designed to evaluate the influences of the shelf temperature and the drying time in the secondary drying on the residual solvent level of the finished drug product. Formulation IC was selected as the lead formulation to proceed due to its superior reconstitution performance. Two other variations, Formulations IC, XXXIII and XXXV, were added in this study to evaluate the influences of the excipients on the residual solvent. Formulation XXXIII differed from IC with a lower Kleptose® level of 20 mg/ml. The intent was to evaluate whether reducing Kleptose® concentration would help reduce the residual solvent. A previous solubility study showed that for Formulation IC, the minimum Kleptose® concentration was 25 mg/ml to assure complete drug dissolution in the bulk solution. Therefore when the Kleptose® concentration was reduced to 20 mg/ml in Formulation XXXIII sublot, the API was dissolved in DMA at 60 mg/ml instead of 120 mg/ml to ensure complete drug dissolution in the bulk solution. Formulation XXXV differed from IC with the addition of 40 mg/ml mannitol. The intent was to evaluate whether presence of mannitol providing a more crystalline structure in the lyophilized cake would promote the removal of the residual solvent. The compositions of the three formulations are listed in Table 29.

TABLE 29

| | Formulation IC | Formulation XXXIII | Formulation XXXV |
|---|---|---|---|
| API (mg/mL) | 0.125 (added as 120 mg/ml in DMA) | 0.125 (added as 60 mg/ml in DMA) | 0.125 (added as 120 mg/ml in DMA) |
| Excipients | Kleptose ® (30 mg/mL) | Kleptose ® (20 mg/mL) | Kleptose ® (30 mg/mL) Mannitol (50 mg/mL) |
| Solvents | pH 4.5 citric Buffer (100% v/v) | | |

The shelf temperature and the chamber pressure of the primary drying in this study were set at −28° C. and 60 microns respectively to provide a conservative lyophilization cycle for all the formulations. An annealing step was added during the freezing stage to facilitate the crystallization of mannitol in Formulation XXXV. Secondary drying was conducted at an increased shelf temperature of 50° C. for 12, 18, and 24 hours. Sample vials were pulled out of the lyophilizer at each time point to check the residual solvent level change over time. The cycle parameters were described in Table 30.

TABLE 30

| Step | Shelf Temp. Setpoint (° C.) | Soak Time (hours) | Ramping Rate (° C./hour) | Pressure Setpoint |
|---|---|---|---|---|
| Product Loading/Freezing | 5 | 2 | 30 | Evac. To 12 psia to ensure chamber is airtight |
| Freezing | −50 | 3 | | |
| | | | 30 | |
| Annealing | −18 | 3 | | |
| | | | 30 | |
| Freezing | −50 | 3 | | |
| | | | 30 | 60 microns |

TABLE 30-continued

| Step | Shelf Temp. Setpoint (° C.) | Soak Time (hours) | Ramping Rate (° C./hour) | Pressure Setpoint |
|---|---|---|---|---|
| Primary Drying | −28 | 104 | 30 | 60 microns 60 microns |
| Secondary Drying | 50 | 12, 18, 24 | | 60 microns |
| Stoppering | 50 | | | 14.7 PSIA |

The product break temperature ranged from −33° C. to −36° C. in primary drying, which was way below the recommended product temperature of Formulation IC from LT-TA. This suggested that the current lyophilization cycle was too conservative and there was still room to increase the shelf temperature and/or the chamber pressure in primary drying to shorten the drying time in further development. The finished products of the three sublots showed acceptable cake appearance with varying degrees of shrinkage. The residual solvent level of each sublot was quantified by GC and listed in Table 31.

TABLE 31

| Drying time | Formulation IC (mg/vial) | Formulation XXXIII (mg/vial) | Formulation XXXV (mg/vial) |
|---|---|---|---|
| 12 hr | 5.8 | 11.2 | 5.6 |
| 18 hr | 5.7 | 11.2 | 5.8 |
| 24 hr | 5.7 | 11.2 | 5.5 |

It showed that the residual DMA level in Formulation IC was reduced slightly from 6.2 mg/vial in Run #3 to 5.8 mg/vial. Prolonged drying time beyond 12 hour has no impact on the removal of the residual solvent. Formulation XXXIII showed the highest residual DMA level among the three sublots mainly because its initial DMA charge was doubled the amount in the other two formulations. Formulation XXXV had similar residual DMA level as Formulation IC, indicating that addition of mannitol had little impact on the removal of the residual DMA. As the result showed a strong correlation between the initial DMA charge to the bulk solution and the residual DMA in the lyophilized cake, it was decided to further reduce the initial DMA charge in the formulation in the next study in order to bring down the residual solvent level.

Example 11: Refinement of the Formulation and Lyophilization Process Parameters This study was designed to refine the formulation and process parameters of the lead formulation IC based on the previous process study results. First of all, a quick solubility study was conducted to evaluate the maximum feasible concentration of API in DMA. When API was dissolved in DMA at 150 mg/ml and added to the bulk solution, undissolved particles were observed prior to filtration and drug precipitation occurred in the bulk solution after overnight storage. When API was dissolved in DMA at 135 mg/ml and added to the bulk solution, the clear and colorless solution was obtained and remained stable after overnight storage. Therefore the API in DMA solution concentration was increased from 120 mg/ml in the last study to 135 mg/ml in the new formulation ID. The compositions of the other ingredients in Formulation ID remained the same as in Formulation IC and were described in Table 32.

TABLE 32

| | Formulation ID |
|---|---|
| API (mg/mL) | 0.125 (added as 135 mg/ml in DMA) |
| Excipients | Kleptose ® (30 mg/mL) |
| Solvents | pH 4.3 citrate Buffer |

The target pH value of the citrate buffer was adjusted from 4.5 to 4.3 to ensure more robust solution stability below pH 4.5. The subsequent HPLC tests confirmed that both the assay and the purity of the filtered bulk solution remained stable with no obvious degradation growth within 8 hours (data not shown). Therefore the recommended holding time for the bulk solution upon preparation is 8 hours at ambient condition.

In the lyophilization cycle, the shelf temperature and the chamber pressure of primary drying were elevated to −16° C. and 140 microns respectively to enhance the sublimation rate. The more aggressive process parameters reduced the primary drying time from over 100 hours in the previous study to about 60 hours. To add some safety margin, the final primary drying time was set at 70 hours. Secondary drying was processed at 50° C. and 140 microns for 12 hours. The cycle parameters are described in Table 33.

TABLE 33

| Step | Shelf Temp. Setpoint (° C.) | Soak Time (hours) | Ramping Rate (° C./hour) | Pressure Setpoint |
|---|---|---|---|---|
| Product Loading/Freezing | 5 | 2 | 30 | Evac. To 12 psia to ensure chamber is airtight |
| Freezing | −50 | 3 | 30 | |
| Primary Drying | −16 | 70 | 30 | 140 microns 140 microns |
| Secondary Drying | 50 | 12 | | 140 microns |
| Stoppering | 50 | | | 14.7 PSIA |

The temperature profile of the lyophilization cycle is illustrated in FIG. 31.

Product break temperature ranges from −28° C. to −30° C. during primary drying suggesting that the product was dried with absence of collapse and there is still room to improve the primary drying rate in further development.

The finished product of Formulation ID showed dense and uniform cake appearance. The moisture content is below the detection limit of the Karl Fisher method. The residual DMA level dropped to 4.2 mg/vial, which was below the target upper limit of 5.45 mg/vial. The resulting assay value was unexpectedly high at 110.8%. Compounding the API in DMA by volume was identified to be the high risk step contributing to the high assay. It was suggested to compound by weight in lieu of volume in future studies. The reconstitution performance was comparable to previous Formulation IC samples. Overall, the results of the finished product testing were considered to be acceptable for the FIH clinical study.

Summary of Process Development

Five process studies were executed in series to investigate the impact of the critical process parameters on the quality of finished drug products, especially the residual solvent content. The refinement of the formulation was conducted concurrently with the process development. It was found that presence of cyclodextrin in the formulation led to entrapment of the residual DMA in the dried cake. Secondary drying had minimal impact on the removal of the residual DMA. Reducing initial DMA charge in the formulation and using more aggressive cycle parameters in primary drying helped to reduce the residual DMA. The formulation ID and the lyophilization process identified in the last process study were taken to the scale up demo batch for evaluation. A complete process diagram including compounding, freeze-drying, filtration, filling, and packaging was illustrated in FIG. 32.

Example 12: Stability of Finished Drug Products

Preliminary stability studies have been performed during the formulation screen. Among all the prototype formulations, Formulation IX composition is the closest to the FIH formulation. Formulation IC which was evaluated towards the end of the process development has exactly the same composition as the FIH formulation except for the residual solvent level. Table 34 compares the formulation compositions of IX and IC as opposed to the FIH formulation.

TABLE 34

| Lot No. | Formulation IX | Formulation IC | Formulation ID (FIH) |
|---|---|---|---|
| Form C (mg/vial) | 0.76 | 1.0 | 1.0 |
| Citric acid anhydrous, USP (mg/vial) | 6.1 | 17.7 | 17.7 |
| Sodium citrate anhydrous, USP (mg/vial) | 8.2 | 17.6 | 17.6 |
| Kleptose ® HPB, parenteral grade (mg/vial) | 67 | 240 | 240 |
| TBA (in process media) | Removed upon drying | 0 | 0 |
| DMA, PW (in process media)* | Removed upon drying | | |
| Total | 82.1 | 276.3 | 276.3 |

The stability data of Formulation IX and Formulation IC is presented in Table 35.

TABLE 35

| | Purity (% area) | | Assay (% label claim) | |
|---|---|---|---|---|
| Formulation No. | IX | IC | IX | IC |
| Initial | 98.5 | 97.8 | 93.0 | 101.0 |
| 1 mo @ 40° C./75% RH | 98.6 | 97.9 | 96.3 | 104.6 |
| 3 mo @ 40° C./75% RH | 99.6 | / | 96.0 | / |
| 1 mo @ 25° C./60% RH | 98.6 | / | 96.5 | / |
| 3 mo @ 25° C./60% RH | 99.6 | / | 95.8 | / |

Formulation IX samples remained stable at the accelerated condition of 40° C./75% RH for three months with no obvious degradant growth. Similarly, Formulation IC samples remained stable at the accelerated condition of 40° C./75% RH for one month. The accelerated stability data obtained so far showed very promising results indicating that finished drug products could have an acceptable shelf life under room temperature storage condition.

Example 13: In-Use Stability of Reconstituted Solutions

Reconstitution studies were conducted with either D5W or purified water with different volumes from 2 ml to 8 ml. Similar reconstitution performance was observed regardless of the type or the volume of the diluents. Osmolality measurement was conducted on each reconstituted solution and the results are shown in Table 36.

TABLE 36

| Diluent volume | 2 ml | 8 ml |
|---|---|---|
| D5W | 636 ± 2 mOsm/kg | 404 ± 1 mOsm/kg |
| Purified water | 283 ± 0 mOsm/kg | 72 ± 1 mOsm/kg |
| Water For Injection | 301 ± 0 mOsm/kg | / |

It was found that reconstitution with 2 ml purified water rendered an osmolality of 283 mOsm/kg. This value is very close to the human plasma osmolality of 285-295 mOsm/kg, while the other three reconstituted solutions exhibited very distinct osmolality values. Subsequently the same measurement was repeated with 2 ml water for injection (WFI) and the osmolality value of 301 mOsm/kg was obtained. As a result, 2 ml water for injection was recommended as the reconstitution diluent due to its physiologically isotonic characteristic and used in the following reconstitution studies to evaluate the in-use stability of the reconstituted solution. The assay and purity of the reconstituted solution were measured by HPLC every two hours for 8 hours. The results are shown in Table 37.

TABLE 37

| Time Point | Assay (% LC) | Purity (% area) | Hydrolysis Degradant 1 (% area) | Hydrolysis Degradant 2 (% area) |
|---|---|---|---|---|
| T = 0 | 108.8 | 97.90 | 0.16 | 0.39 |
| T = 2 hr | 109.1 | 97.91 | 0.16 | 0.39 |
| T = 4 hr | 108.4 | 97.91 | 0.16 | 0.39 |
| T = 6 hr | 108.4 | 97.90 | 0.16 | 0.40 |
| T = 8 hr | 108.5 | 97.89 | 0.17 | 0.40 |

The in-use stability data demonstrated that the formulation solution upon reconstitution remained stable for 8 hours at room temperature condition. Meanwhile no drug precipitation was observed after overnight storage at room temperature condition by visual inspection, assuring the physical stability of the reconstituted solution.

Based on the aforementioned stability results, the proposed reconstitution procedures are described as follows:

Reconstitute each vial with 2 mL sterile water for injection. Gently shake or roll the vial until all solids are dissolved. The resulting solution will contain Form C 0.50 mg/mL. The solution should be clear and colorless. The reconstituted solution remains stable in the vial at room temperature for 8 hours. Inspect the solution visually for particulate matter and discoloration prior to administration. Withdraw the required amount of Form C solution to deliver the desired dose.

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

Formulation of the invention are for use in medicine.

Formulations of the invention are for use in the methods of treatment provided herein.

What is claimed:

1. A lyophilized formulation comprising a solid form of 2-(4-chlorophenyl)-N-((2-(2,6-dioxopiperidin-3-yl)-1-oxoisoindolin-5-yl)methyl)-2,2-difluoroacetamide, a buffer and a bulking agent, wherein the solid form is selected from Form A, Form B, Form C, Form D and Form E, wherein Form A has an X-ray powder diffraction pattern comprising peaks at about 15.6, 16.6, 17.2 or 24.8 degrees 2θ;

Form B has an X-ray powder diffraction pattern comprising peaks at about 16.7, 25.6, 15.4 or 16.3 degrees 2θ;

Form C has an X-ray powder diffraction pattern comprising peaks at about 16.7, 16.9, 17.7 or 24.7 degrees 2θ;

Form D has an X-ray powder diffraction pattern comprising peaks at about 14.1, 14.3, 18.8 or 19.1 degrees 2θ; and Form E has an X-ray powder diffraction pattern comprising peaks at about 16.1, 17.0, 21.2 or 22.9 degrees 2θ.

2. The lyophilized formulation of claim 1, wherein the solid form is Form A having an X-ray powder diffraction pattern substantially as shown in FIG. 2.

3. The lyophilized formulation of claim 1, wherein the solid form is Form B having an X-ray powder diffraction pattern substantially as shown in FIG. 9.

4. The lyophilized formulation of claim 1, wherein the solid form is Form C having an X-ray powder diffraction pattern substantially as shown in FIG. 16.

5. The lyophilized formulation of claim 1, wherein the solid form is Form D having an X-ray powder diffraction pattern substantially as shown in FIG. 23.

6. The lyophilized formulation of claim 1, wherein the solid form is Form E having an X-ray powder diffraction pattern substantially as shown in FIG. 25.

7. The lyophilized formulation of claim 1, wherein the solid form is present in about 0.36% based on the total weight of the lyophilized formulation.

8. The lyophilized formulation of claim 1, wherein the buffer is a citrate buffer.

9. The lyophilized formulation of claim 8, wherein citrate buffer comprises anhydrous citric acid and anhydrous sodium citrate.

10. The lyophilized formulation of claim 9, wherein anhydrous citric acid is present in an amount from about 2% to about 10% based on total weight of the lyophilized formulation.

11. The lyophilized formulation of claim 9, wherein anhydrous sodium citrate is present in an amount from about 2% to about 15% based on total weight of the lyophilized formulation.

12. The lyophilized formulation of claim 1, wherein the bulking agent is selected from mannitol, sulfobutylether-β-cyclodextrin, β-cyclodextrin, hydroxypropyl β-cyclodextrin and methylated β-cyclodextrin.

13. The lyophilized formulation of claim 1, wherein the bulking agent is present in an amount from about 70% to about 95% based on total weight of the lyophilized formulation.

14. The lyophilized formulation of claim 1, wherein the solid form is present in about 0.36%, and the lyophilized formulation comprises anhydrous citric acid in about 6.41%, anhydrous sodium citrate in about 6.37% and hydroxypropyl β-cyclodextrin in about 86.86% based on total weight of the lyophilized formulation.

15. A reconstituted formulation obtained from the lyophilized formulation of claim 1 comprising a diluent.

16. The reconstituted formulation of claim 15, wherein the formulation has a pH of about 4.3.

17. A method of treating cancer comprising administering to a mammal having cancer the reconstituted formulation of claim 15.

18. The method of claim 17, wherein the cancer is leukemia.

19. The method of claim 18, wherein the leukemia is an acute myeloid leukemia.

20. The method of claim 18, wherein the leukemia is relapsed, refractory or resistant to conventional therapy.

21. The method of claim 17, further comprising administering a therapeutically effective amount of a second active agent or a support care therapy.

22. The method of claim 21, wherein the second active agent is 1) a therapeutic antibody that specifically binds to a cancer antigen or a pharmacologically active mutant thereof, 2) a hematopoietic growth factor, 3) a cytokine, 4) an anti-cancer agent, 5) an antibiotic, 6) a cox-2 inhibitor, 7) an immunomodulatory agent, 8) an immunosuppressive agent, or 9) a corticosteroid.

23. The method of claim 17, wherein the cancer is a solid tumor.

24. The method of claim 23, wherein the cancer is a cancer of bladder, bone, blood, brain, breast, cervix, chest, colon, endometrium, esophagus, eye, head, kidney, liver, lymph nodes, lung, mouth, neck, ovaries, pancreas, prostate, rectum, stomach, testis, throat, or uterus.

25. The method of claim 17, further comprising administering calcium, calcitriol, and vitamin D supplementation.

26. A process for preparing a lyophilized formulation, comprising: dissolving a bulking agent and a solid form of 2-(4-chlorophenyl)-N-((2-(2,6-dioxopiperidin-3-yl)-1-oxoisoindolin-5-yl)methyl)-2,2-difluoroacetamide, in a buffer solution to produce a solution; and lyophilizing the resulting solution to produce a powder, wherein the solid form is selected from Form A, Form B, Form C, Form D and Form E, wherein Form A has an X-ray powder diffraction pattern comprising peaks at about 15.6, 16.6, 17.2 or 24.8 degrees 2θ;

Form B has an X-ray powder diffraction pattern comprising peaks at about 16.7, 25.6, 15.4 or 16.3 degrees 2θ;

Form C has an X-ray powder diffraction pattern comprising peaks at about 16.7, 16.9, 17.7 or 24.7 degrees 2θ;

Form D has an X-ray powder diffraction pattern comprising peaks at about 14.1, 14.3, 18.8 or 19.1 degrees 2θ; and Form E has an X-ray powder diffraction pattern comprising peaks at about 16.1, 17.0, 21.2 or 22.9 degrees 2θ.

* * * * *